(12) United States Patent
Van Engelhoven et al.

(10) Patent No.: US 11,071,673 B2
(45) Date of Patent: *Jul. 27, 2021

(54) HUMAN INTERFACE DEVICE FOR EXOSKELETON APPARATUS

(71) Applicant: U.S. Bionics Inc., Emeryville, CA (US)

(72) Inventors: Logan Van Engelhoven, Emeryville, CA (US); Homayoon Kazerooni, Emeryville, CA (US); James Hatch, Emeryville, CA (US); Valantyn Joseph Sean Koziak, Emeryville, CA (US); Minerva Pillai, Emeryville, CA (US); John Jow Kuwata, Emeryville, CA (US)

(73) Assignee: U.S. BIONICS INC., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/100,897

(22) Filed: Nov. 22, 2020

(65) Prior Publication Data

US 2021/0077336 A1 Mar. 18, 2021

Related U.S. Application Data

(63) Continuation-in-part of application No. 16/713,579, filed on Dec. 13, 2019, now Pat. No. 10,864,102.

(Continued)

(51) Int. Cl.
*A61F 5/02* (2006.01)
*B25J 9/00* (2006.01)
(Continued)

(52) U.S. Cl.
CPC ........... *A61H 1/0292* (2013.01); *A61F 5/024* (2013.01); *A61F 5/026* (2013.01); *F41H 1/02* (2013.01);
(Continued)

(58) Field of Classification Search
CPC ........ A61F 5/028; A61F 5/024; A61F 5/0102; A61F 5/01; A61F 5/026; A61F 5/02;
(Continued)

(56) References Cited

U.S. PATENT DOCUMENTS 3,331,367 A * 7/1967 Hastings ................. A61F 5/024
602/19
4,459,979 A * 7/1984 Lewis, Jr. ............. A61F 13/148
602/19
(Continued)

FOREIGN PATENT DOCUMENTS

WO 2013055403 A1 4/2013
WO 2018224175 A1 12/2018
WO WO-2018224175 A1 * 12/2018 ............ B25J 9/0006

OTHER PUBLICATIONS

International Search Report and Written Opinion dated Apr. 23, 2020 cited in Application No. PCT/US19/66300, 11 pgs.
(Continued)

*Primary Examiner* — Tarla R Patel
(74) *Attorney, Agent, or Firm* — Bekiares Eliezer LLP

(57) ABSTRACT

A human interface device is configured to be coupled to a trunk of a person and comprises a frame, a fabric coupled to said frame configurable to be under tensile forces, and a belt configured to be coupled to two side edges of said frame wherein when said belt is worn by said person, an area of said fabric will be pushed against the person's lower back conforming to the shape of the lower back of said person. In operation when said human interface device is worn by said person, the weight of any load coupled to or supported by said frame will be partially supported by the friction force between the area of said fabric which is pushed against the person's lower back, and the person's lower back allowing said person to carry said load.

29 Claims, 50 Drawing Sheets

Related U.S. Application Data

(60) Provisional application No. 62/780,891, filed on Dec. 17, 2018, provisional application No. 62/964,386, filed on Jan. 22, 2020.

(51) Int. Cl.
| | | |
|---|---|---|
| *A61B 5/11* | (2006.01) | |
| *A61F 5/01* | (2006.01) | |
| *A61H 1/02* | (2006.01) | |
| *G21F 3/03* | (2006.01) | |
| *F41H 1/02* | (2006.01) | |
| *F41H 5/08* | (2006.01) | |

(52) U.S. Cl.
CPC ............... *F41H 5/08* (2013.01); *G21F 3/03* (2013.01); *A61H 2201/0192* (2013.01); *A61H 2201/025* (2013.01); *A61H 2201/1253* (2013.01); *A61H 2201/1616* (2013.01); *A61H 2201/1626* (2013.01); *A61H 2201/1645* (2013.01); *A61H 2201/1652* (2013.01); *A61H 2201/1697* (2013.01)

(58) Field of Classification Search
CPC ........ B25J 9/0006; A61B 5/1116; G21F 3/03; F41H 1/02; F41H 5/08; A61H 2201/1253; A61H 2201/1626; A61H 2201/1645; A61H 2201/1652; A61H 2201/1697; A61H 2201/0192; A61H 2201/1616; A61H 2201/025; A61H 1/0292
USPC .......................................................... 602/19
See application file for complete search history.

(56) References Cited

U.S. PATENT DOCUMENTS

| | | | |
|---|---|---|---|
| 4,489,866 A | 12/1984 | Korte | |
| 4,561,578 A | 12/1985 | Bell | |
| 5,161,722 A | 11/1992 | Hembree | |
| 5,232,424 A * | 8/1993 | Pearson | A61F 5/028 2/338 |
| 5,497,922 A | 3/1996 | Tate | |
| 5,547,246 A * | 8/1996 | Lambert | A47C 13/00 224/153 |
| 6,602,214 B2 * | 8/2003 | Heinz | A61F 5/03 128/99.1 |
| 10,864,102 B2 | 12/2020 | Hatch et al. | |
| 2004/0108350 A1 | 6/2004 | Warren | |
| 2008/0021357 A1 | 1/2008 | Firsov | |
| 2011/0266323 A1 | 11/2011 | Kazerooni et al. | |
| 2013/0283492 A1 * | 10/2013 | Ernst, Jr. | A45F 3/08 2/44 |
| 2014/0158839 A1 | 6/2014 | Doyle | |
| 2014/0277739 A1 | 9/2014 | Kornbluh et al. | |
| 2015/0173993 A1 | 6/2015 | Walsh et al. | |
| 2015/0237992 A1 | 8/2015 | Kinskey | |
| 2017/0035187 A1 | 2/2017 | Chapman | |
| 2018/0303699 A1 | 10/2018 | Roma et al. | |
| 2020/0188159 A1 | 6/2020 | Hatch et al. | |

OTHER PUBLICATIONS

Morita et al., "A novel mechanism design for gravity compensation in three dimensional space," Proc. 2003 IEEE/ASME Int. Conf. Adv. Intell. Mechatronica (AIM 2003), vol. 1, 2003, pp. 163-168 (Abstract Only).

Rahman et al., "A simple Technique to Passively Gravity-Balance Articulated Mechanisms," Transaction of the ASEM Journal of Mechanical Design, vol. 117, Jul. 1995, 12 pgs.

Morita et al., "A Novel Mechanism Design for Gravity Compensation in Three Dimensional Space," Proceedings of the 2003 IEEE/ASME, International Conference on Advanced Intelligent Mechatronics (AIM 2003), pp. 163-168.

International Preliminary Report on Patentability dated Feb. 8, 2021 cited in Application No. PCT/US19/66300, 4 pgs.

* cited by examiner

HUMAN INTERFACE DEVICE FOR EXOSKELETON APPARATUS

RELATED APPLICATIONS

This application is a Continuation-In-Part of U.S. application Ser. No. 16/713,579 filed Dec. 13, 2019, which claims the benefit under the provisions of 35 U.S.C. § 119(e) of U.S. Provisional Application No. 62/780,891 filed Dec. 17, 2018. The present application further claims priority to U.S. Provisional Application No. 62/964,386 filed Jan. 22, 2020, which are incorporated herein by reference in its entirety.

It is intended that the referenced application may be applicable to the concepts and embodiments disclosed herein, even if such concepts and embodiments are disclosed in the referenced application with different limitations and configurations and described using different examples and terminology.

FIELD OF THE INVENTION

The present disclosure pertains to the art of load or posture supporting devices to be mounted to the human torso, and more particularly, to a human interface device for an exoskeleton configured to at least partially support the weight of a person's arms, legs, torso, or head.

BACKGROUND OF THE INVENTION

In many occupational and recreational settings, a person must carry loads on the body while standing, walking, or in seated positions. Examples include wearing tool belts, exoskeletons, loaded backpacks, or personal protective equipment such as shielding aprons. Persons engaged in such activities may experience fatigue or soreness in body regions where the load is applied such as the hips or the shoulders. Hiking backpacks are example of load carriage devices where the load weight is distributed on the shoulders and the hip through the backpack shoulder straps and backpack belt. This load may further negatively affect the person's posture. Some exoskeletons attempt to bring the weight of a load all the way to the ground, but require complex and often cumbersome hardware that moves parallel to the user's legs. Even without an added load, the weight of the person's body may also negatively affect the person's posture given sufficient duration of standing, walking, or sitting activities. In some cases, conventional human interface devices for carrying loads (e.g., tool belts, exoskeletons, loaded backpacks, or PPE) do not provide comfort for the person, whether by inadequate conformance to the person's body shape or because of heat buildup due to lack of airflow. Thus, there is a need for a human interface device that allows a person's body to better support an applied load while promoting healthy posture of the persons back without adding to the contact or thermal discomfort of the person. The embodiments of invention described here provide more comfort by conforming to the person's body maximizing the contact area thus minimizing the contact pressure on the person.

SUMMARY OF THE INVENTION

The embodiments provided herein describe a human interface device that maximizes postural or load transfer benefits through the use of a breathable frame and support fabric that closely conforms to a person's body in the lumbar and sacral area. In accordance with a preferred embodiment of the present invention, the human interface device is configured to be coupled to the trunk of a person and comprises a frame, a fabric coupled to said frame configurable to be under tensile forces, and a belt configured to be coupled to two side edges of said frame. When the belt is worn by the person, an area of said fabric will be pushed against the person's lower back conforming to the shape of the lower back of the person. When the human interface device is worn by the person, the weight of any load coupled to or supported by said frame will be partially supported by the friction force between the area of said fabric which is pushed against the person's lower back, and the person's lower back. This allows the person to support and carry the load. Additionally, when the human interface device is worn by the person, the fabric imposes normal contact forces on the person's lower back to maintain the lower back lordotic curve of the person's spine in its natural form.

In accordance with some embodiments of the present invention, said frame is curved at least along one horizontal axis parallel to the ground when the person is standing. In accordance with another embodiment of the present invention, said frame is curved such that the fabric is shaped to conform to the lordotic curve of the lower back of the person. In some embodiments of the present invention, said frame is made of plastic through injection molding process. In some embodiments of invention said frame comprises an element or combination of elements or materials selected from a group consisting of metal, plastic, aluminum, carbon fiber, fiberglass and combination thereof. In some embodiments of invention, the frame is made of a semi rigid material that acts as a spring. In some embodiments of invention, the frame forms a loop and the fabric is under tensile stress in all directions. In some embodiments of invention, said frame is compliant in response to tensile force of said belt and wraps around the person.

In some embodiments of the invention, the fabric is configured to conform to the natural lower back lordotic curve of the person's spine in sagittal plane. In some embodiments of the invention, said fabric is configured to conform to the natural lower back lordotic curve of the person's spine in transverse plane. In accordance with another embodiment of invention, said fabric is a mesh exposing the person's lower back to surrounding air allowing for air flow on person's lower back. This airflow cools the person and preventing him/her from sweating.

In some embodiments of the invention, the human interface device further comprising an upper torso coupling device to secure the frame to the person's upper torso causing more effective contact between the fabric and the person. In some embodiments of invention, said upper torso coupling device comprises two shoulder straps wherein each strap is coupled to the upper edge of the frame from one end and to the lower side of the frame from their second ends. In operation when the shoulder straps are worn by the person, the tightening of the shoulder straps causes more effective contact between the fabric and the person. In some embodiments of invention, said upper torso coupling device comprises two shoulder straps wherein each strap is coupled to the upper edge of the frame from one end and to the belt from their second ends. In operation, when the shoulder straps are worn by the person, the heightening of the shoulder straps causes more effective contact between the fabric and the person. In some embodiments of invention, the human interface device comprises a chest strap coupled to the frame from both sides wherein when the persons' wears the human interface device, the chest strap pushes the person's chest posteriorly causing more effective contact between the fabric and the person. In some embodiments of invention, the human interface device comprises two loop straps coupled to sides edges of the said frame. In operation, when the person's arms pass through the loop straps, the loop straps pull the person's shoulder complex posteriorly causing more effective contact between the fabric and the person.

In some embodiments of invention, the frame of the human interface device further comprises a load bearing structure which is configurable to hold or support a load and is coupled to said frame. In operation, said load bearing structure transfers at least a portion of the load weight to said frame. In some embodiments of invention, the load bearing structure comprises a strut wherein said strut is configured to be coupled to said frame through at least two coupling locations. In some embodiments, said load bearing structure comprises one or a plurality of concentric sections configured to slide into one another allowing for adjustment of the load coupling to the strut. In some embodiments of invention, the load bearing structure and said frame are made as a one-piece body. In some embodiments of invention, said load bearing structure reduces the deformation of the frame. In accordance with other embodiments of invention, said frame comprises a load bearing structure which is configurable to support said load weight and is coupled to the frame thereby decreasing the deformation of the frame.

In some embodiments of invention, the human interface device comprises a tool holder coupled to said frame thereby transferring the weight of the tools to the frame. In some embodiments of the invention, said tool holder is further coupled to said belt from two sides. In operation, when said human interface device is worn, said tool holder wraps around said person in response to tensile force of said belt. In some embodiments of invention, the frame further comprises a load bearing structure which is configurable to hold and support said tool holder and is coupled to said frame. In operation, said load bearing structure transfers at least a portion of said tool holder weight to said frame.

In some embodiments of invention, the human interface device further comprises a wearable exoskeleton which is coupled to said frame. In operation, when said human interface device is worn by said person, the forces from said wearable exoskeleton will be partially supported by the friction force between the area of said fabric which is pushed against the person's lower back, and the person's lower back allowing said person to comfortably carry said wearable exoskeleton. In some embodiments of invention, said frame further comprises a load bearing structure wherein said wearable exoskeleton is coupled to said load bearing structure and therefore said load bearing structure transfers at least a portion of the forces from said wearable exoskeleton to said frame. In some embodiments of invention, the said wearable exoskeleton comprises a shoulder supporting exoskeleton which comprises: an arm link mechanism comprising a proximal link and a distal link configured to rotate relative to each other about a rotating joint and along a first rotational axis substantially orthogonal to a gravity line when said person is standing upright, at least one arm-coupler adapted to couple an upper arm of the person to said arm link mechanism, and a torque generator providing a torque to flex said distal link relative to said proximal link. In operation said torque has the tendency to flex said distal link relative to said proximal link thereby reducing human shoulder forces and torques required to raise said upper arm of the person.

In some embodiments of invention, said frame further comprises a load bearing structure wherein said shoulder supporting exoskeleton is coupled to said load bearing structure and therefore the load bearing structure transfers at least a portion of the forces from said shoulder supporting exoskeleton to said frame. In some embodiments of invention, said torque generator comprises a tensile force generator coupled to said proximal link at a first end of the tensile force generator and coupled to said distal link at a second end of the tensile force generator. In operation, the tensile force in said tensile force generator provides the torque to flex said distal link relative to said proximal link. In some embodiments of invention, said tensile force generator comprises a coil spring element. In some embodiments of invention, the tensile force generator comprises a line coupling said coil spring element to said first proximal link. In some embodiments of invention, the line at least partially encircles a pulley coupled to said second link before its coupling to said first link.

In accordance to another embodiment of invention, the human interface device is configured to be coupled to the trunk of a person and comprises: a frame, a fabric coupled to said frame such that the fabric is under tensile forces, a belt which is configured to be coupled to two side edges of said frame wherein when said belt is worn by said person, an area of said fabric will be pushed against the person's lower back conforming to the shape of the lower back of said person, an arm link mechanism configured to be coupled to said frame. The arm link mechanism comprises: a proximal link and a distal link which are configured to rotate relative to each other along a first rotational axis substantially orthogonal to a gravity line when said person is standing upright, at least one arm-coupler adapted to couple an upper arm of the person to said arm link mechanism and at least one torque generator configured to flex said distal link relative to said proximal link, thereby reducing human shoulder forces and torques required to raise the upper arm of the person. In operation when said belt is worn by the person the forces from arm link mechanism onto said frame will be partially supported by the friction force between the area of said fabric which is pushed against the person's lower back and the person's lower back allowing said person to carry said load.

In accordance to an embodiment of the present invention, a human-coupled tool holding device is configured to be coupled to a trunk of a person and comprises: a frame, a fabric coupled to said frame such that the fabric is under tensile forces, a belt configured to be coupled to two side edges of said frame wherein when said belt is worn by said person, an area of said fabric will be pushed against the person's lower back conforming to the shape of the lower back of said person and a tool holder coupled to said frame. In operation, when said human-coupled tool holding device is worn by said person, the weight of any tool coupled to or supported by said tool holder will be partially supported by the friction force between the area of the fabric which is pushed against the person's lower back and the person's lower back allowing the person to carry said load. In some embodiments of invention, the tool holder is further coupled to the belt from two sides, wherein when said human-coupled tool holding device is worn, the tool holder wraps around the person in response to tensile force of said belt.

In some embodiments of invention, the human interface device is configured to be coupled to the trunk of a person to support a shielding apron comprising a frame compliant in a transverse plane, the frame comprising a load bearing structure configured to reduce a deformation of the frame in a sagittal plane; a fabric coupled to the frame configurable to be under tensile forces; and a belt configured to be coupled to two side edges of the frame wherein when the belt is worn by the person, the frame deforms in the transverse plane and an area of the fabric will be pushed against the person's lower back conforming to a shape of the lower back of the person, wherein when the human interface device is coupled to the person, at least a portion of the weight of the shielding apron supported by the frame will be supported by a friction force between the area of the fabric which is pushed against the person's lower back, and the person's lower back allowing the person to carry the shielding apron.

In a similar embodiment, the human interface device is configured to be coupled to the trunk of a person to support a shielding apron comprising a frame compliant in a transverse plane configurable to support the shielding apron; a belt configured to be coupled to two side edges of the frame and secure the frame to the person, wherein when the belt is worn by the person, the frame deforms in the transverse plane conforming to a shape of the lower back and or hips of the person wherein when the human interface device is worn by the person, at least a portion of the weight of the shielding apron is transferred to the person.

In an additional embodiment, the human interface device is configured to be coupled to the trunk of a person to support a shielding apron comprising a frame, a belt configured to couple the frame to the person, and a fan coupled to said frame to provide airflow; wherein when the human interface device is coupled to the person, the fan provides airflow the person.

DETAILED DESCRIPTION OF THE INVENTION

Reference will now be made in detail to some specific examples of the disclosure including the best modes contemplated by the inventor for carrying out the disclosure. Examples of these specific embodiments are illustrated in the accompanying drawings. While the disclosure is described in conjunction with these specific embodiments, it will be understood that it is not intended to limit the disclosure to the described embodiments. On the contrary, it is intended to cover alternatives, modifications, and equivalents as may be included within the spirit and scope of the disclosure as defined by the appended claims. For example, the structure and mechanisms of the present disclosure will be described in the context of particular materials. However, it should be noted that the structure and mechanisms of the present disclosure may consist of a variety of different materials. In the following description, numerous specific details are set forth in order to provide a thorough understanding of the present disclosure. Particular example embodiments of the present disclosure may be implemented without some or all of these specific details. In other instances, well known structures, mechanisms, and materials have not been described in detail in order not to unnecessarily obscure the present disclosure.

Figure 1:
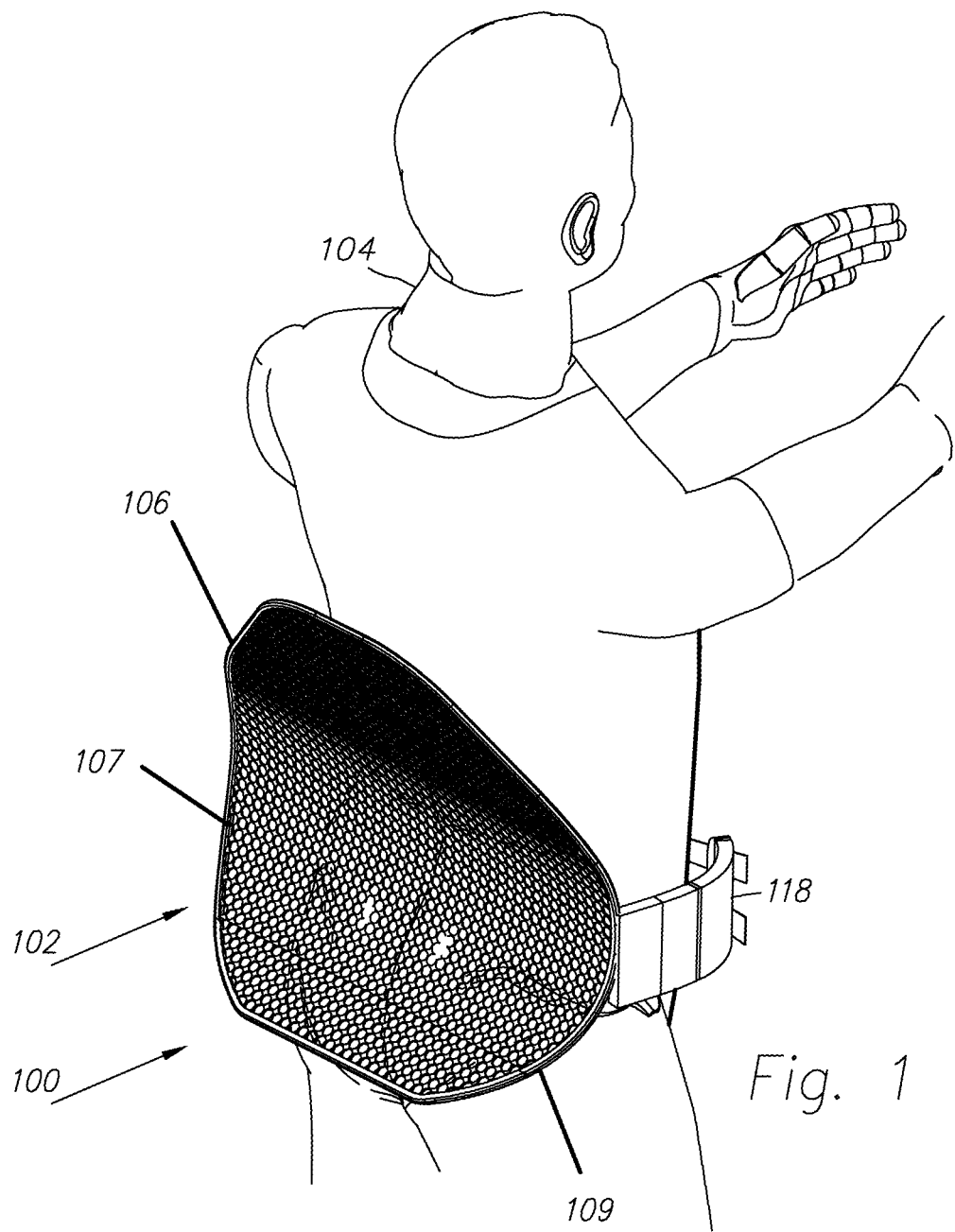
FIG. 1 shows a back perspective view of human interface device on a person.
Figure 2:
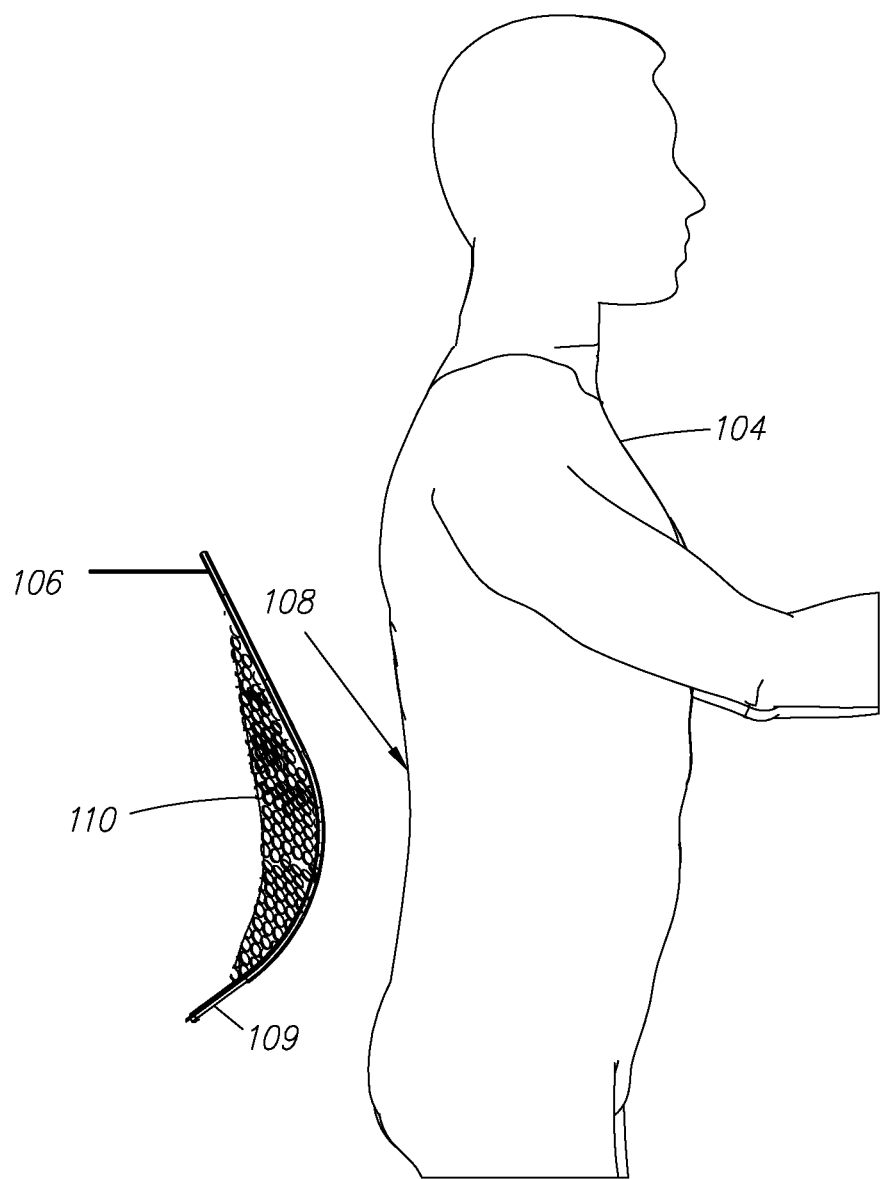
FIG. 2 shows a side view of human interface device on a person.
Figure 3:
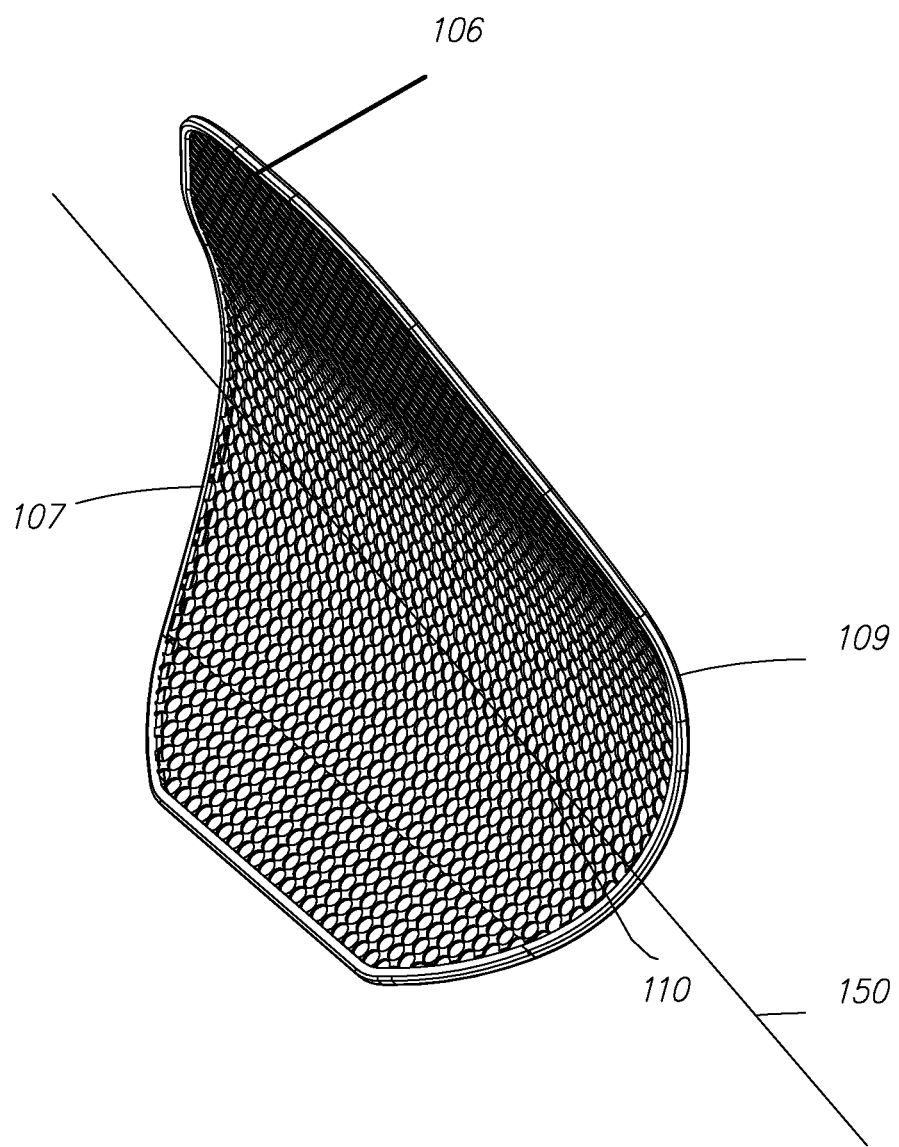
FIG. 3 shows an embodiment of human interface device curved around an axis.

With reference to FIG. 1 through FIG. 3, shown is human interface device 100, in accordance with one or more embodiments. FIG. 1 illustrates a back-perspective view of human interface device 100. Human interface device 100 is configured to be coupled to the trunk of a person 104. The trunk of person 104 may be defined as the torso of the person 104 consisting of the back, hips, chest, abdomen, or shoulders. Human interface device 100 comprises frame 106 and fabric 110 coupled to frame 106 and configured to be under tensile forces. Human interface device 100 further comprises belt 118 coupled to two side edges of frame 106 wherein when belt 118 is worn by person 104, an area of fabric 110 will be pushed against the person's lower back 108 conforming to the shape of lower back 108 of person 104. When human interface device 100 is worn by person 104, the weight of any load coupled to or supported by frame 106 will be partially supported by friction force 152 between the area of fabric 110 pushed against person's lower back 108, and the person's lower back 108, allowing the person 104 to carry the load. In some embodiments, additional forces are applied directly to the low back or hip area of person 104. FIG. 2 illustrates a side view of human interface device 100, and the matching of curve in fabric 110 and the curve of person's lower back 108. FIG. 3 illustrates another perspective view of human interface device 100. As used herein, the human interface device 100 may be referred to herein as an "interface device."

Figure 8A:
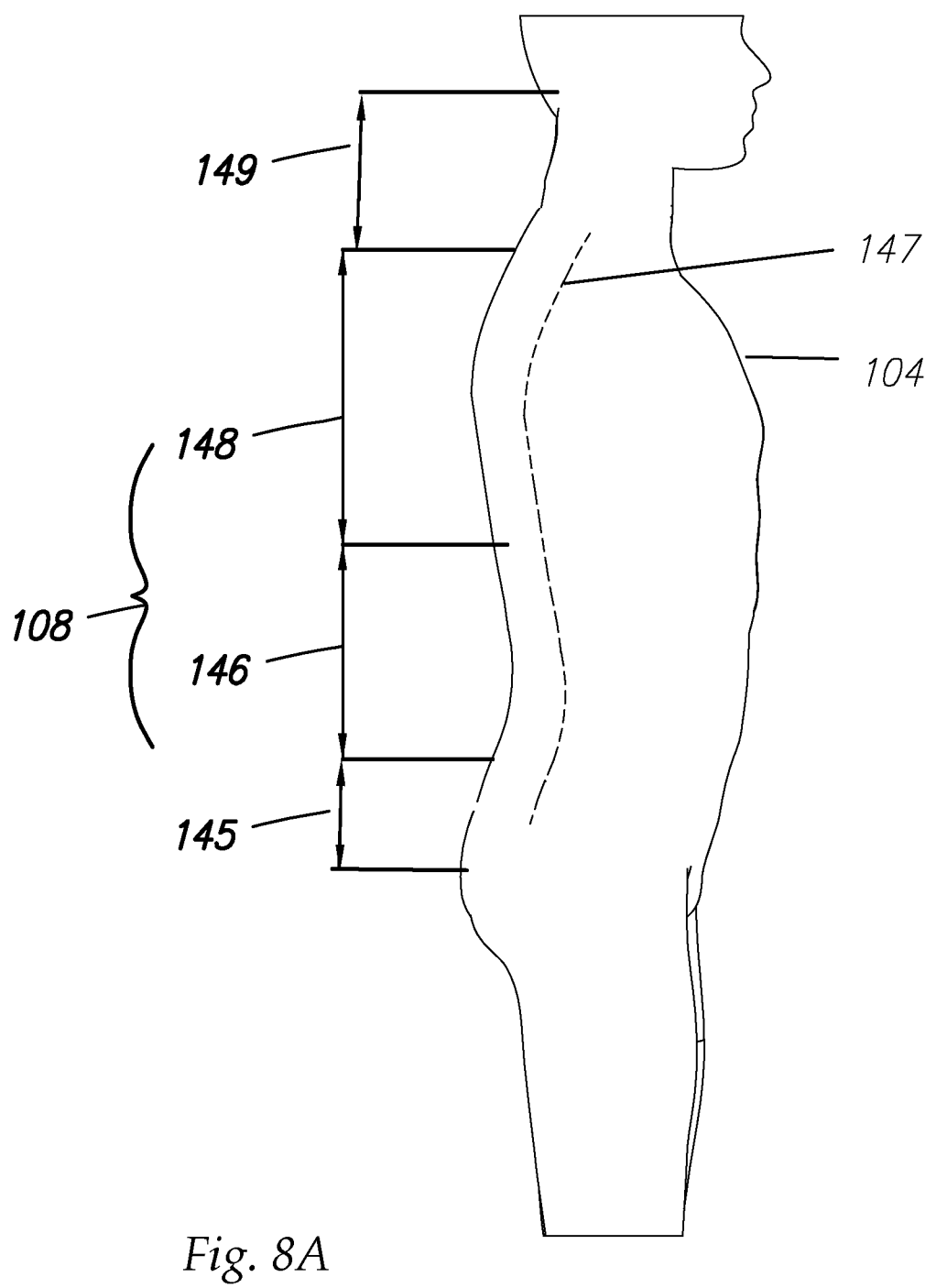
FIG. 8A shows a side view of person with normal posture without human Interface device.

Human interface device 100 is configured to be coupled to trunk area 102 of a person 104. As shown in FIG. 8A, lower back 108 is defined here as the lumbar area 146 and parts of thoracic area 148 and sacral area 145. Human interface device 100 comprises a frame 106 which is curved at least along one horizontal axis parallel to the ground when the person is standing. In some embodiments, frame 106 is curved such that fabric 110 is shaped to conform to the lordotic curve of the lower back 108 of the person 104. Lordotic curve of person 104 may be defined as the shape of person's spine 147 in the lumbar area 146 as shown in FIG. 8 and described further below.

As shown in FIG. 3, frame 106 of human interface device 100 may be bent (curved) around an imaginary axis 150. Two side-edges 107 and 109 are the bent components of frame 106. Frame 106 may further comprise a top or upper edge and a bottom or lower edge coupling two side edges 107 and 109. In some embodiments, the edges of frame 106 may form a closed loop structure. Human interface device 100 further comprises fabric 110 stretched and coupled to frame 106 such that fabric 110 is under tensile forces. In some embodiments, frame 106 forms a loop and fabric 110 is under tensile forces in all directions. In some embodiments, fabric 110 spans a gap, opening, loop, or curve in frame 106 so that where fabric 110 contacts person 104 only air is on the opposing side of fabric 110 and not frame 106. In other embodiments this creates an airgap between fabric 110 and frame 106 on the opposite side of persons lower back 108. This allows cooling airflow to person 104 while human interface device 100 remains able to support a load on person 104 through the friction force between fabric 110 and persons lower back 108. The stretched fabric 110 and bent frame 106 create a curved support surface that substantially matches the inward curve of the lower back 108 of person 104. As used herein, fabric 110 under tensile force may be referred to herein as a "support surface" or "contact surface" of the human interface device.

Figure 4:
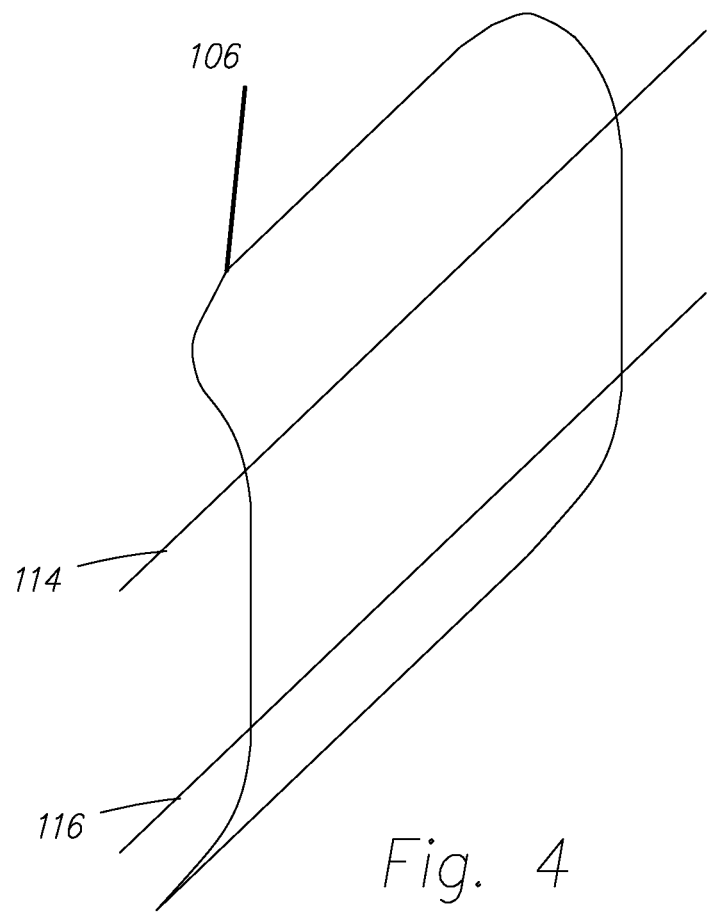
FIG. 4 shows an embodiment of human interface device curved along two axes.

With reference to FIG. 4, shown is a perspective view of another embodiment of human interface device 100, in accordance with one or more embodiments. As shown in FIG. 4, human interface device 100 comprises a configuration in which frame 106 is curved along two horizontal axes 114 and 116 parallel to the ground when in use.

As shown in FIG. 1, in some embodiments, human interface device 100 additionally comprises a belt 118 which is configured to be coupled to two side-edges 107 and 109 of frame 106. When belt 118 is worn by person 104 and it is sufficiently tightened, an area of fabric 110 will be pushed against person's lower back 108. This causes fabric 110 to conform to the shape, or lordotic curve, of lower back 108 of the person covering a relatively large area of the lower back. The pressure between the person's lower back 108 and fabric 110 is small because fabric 110 is in contact with the person through a large area.

Figure 5:
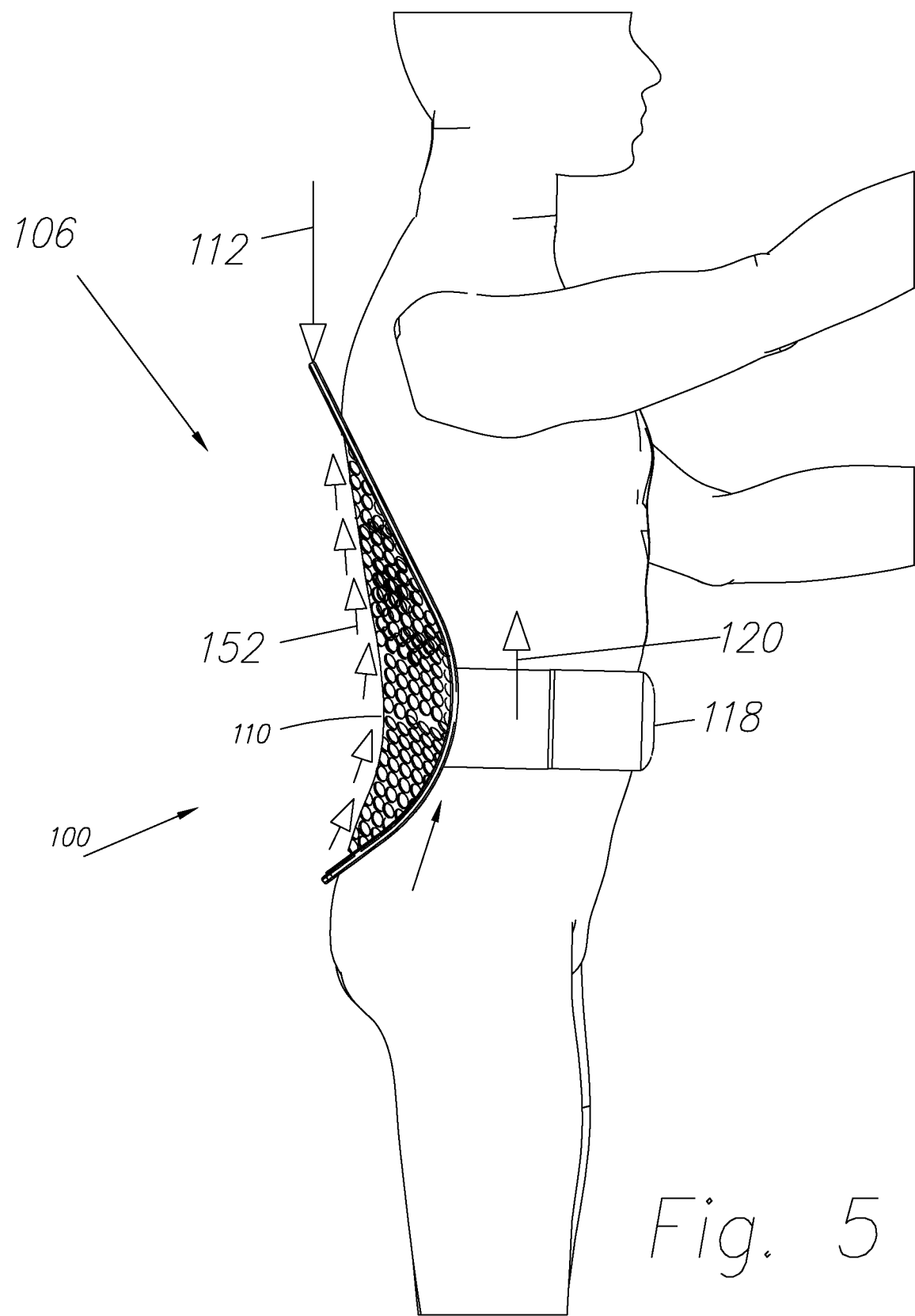
FIG. 5 shows human interface device transferring load to person through friction forces.

With reference to FIG. 5, shown is a side view of human interface device 100 in operation, in accordance with one or more embodiments. As shown in FIG. 5, when human interface device 100 is worn by person 104, a load weight 112 which is coupled to or supported by frame 106 will be partially supported by friction force 152 between the area of fabric 110 which is pushed against the person's lower back 108 and person 104. This allows person 104 to comfortably carry load weight 112. As used herein, "load weight" may be used interchangeably with the term "load force."

In some embodiments, load weight 112 is supported not only by belt 118 but also by frame 106. Belt 118 may sit on the person's hip on both sides of the person; therefore, some of the load weight 112 is taken by belt 118 as hip reaction force 120. However, because frame 106 is in contact with person 104 through a large area, friction force 152 between fabric 110 and person 104 may support the rest of load weight 112. Belt 118 may have sufficient padding and rigidity to effectively transfer weight to person's hip.

FIG. 5 depicts a situation where person 104 is using the invention described here. In this embodiment of invention, load weight 112 is imposed vertically on frame 106, and hip reaction force 120 from the person's hips is supporting some of load weight 112, and friction force 152 between lower back 108 of person 104 and frame 106 supports the rest of the load weight 112. Thus, the supporting force to counteract load weight 112 is well distributed on person 104.

Figure 6:
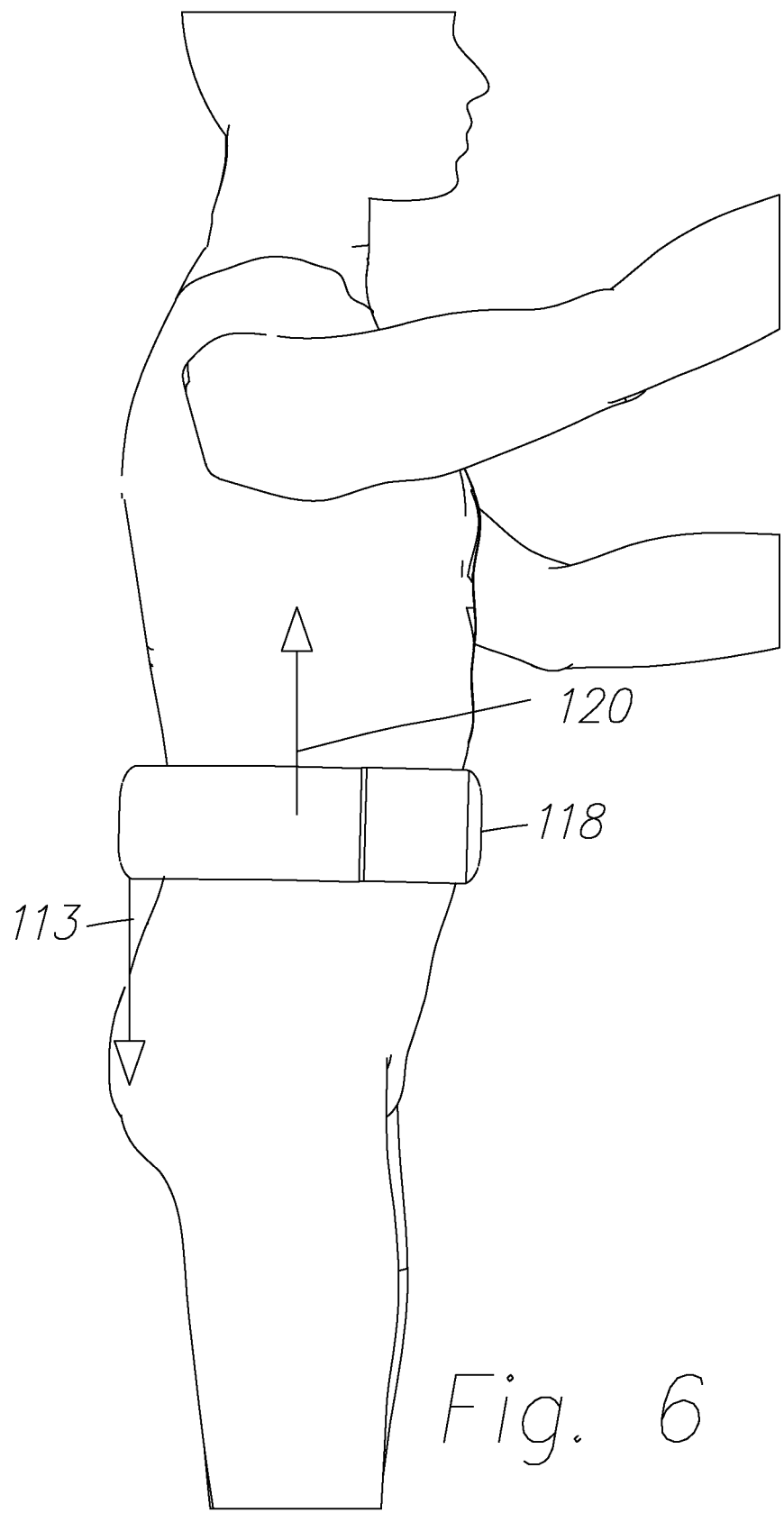
FIG. 6 shows a belt transferring load to a person.

Distributing the load weight 112 across more areas of the person using human interface device 100 should provide a more comfortable experience as compared to merely distributing load weight 112 across the hips. With reference to FIG. 6, shown is a side view of a belt with vertical forces applied and reaction forces shown, in accordance with one or more embodiments. As depicted in FIG. 6, frame 106 is not used and belt 118 takes the entire load weight 113. Load weight 113 may be the weight of a tool belt used by construction workers, for example. In the case of FIG. 6, the entire load weight 113 is supported by hip reaction forces 120. As such, a person using human interface device 100 would have a more comfortable work experience than using only belt 118 since the force is distributed across both lower back 108 and hips of a person.

Figure 7:
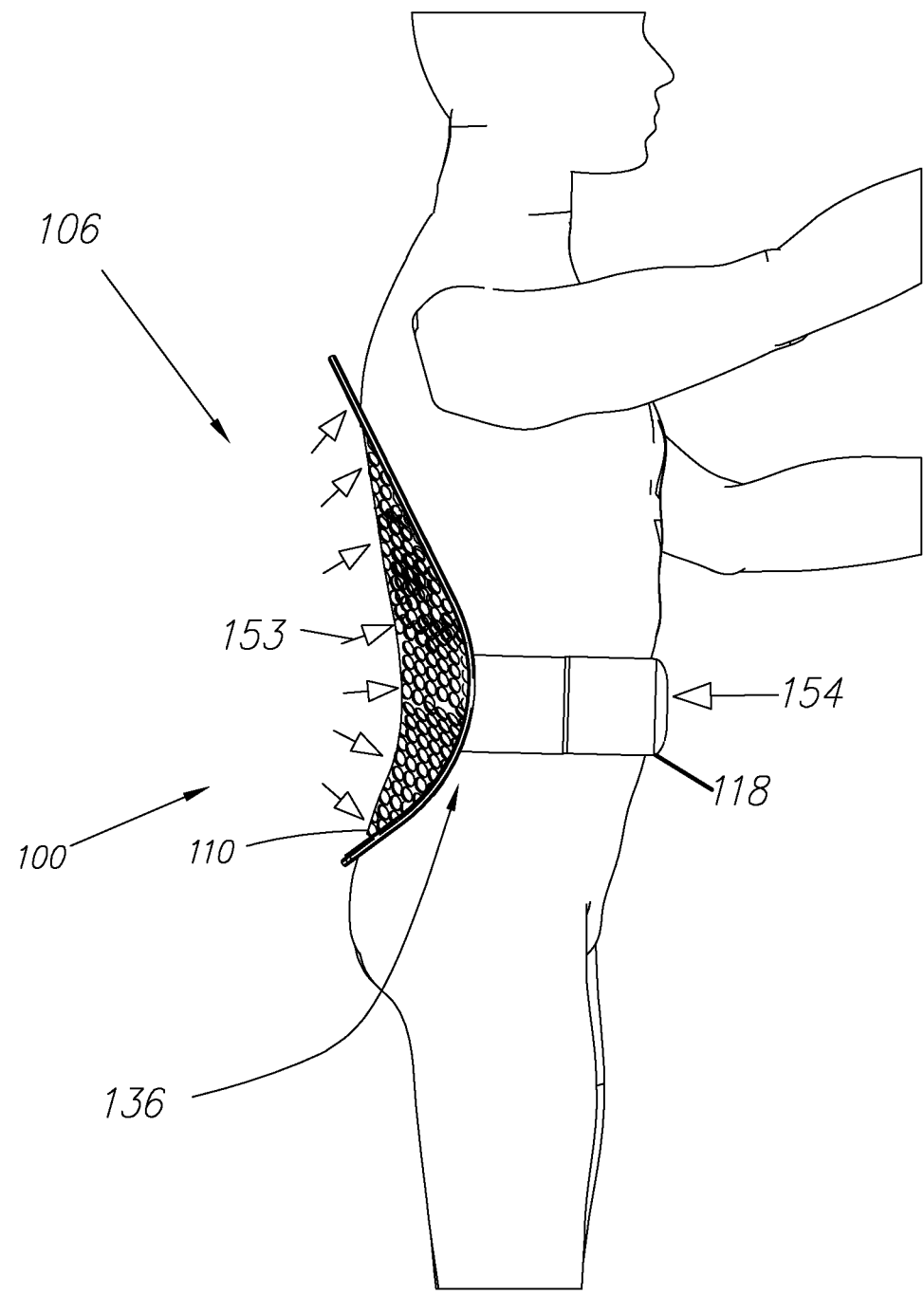
FIG. 7 shows human interface device normal contact forces with a person.

With reference to FIG. 7, shown is a side view of human interface device 100 with normal contact forces shown, in accordance with one or more embodiments. As shown in FIG. 7, in addition to the friction forces 152, as described with reference to FIG. 5, human interface device 100 may additionally create normal contact forces 153 acting at least substantially perpendicular to the contact between fabric 110 and the person's lower back 108 due to belt force 154 from tightening of belt 118. Because human interface device 100 conforms to the curve of person's lower back 108, normal contact forces 153 are imposed on the person's back and are aligned with and follow the concave curvature of person's lower back 108. As such, components of normal contact forces 153 will be oriented in the upwards, downwards, and horizontal directions. Normal contact forces 153 may act perpendicular to the contact between the fabric and the person's back due to belt force 154 from tightening of belt 118, with or without the presence of load weight 112 applied to human interface device 100.

When load weight 112 is applied, human interface device 100 will be pushed downward relative to said person's lower back 108, increasing the magnitude of the normal contact forces 153 against the person's lower back 108 opposing the direction of load weight 112. These normal contact forces 153 will further reduce the magnitude of friction force 152 and hip reaction force 120, and increase comfort. In some embodiments, human interface device 100 rests on the sacral curve of the person wearing the device. This allows transfer of at least part of load weight 112 to the sacrum or tail bone of the sacral area 145 of the person wearing the exoskeleton.

Normal contact forces 153 may also support the lordotic curve of the person's back by pushing upward on the lower section of thoracic area 148 and upper section of lumbar area 146, inward on the middle section of lumbar area 146, and downward on the lower section of lumbar area 146 and sacral area 145. The direction of such normal contact forces 153 helps prevent the person's lordotic curve from collapsing or flattening due to the person's posture or load carried on the shoulders.

Figure 8B:
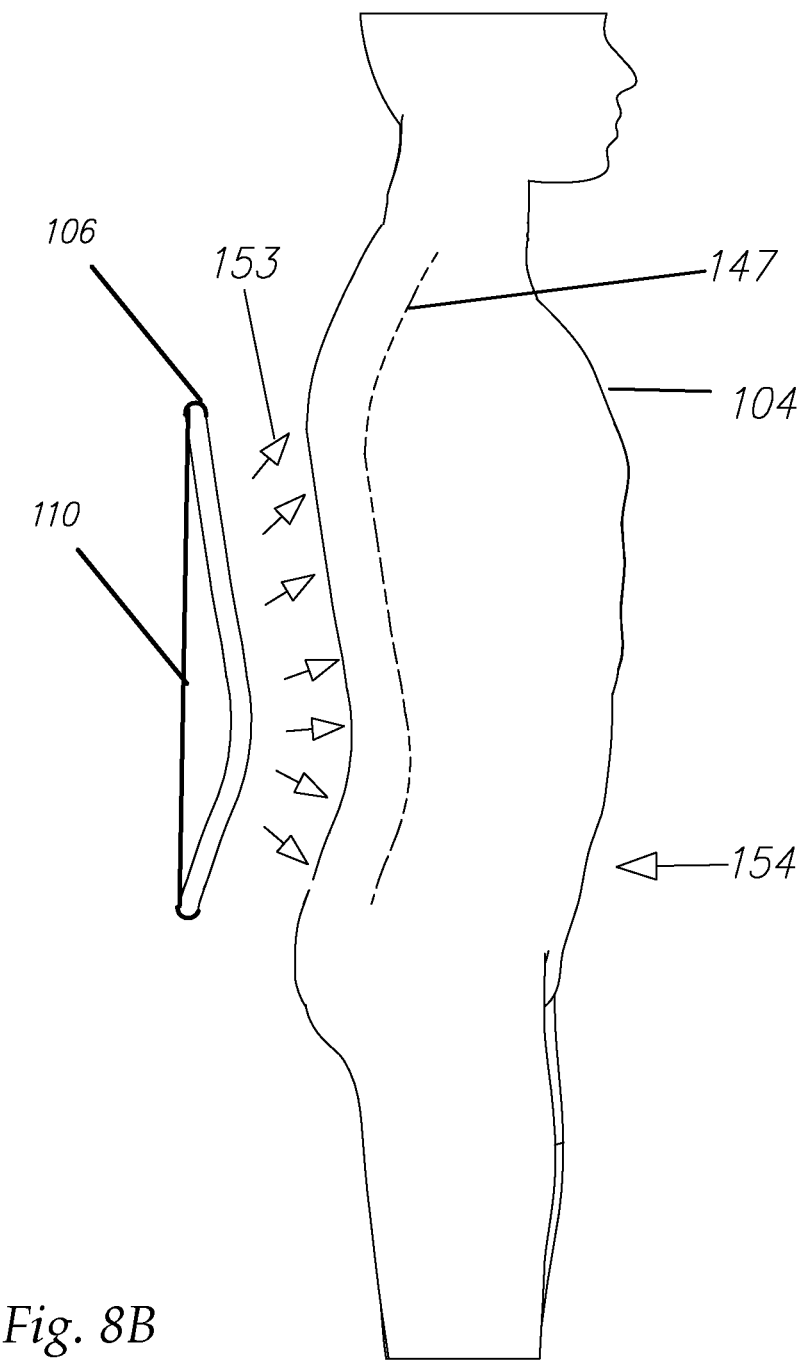
FIG. 8B shows a side view of person with normal posture with human interface device.

With reference to FIG. 8A and FIG. 8B, shown is a side view of a person with a normal posture 800, in accordance with one or more embodiments. In some embodiments, the normal posture 800 shown in FIG. 8A and FIG. 8B is considered a healthy posture of a person's spine 147, and may be referred to as "healthy posture." Depicted are sacral area 145, lumbar area 146, thoracic area 148, and cervical area 149 of the person. The healthy spine may be characterized by the concave shape of the lumbar area 146, convex curve of the thoracic area 148, and concave curve of cervical area 149, as shown in FIG. 8A. In some embodiments, the curvature of frame 106 is designed to fit the healthy posture such that human interface device 100 may align with the shape of the person's lower back 108 to maximize contact area with minimal deformation of fabric 110 or frame 106, shown in FIG. 8B. As such, human interface device 100 may reinforce a healthy posture of a person with normal posture 800. When worn by a person 104, the normal contact forces 153 imposed by fabric 110 and persons lower back 108 may help maintain the lordotic curve of the persons spine in its natural form.

Figure 9A:
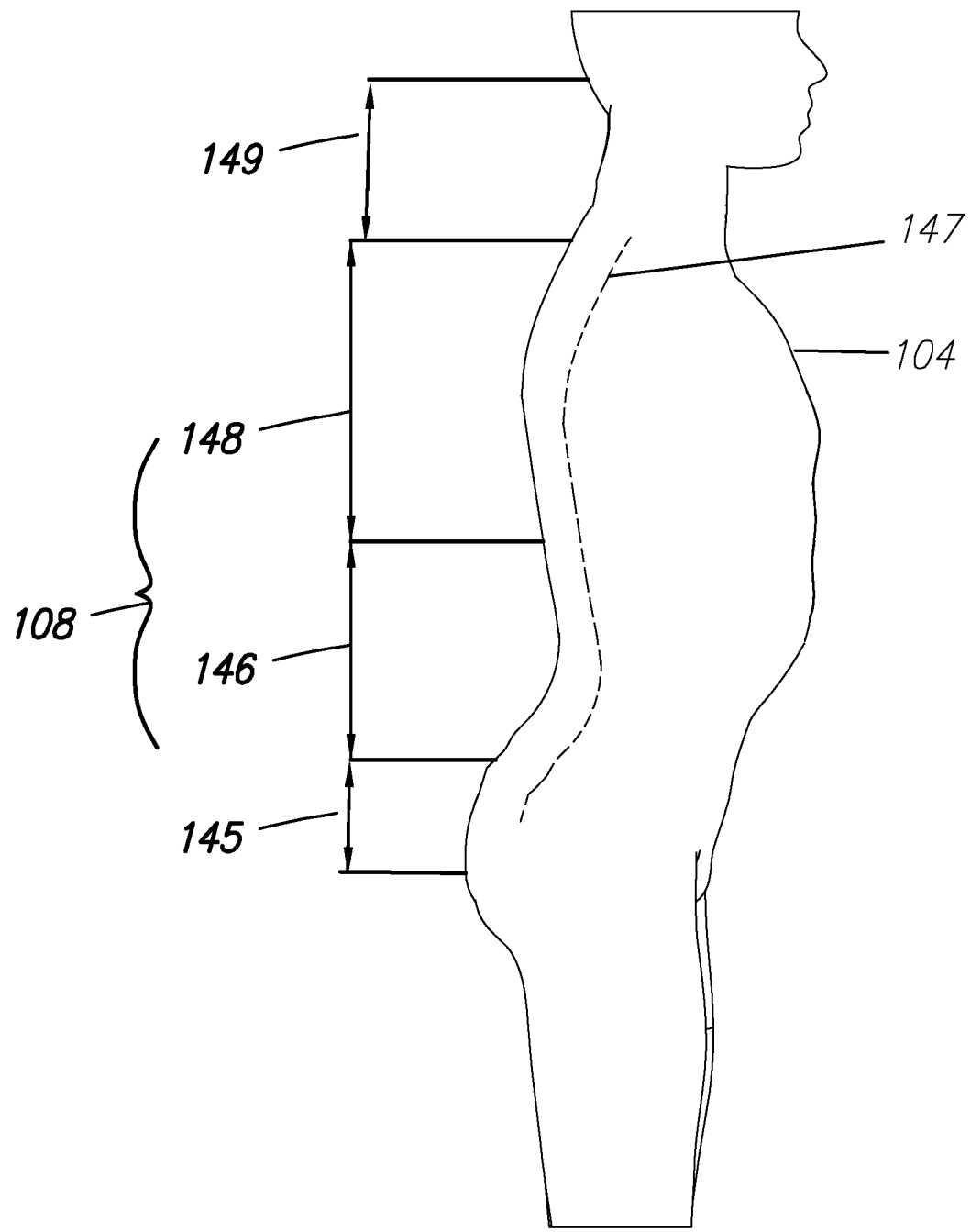
FIG. 9A shows a side view of person with hyperlordosis posture without human interface device.
Figure 9B:
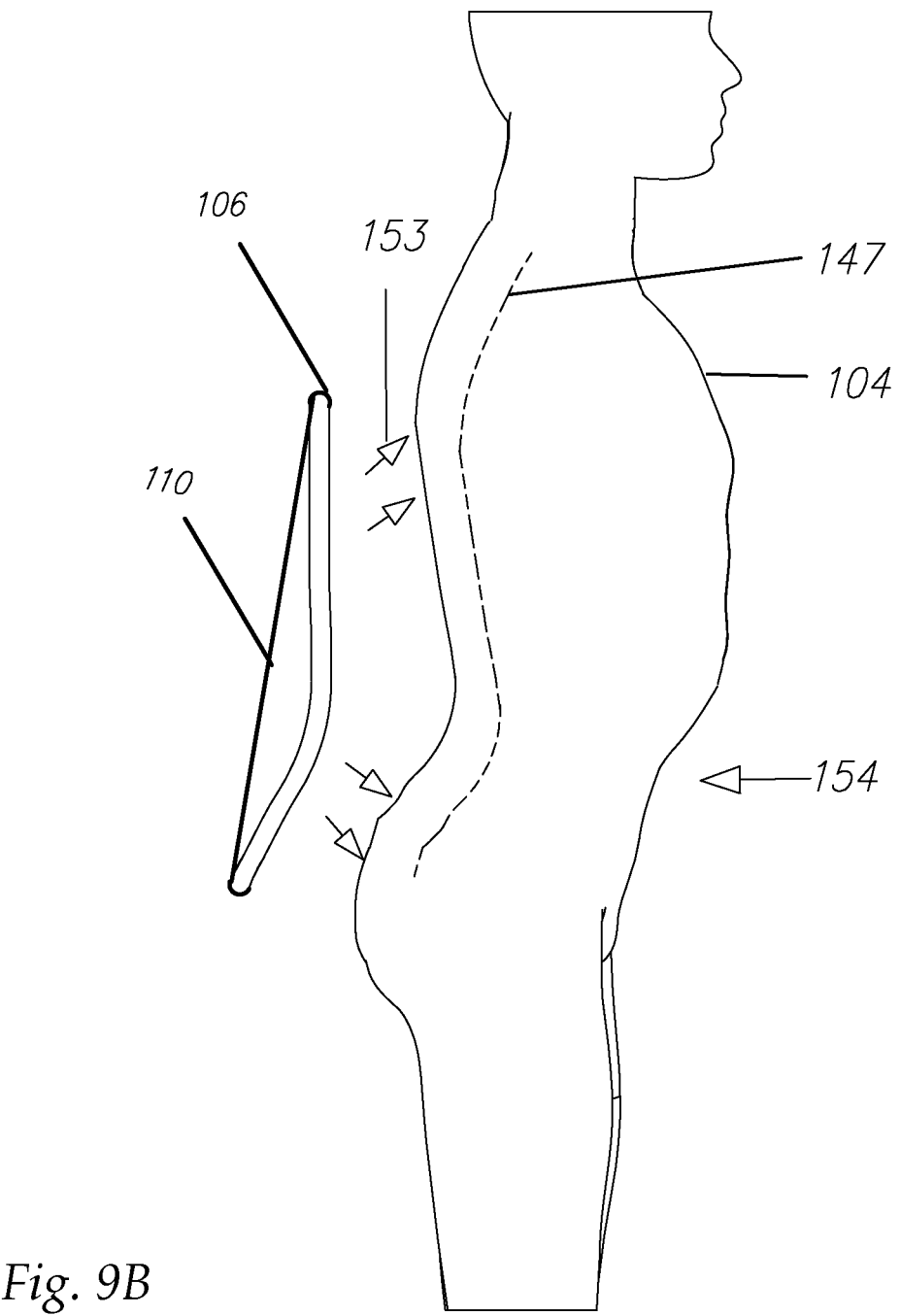
FIG. 9B shows a side view of person with hyperlordosis posture with human interface device.

Human interface device may also bias unhealthy posture when worn by a person with variations in posture or spine curvature, such as hyperlordosis. With reference to FIG. 9A and FIG. 9B, shown is a side view of a person with an example hyperlordotic posture 900, in accordance with one or more embodiments. The hyperlordotic posture 900, or hyperlordosis, shown in FIG. 9A and FIG. 9B is characterized by an excessive curve to the lumbar area 146. Hyperlordosis may result in excessive spinal compression forces, lower back pain, and instability. When human interface device 100 with frame 106 is worn by a person with hyperlordotic posture 900, normal contact forces 153 between the person's lower back 108 and human interface device 100 may be concentrated on the upper and lower sections of human interface device 100. The upper section of human interface device 100 may correspond to the upper portion of lumbar area 146 or lower portion of thoracic area 148, and the lower section of human interface device 100 may correspond to the lower portion of lumbar area 146 or sacral area 145. These normal contact forces 153 positioned above and below, but not at, the peak of the curve of the lumbar area 146, as shown in FIG. 9B, will bias the person's posture to reduce the lumbar curve to more closely resemble normal posture 800.

Figure 10A:
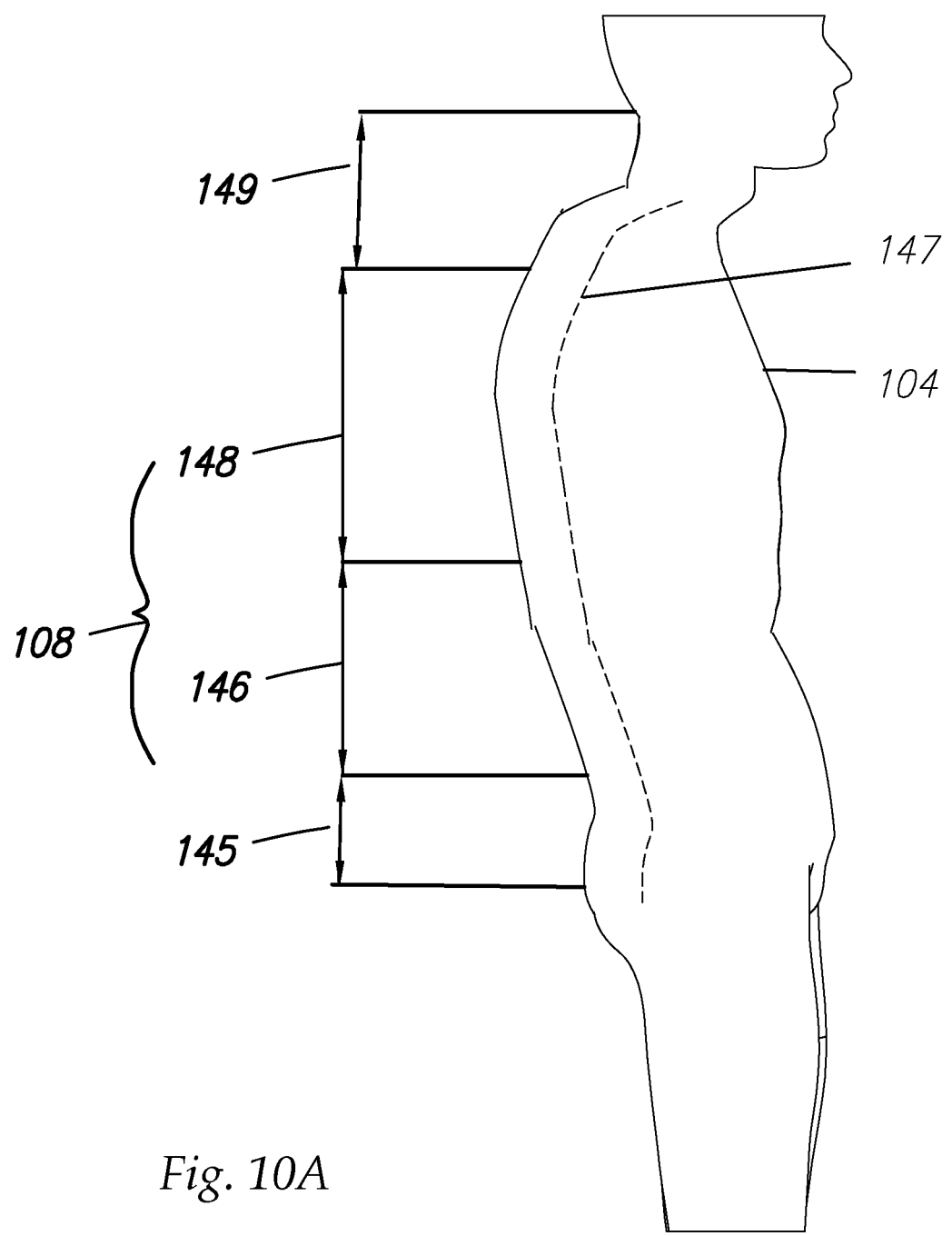
FIG. 10A shows a side view of person with hypolordosis posture without human interface device.
Figure 10B:
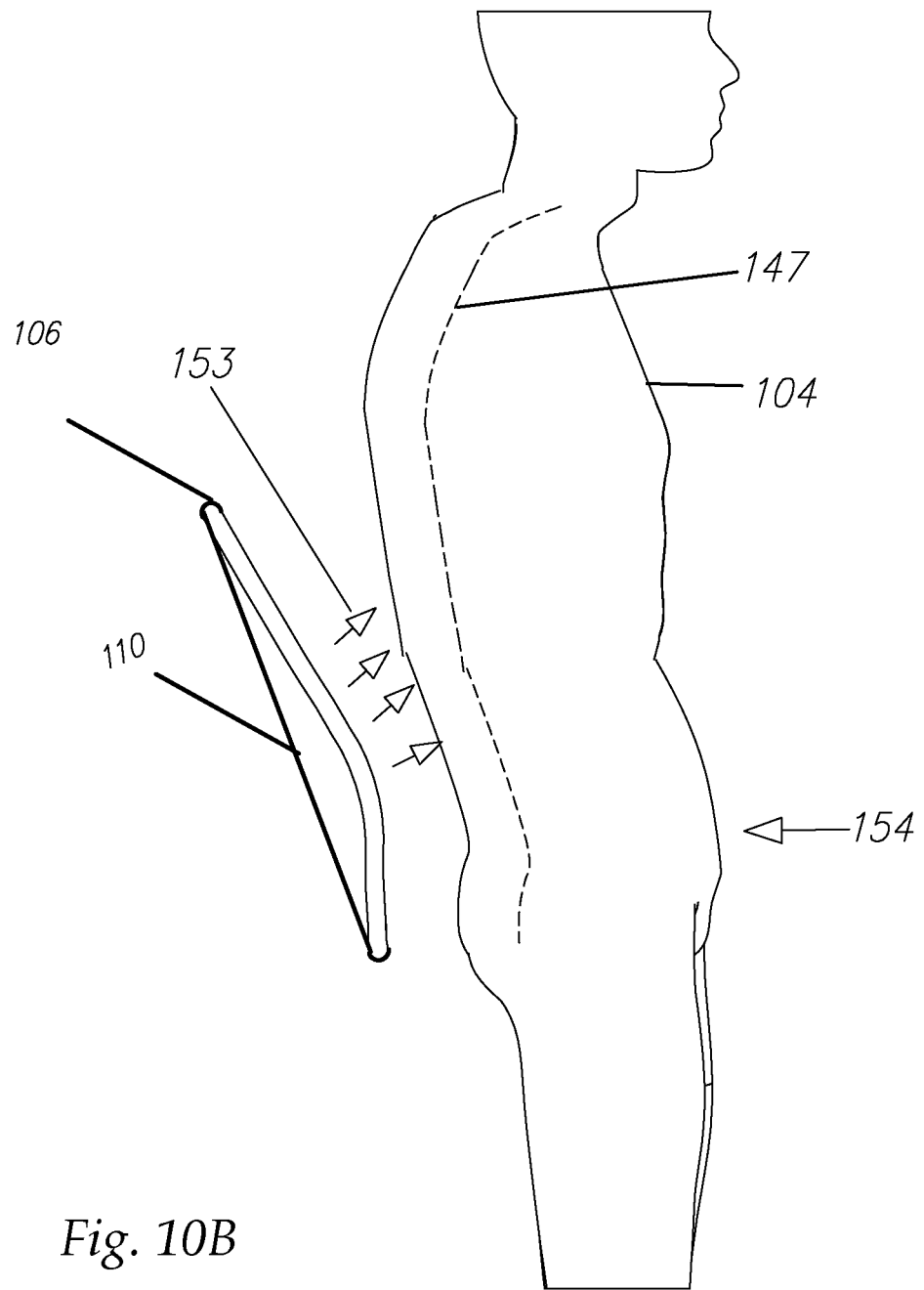
FIG. 10B shows a side view of person with hypolordosis posture with human interface device.

With reference to FIG. 10A and FIG. 10B, shown is a side view of a person with another example hypolordotic posture, in accordance with one or more embodiments. The hypolordotic posture shown in FIG. 10A and FIG. 10B is characterized by a loss of curvature to the lumbar area 146 that results in excessive curvature of the thoracic area 148 and cervical area 149. When human interface device 100 with frame 106 is worn by a person with hypolordotic posture, normal contact forces 153 between the person's lower back 108 and human interface device 100 may be concentrated on the middle section of human interface device 100, corresponding to the middle of lumbar area 146. These normal contact forces 153 positioned at the peak of the curve of the lumbar area 146, as shown in FIG. 10B, will bias the person's posture to increase the lumbar curve to more closely resemble normal posture 800.

The reinforcement of a healthy posture, or bias of unhealthy posture, may occur both when the person is standing straight, and when performing other postures such as bending backwards or forwards. Postural benefits may be achieved both during sedentary office work or dynamic industrial work.

In some embodiments, the vertical location of belt 118 relative to frame 106 may be adjustable to optimize properties of posture or load transfer. In some embodiments this may be to better align the curve of frame 106 with the person's lower back 108. In some embodiments this may be used to allow belt 118 to sit more comfortably relative to the person's stomach shape. For example, persons with belly fat may prefer a lower belt position that sits under the bulge of the stomach. In some embodiments this adjustment of belt 118 relative to frame 106 may be used to change the position of belt force 154, which may in turn alter the magnitude of normal contact forces 153.

In various embodiments, small openings in the fabric allows for air circulation. In some embodiments, fabric 110 is comprises a mesh, knit, woven, or knotted fabric of open texture exposing the persons lower back 108 to surrounding air allowing for air flow on persons lower back 108. Such mesh or interwoven or intertwined structure may allow for increased air circulation and help expose the persons lower back 108 to surrounding air allowing for air flow on persons lower back 108. In some embodiments, fabric 110 may comprise an elastic or non-elastic material to conform to or apply forces to the person's body. In some embodiments, fabric 110 may comprise a rigid or semi-rigid material to maintain a particular desired structural shape.

In some embodiments, frame 106 is made from metallic materials. In some embodiments, frame 106 is made from plastic materials. In some embodiments, frame 106 is made from carbon fiber or fiberglass materials or other composite materials. Frame 106 may comprise any component or combination of components or materials that include, without limitation, metal, plastic, aluminum, carbon fiber, fiberglass and any combination thereof. In some embodiments, frame 106 is made through an injection molding process. This list is meant to be informative without excluding other materials or combinations of materials which are capable of performing the indicated functions and providing desired structural characteristics in this specification.

In some embodiments, frame 106 is made from a semi rigid material that acts as a spring. The spring properties of the frame material may be used to allow the frame 106 to conform to the person's body and return to its original shape, to apply supportive forces to the person's body, or to facilitate movement of the person 104 within the human interface device 100. In some embodiments, frame 106 forms a loop and fabric 110 is under tensile stress in all directions. This tensile stress in all directions may allow the fabric 110 to create a normal contact force 153 when in contact with person 104.

Figure 11:
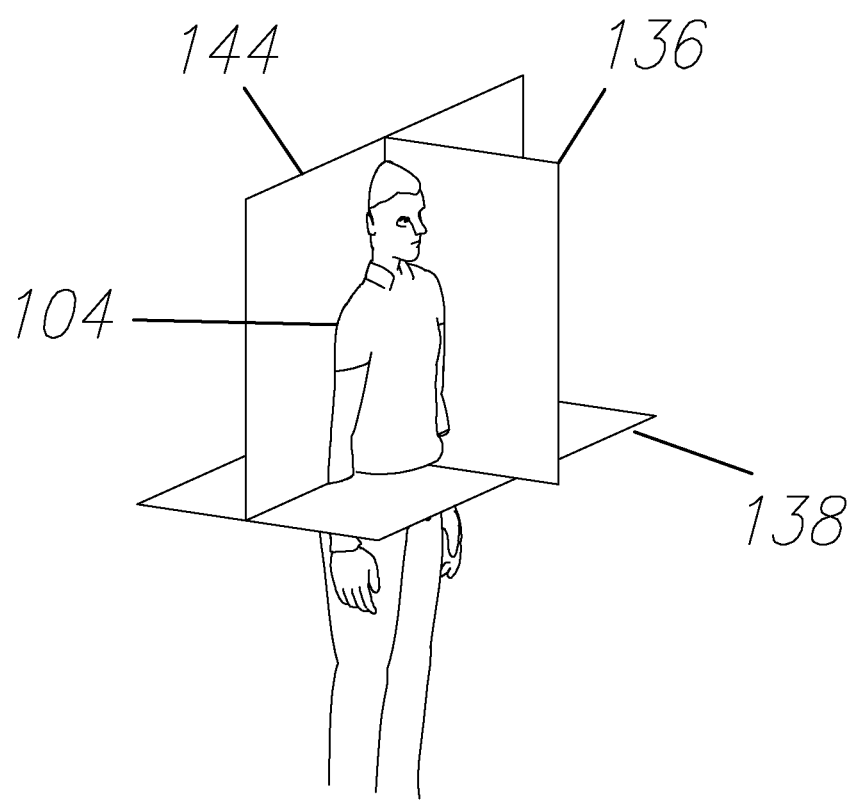
FIG. 11 shows the planes of person.

With reference to FIG. 11, shown are various planes of a human body, in accordance with one or more embodiments. The planes include sagittal plane 136, transverse plane 138, and coronal plane 144. In some embodiments the frame 106 of human interface device 100 is configured to conform the fabric 110 to the lordotic curve of the person's lower back 108 in the sagittal plane 136. In these embodiments, human interface device 100 may be used to support the shape of the wearer's lordotic curve to improve the person's posture. In some embodiments the frame 106 of human interface device 100 is configured to conform the fabric 110 to the lordotic curve of the person's lower back 108 in the transverse plane 138.

Figure 12:
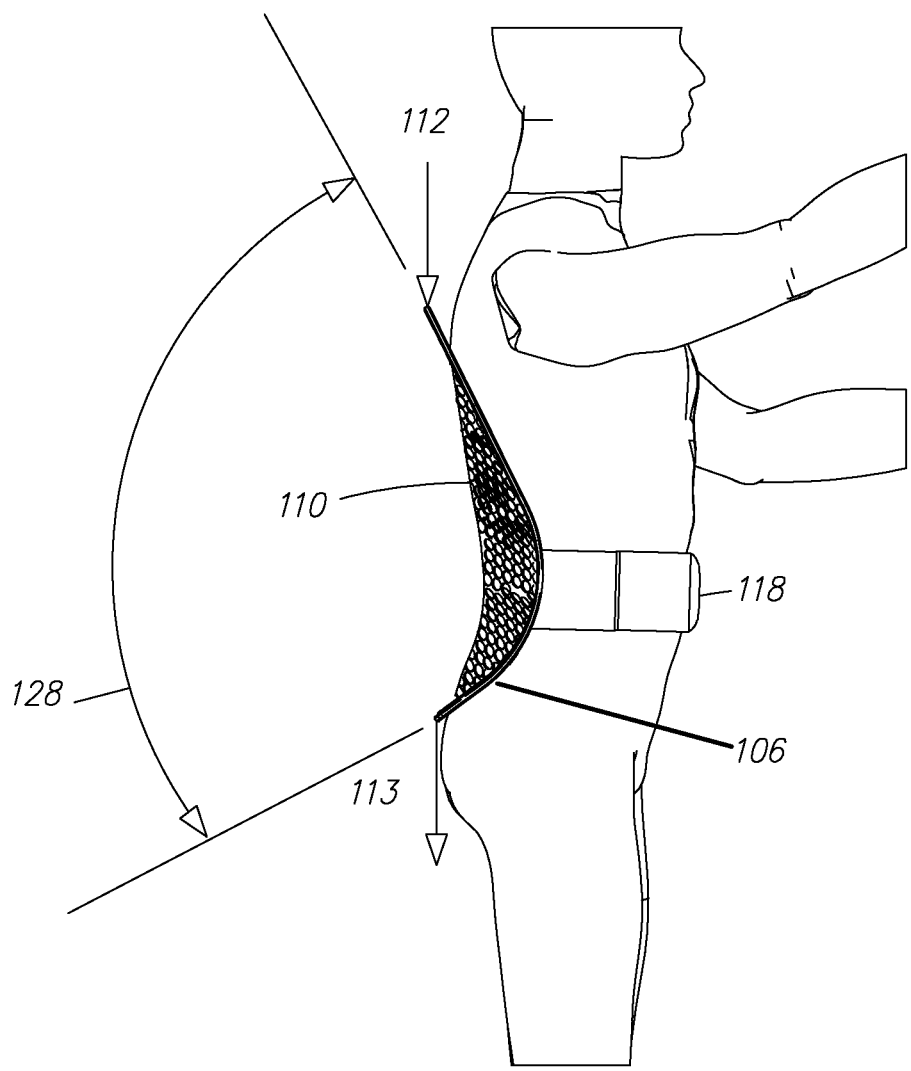
FIG. 12 shows a contour angle of human interface device.

Regardless of the materials used in construction of frame 106, it should be recognized by one of ordinary skill in the art that frame 106 may be configured to reduce, minimize, or eliminate deformation in the sagittal plane when under load weight 112. If frame 106 deforms or flexes under load weight 112, the shape of fabric 110 may also change accordingly. This change in fabric shape and geometry might impact the force distribution on the person's lower back 108. Therefore, it may be desirable to design frame 106 withstand load weight 112 and maintain its shape in the sagittal plane in the presence of load weight 112, so the contact area between fabric 110 and person 104 is undisturbed. With reference to FIG. 12, shown is a side view of an example human interface device 100 depicting a contour angle 128 along the sagittal plane 136, in accordance with one or more embodiments. As described, frame 106 should be configured to ensure contour angle 128 does not changing in the presence of vertical load weight 112.

Figure 13:
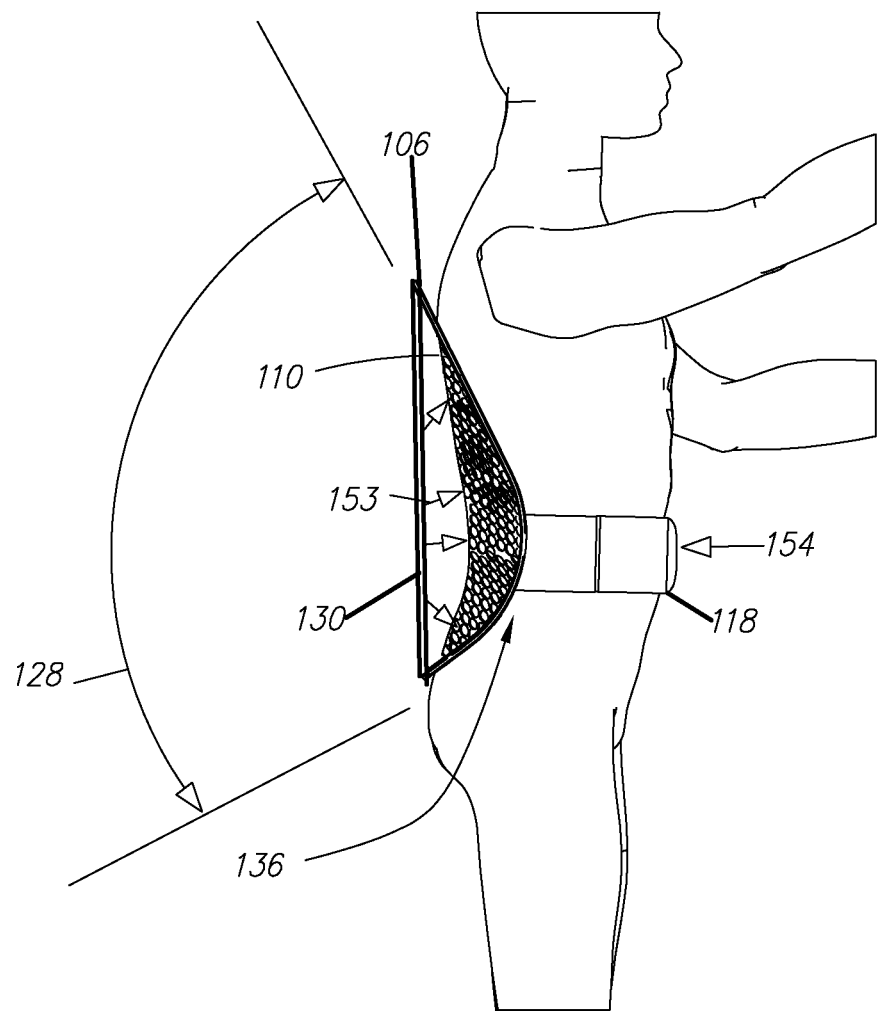
FIG. 13 shows an embodiment of human interface device with a contour adjustment element.

In addition to preventing deformation of frame 106 under load weight 112, deformation of frame 106 under normal contact forces 153 should also be prevented in various embodiments. When worn by a person, normal contact forces 153 caused by belt force 154 may cause contour angle 128 in the sagittal plane to increase. To prevent this, in some embodiments, the human interface device further comprises a contour adjustment element 130. With reference to FIG. 13, shown is a side view of an example human interface device 100 with a contour adjustment element 130, in accordance with one or more embodiments. In various embodiments, contour adjustment element 130 spans across frame 106 and applies a tensile force between two ends of frame 106. In some embodiments, the tensile force is applied between the upper and lower edges of frame 106. In some embodiments, tensile force may be applied between the side edges 107 and 109 of frame 106. The tensile force applied may prevent expansion (increase), or other deformation, of contour angle 128 in the sagittal plane. Thus, contour adjustment element 130 may function as a load bearing structure, as will be further described below. The contour adjustment element 130 may also adjust the tension force to alter contour angle 128 to a desired configuration or position.

The implementation of contour adjustment element 130 may also alter the fit of the frame contour with the person's lower back 108. This may allow human interface device 100 to accommodate a particular person's back, which may vary in alignment, shape, or measurement between persons. In some embodiments, contour adjustment element 130 may comprise a strap attached to the top and bottom edges of frame 106. In some embodiment, contour adjustment element 130 may be incorporated into load bearing structure 122, as will be further described below with reference to FIG. 19 which illustrates a back-perspective view of a vertical load bearing structure 122 attached to an example human interface device, in accordance with one or more embodiments. In such embodiment, changing the length of the strap changes the tension force between the two ends of the frame. In other embodiments, contour adjustment element 130 comprises a mechanical rod or spine where the bottom edge of frame 106 is fixed on the rod, while the top edge of the frame can be moved along the rod and fixed in a desired location to adjust the shape, and contour angle 128, of the frame. This may create a tensile force between the two ends of frame 106.

In some embodiments, human interface device 100 is configured to conform to the person's lower back 108 in the transverse plane 138 (shown in FIG. 11). To ensure frame 106 can be used by individuals with trunks or lower backs of various widths and shapes, frame 106 may be compliant in the transverse plane 138 in response to tensile force due to tightening of belt 118. As seen FIG. 19, belt 118 is coupled to frame 106 in at least two side-edges 107 and 109. In other words, variations in belt force 154 applied by belt 118 should at least partially deform frame 106 such that frame 106 is able to wrap around the lower back of person 104. Thus, frame 106 may be configured to be compliant in the transverse plane 138 while remaining rigid in the sagittal plane 136.

Figure 14:
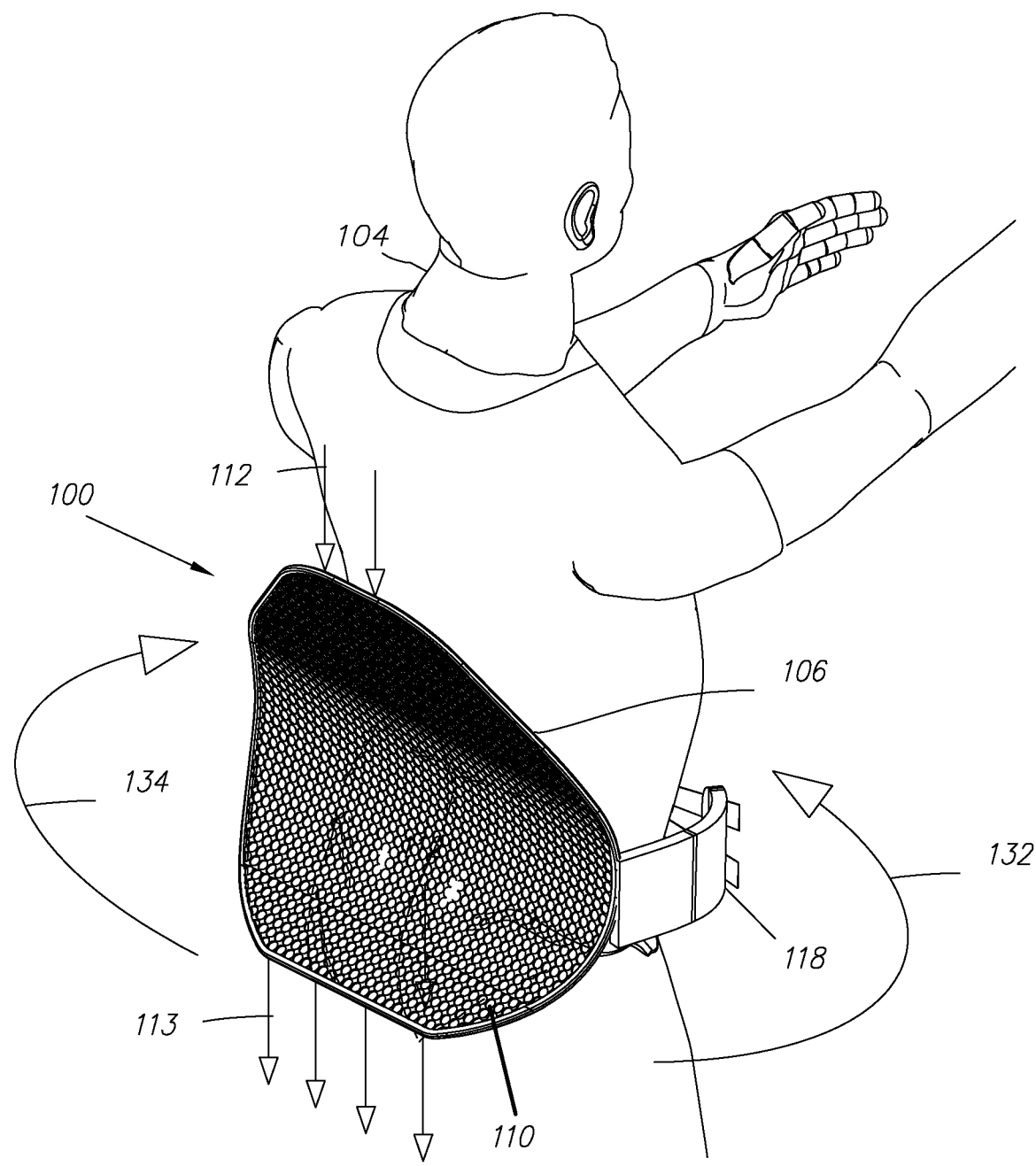
FIG. 14 shows the human interface device flexing in the transverse plane.

With reference to FIG. 14, shown is a perspective view of an example human interface device depicting flexing of the frame in the transverse plane, in accordance with one or more embodiments. As shown in FIG. 14, frame 106 is stretched along frame deformation arrows 132 and 134 in response to tightening force 154 of belt 118. This property of frame 106 may allow human interface device 100 to be used by different individuals with various widths and shapes.

To provide rigidity in sagittal plane 136, frame 106 may be constructed with proper geometry and materials to remain resistant in the sagittal plane 136 in response to load weight 112. To provide compliancy in transverse plane 138, frame 106 may be constructed with proper geometry and materials to stay compliant in the transverse plane 138 in response to tensile forces along frame deformation arrows 132 and 134 from belt 118. Among other methods, this may be achieved through a frame 106 or load bearing structure 122 that is shaped to resist bending in the vertical plane but not the horizontal plane. One example is through varying horizontal thicknesses compared to vertical thicknesses of frame 106. Frame 106 with thickness in the sagittal plane 136 substantially greater than its thickness in the transverse plane 138 may be unitary in construction or comprised of multiple pieces. One of skill in the art may appreciate that the compliancy of frame 106 in the transverse plane 138 to conform to the shape of person 104 may similarly be achieved by a bendable structure that maintains its shape once deformed, a resilient structure that returns to its original shape once forces are removed, or a flexible structure that neither maintains its shape or returns to its original shape once forces are removed but instead continues to deform freely under its own weight and inertia. In some embodiments frame 106 is made of a bendable material that in response to tensile forces from belt 118 conforms to the shape of person 104 and maintains its shape until additional forces are applied. In some embodiments frame 106 is made of a resilient material that in response to tensile force from belt 118 conforms to the shape of person 104 and returns to its original shape once belt 118 is released and the tensile forces are no longer applied. Still in other embodiments frame 106 is made of a flexible material that in response to tensile force from belt 118 conforms to the shape of person 104 and once belt 118 is released and tensile forces are no longer applied, frame 106 neither returns to its original shape nor continues to conform to person 104. In other embodiments, frame 106 may be made of multiple rigid segments attached together through joints or similar flexible connections to achieve compliancy, flexibility, resiliency, or bendability in the transverse plane 138. In some embodiments the structure of frame 106 in the transverse plane wraps around the lower back 108 and hips of person 104. In other embodiments the structure of frame 106 in the transverse plane completely encircles person 104. Still in other embodiments the structure of frame 106 in the transverse plane only partially encircles the lower back 108 of person 104.

In some embodiments, human interface device 100 may further comprise an upper torso coupling that may serve to further secure the frame 106 to the person's upper torso or lower back 108 causing more effective contact between fabric 110 and person 104. The upper torso coupling may further facilitate load transfer or posture maintenance. Such upper torso coupling may comprise various configurations of straps which may exert vertical forces, horizontal forces, or a combination thereof. Vertical forces exerted by the straps on a person's shoulders may assist with supporting a vertical load. Horizontal forces exerted by the straps on the person's shoulders or chest may further secure the human interface device to the person's lower back to maximize normal contact forces 153 or friction forces 152, or further stabilize human interface device 100 on the person's torso. The upper torso couplings may be attached to frame 106, belt 118, or load bearing structure 122.

Figure 15:
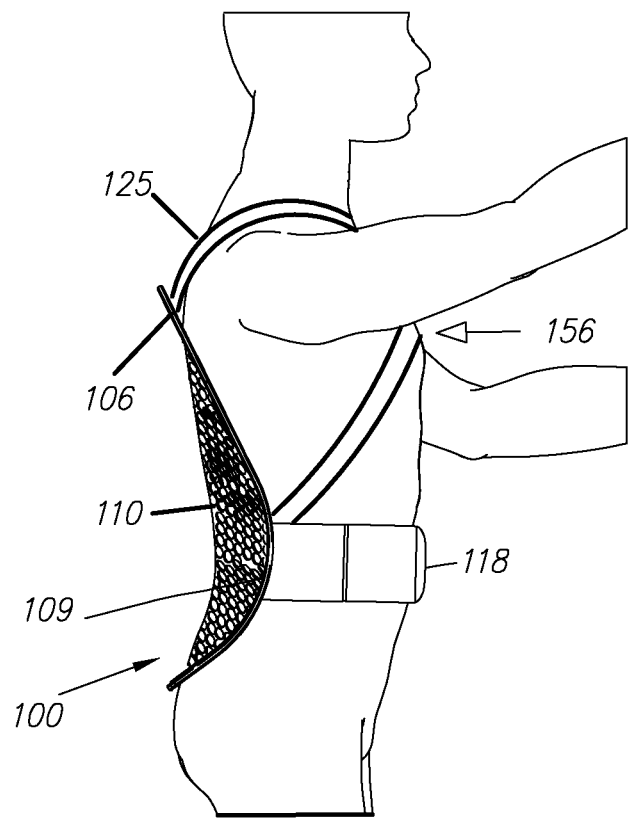
FIG. 15 shows an embodiment of human interface device with shoulder straps.
Figure 16:
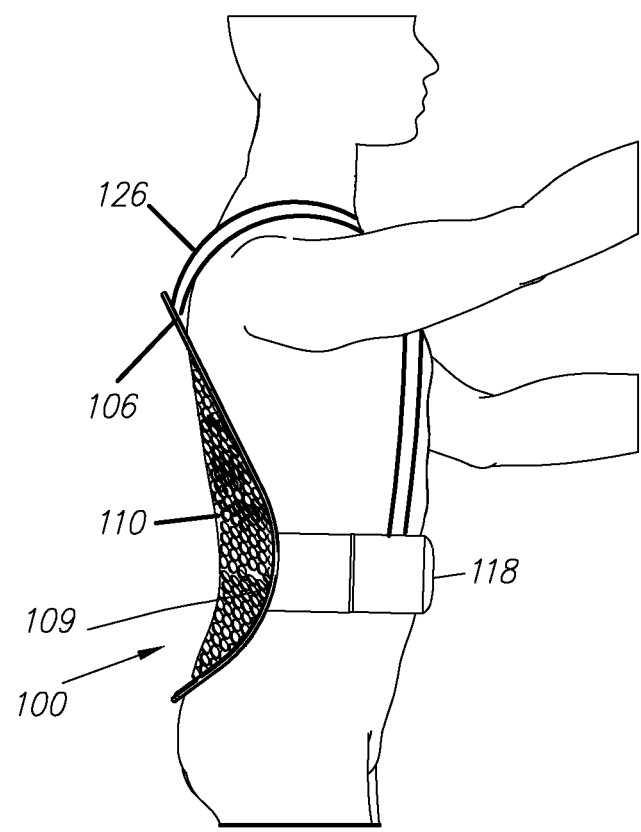
FIG. 16 shows an embodiment of human interface device with suspender straps.

FIG. 15, FIG. 16, FIG. 17, and FIG. 18 illustrate various embodiments of upper torso coupling configurations implemented on an example human interface device, in accordance with one or more embodiments. In some embodiments upper torso couplings facilitate more effective contact between the fabric 110 and person 104. In some embodiments, the upper torso coupling may consist of a pair of shoulder straps 125. FIG. 15 depicts an upper torso coupling comprising a pair of shoulder strap 125 that each partially encircle a shoulder of the person and may be connected together through a sternum strap across the chest. Shoulder strap 125 may be attached to frame 106 at a lower edge of side edge (107 or 109) from one end and to the upper edge of frame 106 or a higher portion of a side edge (107 or 109) from a second end wherein when the shoulder straps 125 are worn by the person 104, tightening of the shoulder straps 125 causes more effective contact between the fabric 110 and the person 104. In another embodiment, shoulder straps 125 may support some of a load weight 112 placed on the frame 106. In some embodiments, shoulder straps 125 are coupled to the upper edge of frame 106 from a first end and to belt 118 from a second end. FIG. 16 depicts an upper torso coupling comprising a pair of suspender straps 126 that each partially encircles a person's shoulders. Each suspender strap 126 may be attached to belt 118 at one end and to frame 106 at the top edge or a portion of a side edge (107 or 109).

Figure 17:
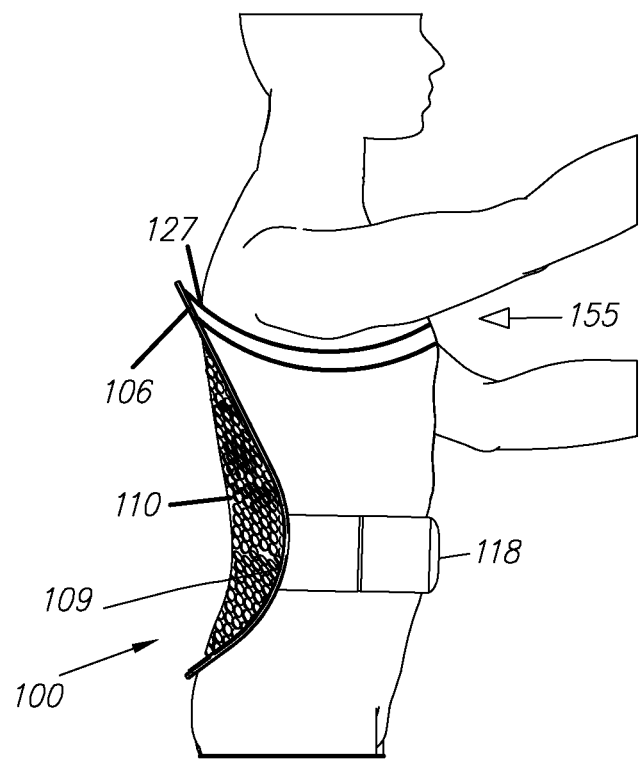
FIG. 17 shows an embodiment of human interface device with a chest strap.

FIG. 17 depicts an upper torso coupling comprising chest strap 127 that is configured to encircle the person's chest. Chest strap 127 may be coupled to frame 106 from both sides wherein when person 104 wears the human interface device 100, chest strap 127 pushes persons chest posteriorly causing more effective contact between fabric 110 and person 104. Posteriorly may be defined as pointing towards the rear side of person in the direction of upper torso extending force 155. In some embodiments, each end of chest strap 127 may be attached to frame 106 along the top edge. In some embodiments, one end of chest strap 127 may be attached to side edge 107 and the other end of chest strap 127 may be attached to side edge 109. In various embodiments, the upper torso coupling comprises an elastic material to create an upper torso extending force 155 that pushes person's chest posteriorly, as shown in FIG. 17 with chest strap 127 causing more effective contact between the fabric 110 and the person 104. Upper torso extending force 155 allows a person's spine to flex forward but with increasing flexion biases the spine back to a neutral position. Upper torso extending force 155 may prevent person 104 from slouching forward or prevent the rounding of the thoracic area 148 of the person's spine 147 shown in FIG. 10. In some embodiments, human interface device 100 is configured to be coupled to the trunk of a person 104 to support person's posture. Human interface device 100 may comprise a frame 106, fabric 110 coupled to frame 106 and configured to be under tensile forces, a belt 118 coupled to two side edges of frame 106 configured to attach to the hips of person 104, and an upper torso coupling configured to secure the frame 106 to the persons upper torso. When human interface device 100 is worn by person 104, the fabric 110 imposes a normal contact forces 153 to person's lower back 108 to support the lordotic curve of person's spine 147 and the upper torso coupling exerts an upper torso extending force 155 to help keep person's thoracic area 148 of the spine 147 in a natural position.

Figure 18:
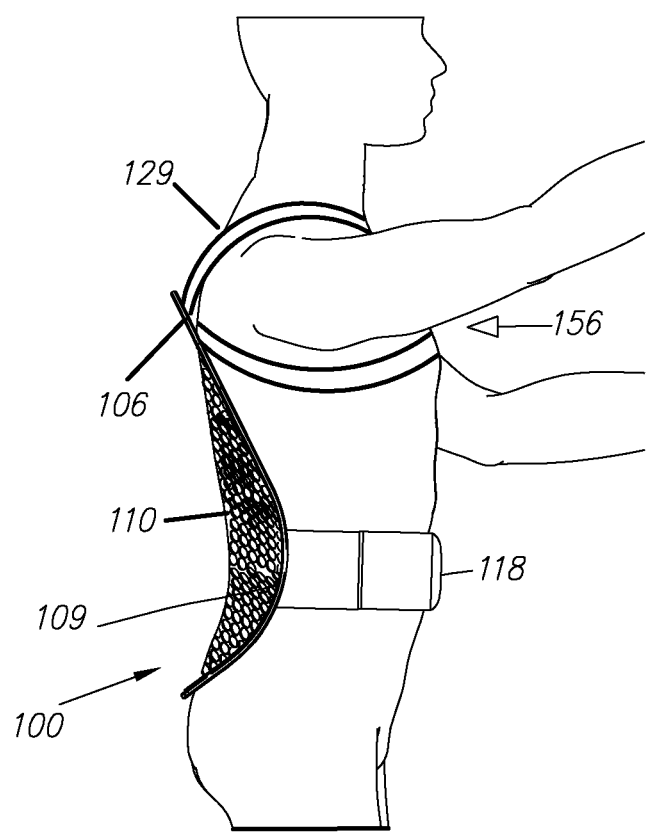
FIG. 18 shows an embodiment of human interface device with scapula straps.

FIG. 18 depicts an upper torso coupling comprising scapula strap 129 that may near fully encircles a person's shoulders. In some embodiments, scapula strap 129 may be attached to the top edge or side edges of frame 106. In some embodiments, scapula strap 129 comprises two straps, with each strap coupled to one side of frame 106 and encircling the corresponding shoulder. In some embodiments, scapula strap 129 may comprise a first strap which is attached to side edge 109 of frame 106, and is positioned under the right arm of the person, across the chest, and over the left shoulder, and is attached to the opposite side edge 107. In some embodiments, scapula strap 129 may comprise a second strap which is attached to side edge 107, and is positioned under the left arm of the person, across the chest, and over the right shoulder, and is attached to side edge 109. In some embodiments the upper torso coupling comprises an elastic material to create a scapula retracting force 156 that pushes the person's shoulder complex posteriorly, as shown in FIG. 18 with scapula strap 129. Scapula retracting force 156 may similarly affect movement of upper torso flexion or extension. Scapula retracting force 156 may be used to prevent forward rounding of the shoulders or the thoracic area 148 of the person's spine 147. This may be valuable in office work when workers are typically hunched over a desk. In some embodiments, human interface device 100 is configured to be coupled to the trunk of a person 104 to support person's posture. Human interface device 100 may comprise a frame 106, fabric 110 coupled to fame 106 and configured to be under tensile forces, a belt 118 coupled to two side edges of frame 106 configured to attach to the hips of person 104, and an upper torso coupling configured to secure the frame 106 to the persons upper torso. When human interface device 100 is worn by person 104, the fabric 110 imposes a normal contact forces 153 to person's lower back 108 to support the lordotic curve of person's spine 147 and the upper torso coupling exerts a scapula retracting force 156 to help keep person's thoracic area 148 of the spine 147 in a natural position or to prevent person 104 from rounding the shoulders forward.

As explained above, one of the important characteristics of frame 106 is to provide tensile forces on fabric 110. Another property of frame 106 is to transfer the load weight 112 to fabric 110 without deforming and changing its own geometry along in the sagittal plane 136. If frame 106 changes its form or bends in response to vertical load weight 112, then the shape of fabric 110 may also change and affect the load distribution on the back of person 104. Thus, it may be important to ensure that frame 106 is rigid and does not deform in response to load weight 112 in sagittal plane.

One way to ensure that frame 106 will not deform and will not change its geometry in response to the force of vertical load weight 112, is to provide a rigid load bearing structure that couples to frame 106. FIG. 19, FIG. 20, FIG. 21, and FIG. 22 illustrate an example human interface device implementing a vertical load bearing structure 122, in accordance with one or more embodiments. In some embodiments, human interface device 100 may further comprise load bearing structure 122 configured to hold or support a load applying load weight 112 to the human interface device. The load bearing structure is coupled to the frame such that load bearing structure 122 transfers a portion of load weight 112 to the frame. In some embodiments, load bearing structure 122 is configurable to be coupled to frame 106 and rigid enough to ensure that frame 106 does not deform or change its shape in the sagittal plane in response to load weight 112. Human interface device 100 may be configured to support multiple types of load that create load weight 112. In one embodiment human interface device 100 is configured to support the load weight 112 of a backpack or carrier for a person, either a child or an adult, coupled to human interface device 100 when worn by person 104. In another embodiment, human interface device 100 is configured to support the load weight 112 of body armor coupled to human interface device 100. The body armor may be distributed across the chest, back, arms, legs, or head of person 104. In another embodiment human interface device 100 is configured to support the load weight 112 of a heavy object such as a camera, tool, or shield carried by person 104. The heavy object may be coupled to a shoulder or elbow supporting exoskeleton, a set of suspension cables, or by a multi-linkage support segment that is coupled to human interface device 100. The shoulder exoskeleton, elbow exoskeleton, multi linkage support segment or suspension cables may be spring loaded in the vertical direction to support the weight of the heavy object and free in the horizontal direction to allow the person 104 to position the heavy object. Alternatively, the shoulder exoskeleton, elbow exoskeleton, multi linkage support segment or suspension cables may be rigid in the vertical direction to support the full load of the heavy object and apply it to human interface device 100. In other embodiments human interface device 100 is configured to support the load weight 112 of an exoskeleton system coupled to human interface device 100, either due to the weight of the exoskeleton or the support created by the exoskeleton and applied to the person 104.

Figure 19:
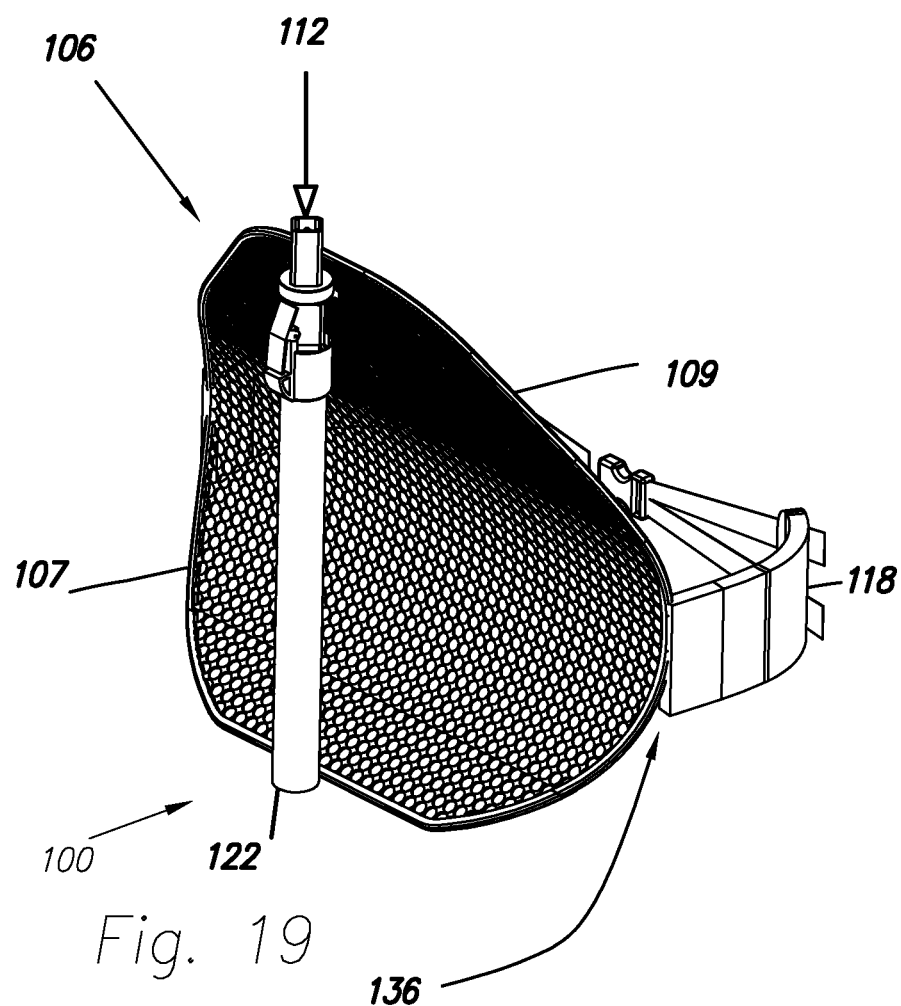
FIG. 19 shows an embodiment of human interface device with a load bearing structure.
Figure 20:
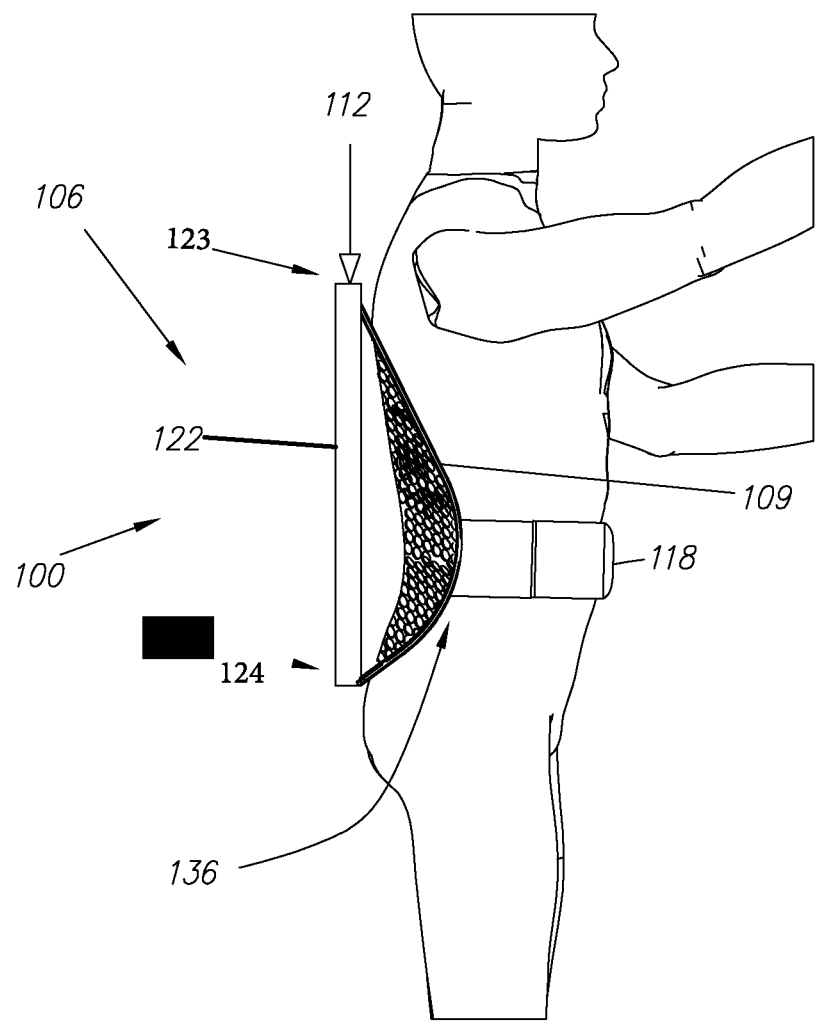
FIG. 20 shows a side view of human interface device with load bearing structure worn by a person.
Figure 21:
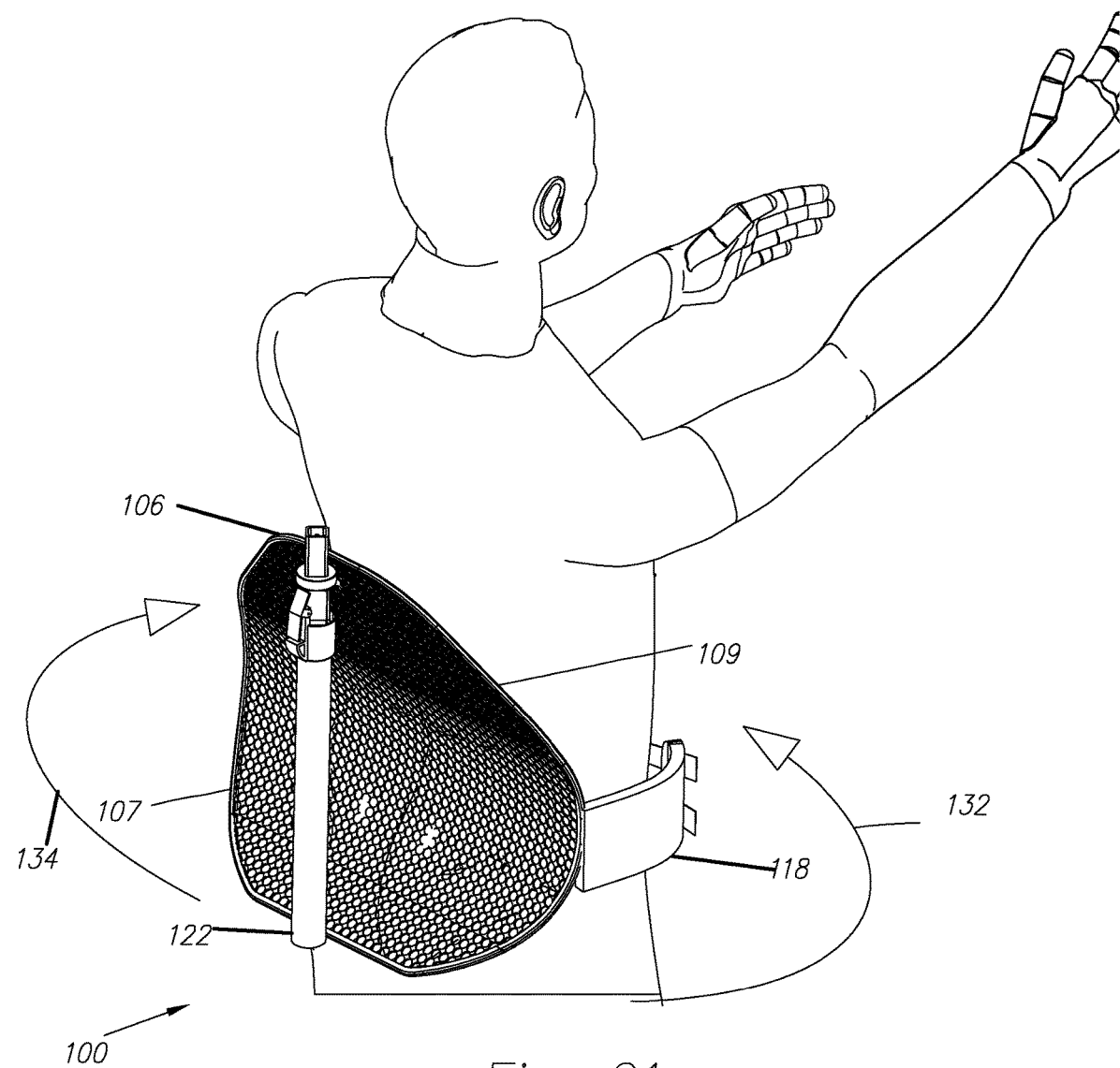
FIG. 21 shows human interface device with load bearing structure flexing in the transverse plane.

As shown in FIG. 19, FIG. 20, and FIG. 21, in some embodiments, load bearing structure 122 is vertical and has a cylindrical shape. In some, embodiments load bearing structure 122 comprises one or a plurality of sections configured to slide into or over one another allowing for adjustment of the load bearing structure 122 length or the position of the load coupling point to the load bearing structure 122. In some embodiments the plurality of sections are arranged concentrically. In some embodiments, load bearing structure 122 comprises one or a plurality of concentric sections configured to slide into one another allowing for adjustment of the load coupling to the strut 142. FIG. 20 illustrates a side view of the interface device depicting load bearing structure 122 coupled to frame 106 on two coupling locations 124 and 123 and maintains the shape of frame 106 in the sagittal plane 136 in response to load weight 112. In some embodiments the rigidity of the load bearing structure 122 prevents frame 106 from deforming in the sagittal plane 136. The coupling between load bearing structure 122 and frame 106 may be adjustable to alter the curvature of frame 106 in the sagittal plane.

Figure 22:
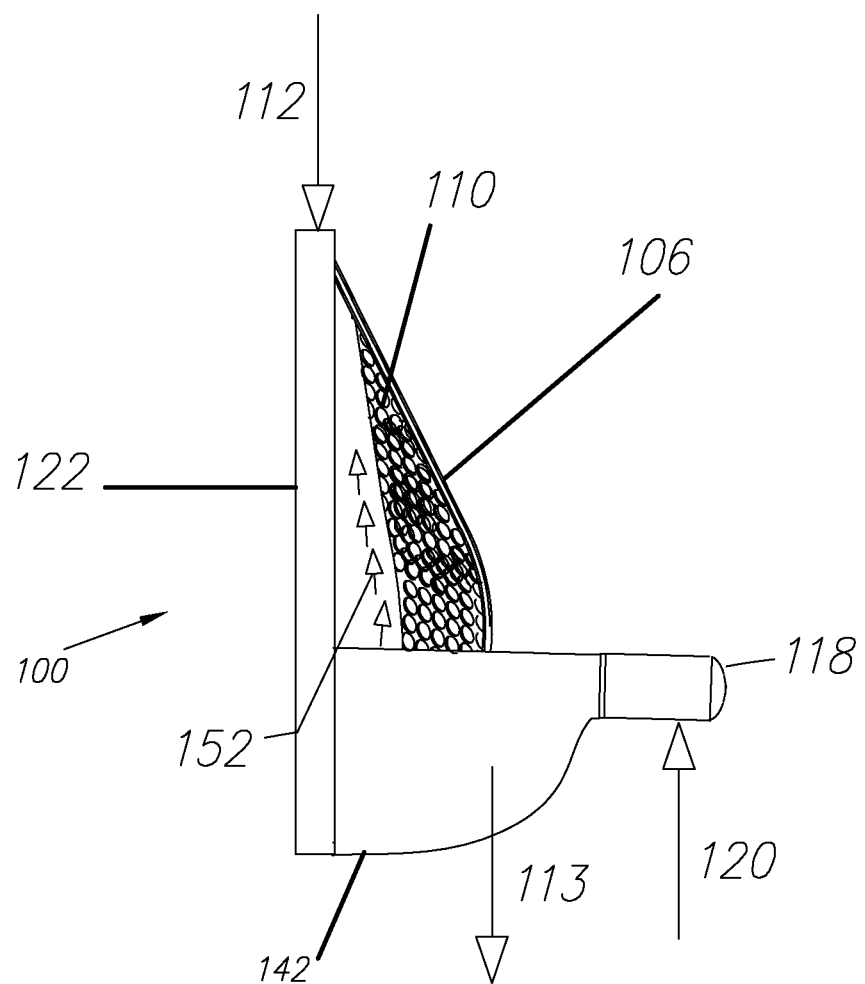
FIG. 22 shows an embodiment of human interface device with a strut.

FIG. 21 shows a back-perspective view of load bearing structure 122 that allows frame to bend in the transverse plane. Such load bearing structure 122 may transfer load weight 112 and allow bending motion along frame deformation arrows 132 and 134 in the transverse plane 138. In some embodiments, load bearing structure 122 allows frame 106 to bend in the transverse plane 138 to better conform to the person's back. FIG. 21 shows how a vertical load bearing structure 122 allows frame 106 to bend in the transverse plane 138 as it minimally contacts frame 106 along the horizontal axes and does not restrict the movement of frame along frame deformation arrows 132 and 134. In the embodiment shown in FIG. 21, load bearing structure 122 is positioned behind person 104 and is coupled to frame 106 at two locations. In some embodiments, compliancy of load bearing structure 122 or tool holder 142 in the transverse plane 138 may serve to allow a spring loaded spinal twist motion of person 104 when wearing human interface device 100. FIG. 22 is a side view of another example vertical load bearing structure. As shown in FIG. 22, in some embodiments, load bearing structure 122 comprises a strut 142, configurable to support load weight 112 and is coupled to frame 106 in at least two locations of frame 106. In some embodiments, strut 142 may function as a tool holder, further described below with reference to FIG. 23 and FIG. 24. The terms tool holder and strut 142 may be used interchangeably. Load bearing structure 122 is configurable to hold load weight 112 and is coupled to frame 106 and transfers at least a portion of the load weight 112 to frame 106 and eventually to fabric 110. In some embodiments, the load weight is distributed on a variety of locations on the person. For example, a construction worker's tool belt may require support load weight at multiple locations around the person. Lower edge of frame 106 may be used to hang tools, but one must ensure load weight 113 on the lower edge of frame 106, as shown in FIG. 22, does not deform frame 106.

Figure 23:
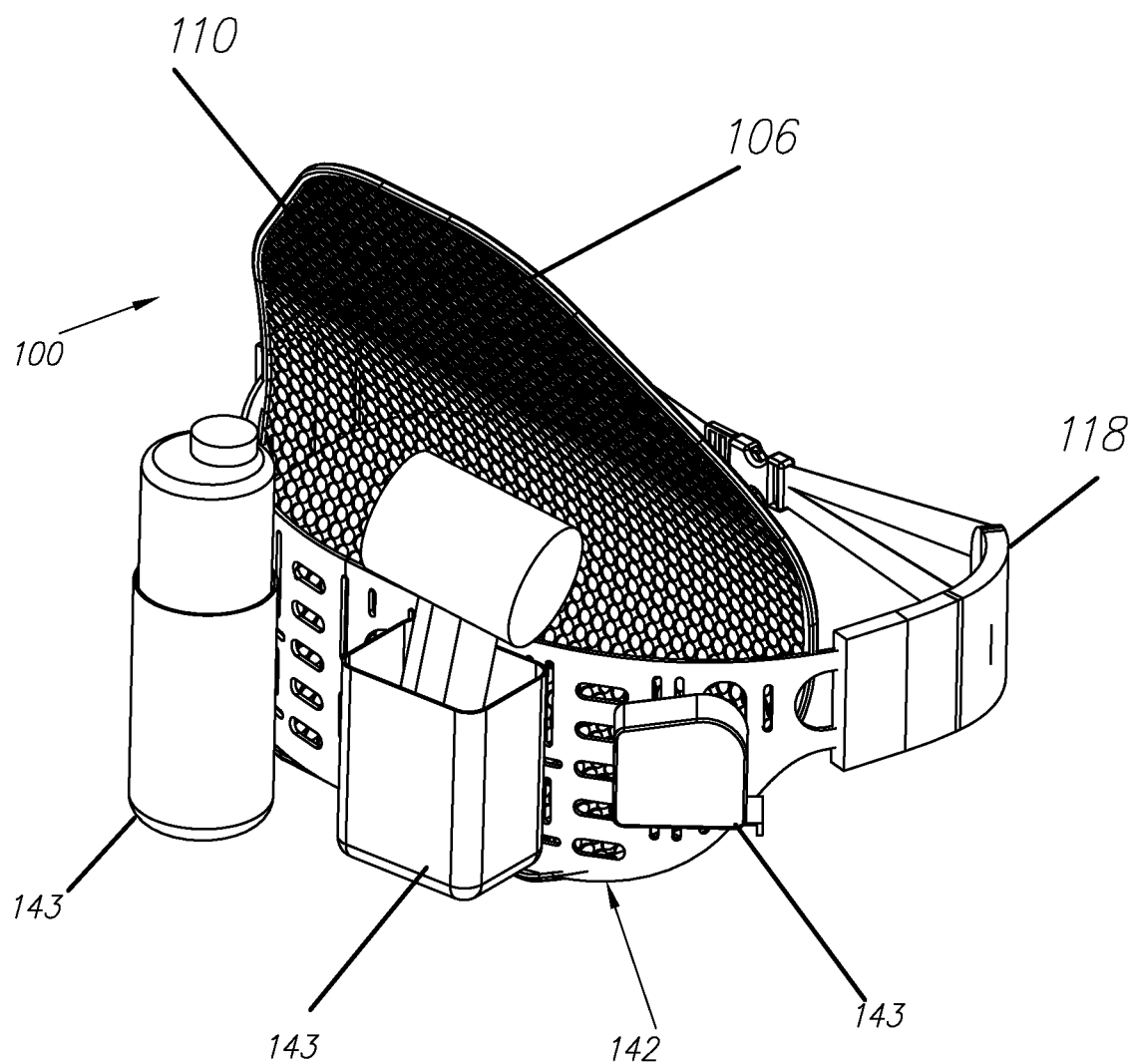
FIG. 23 shows an embodiment of human interface device with a toolholder.
Figure 24:
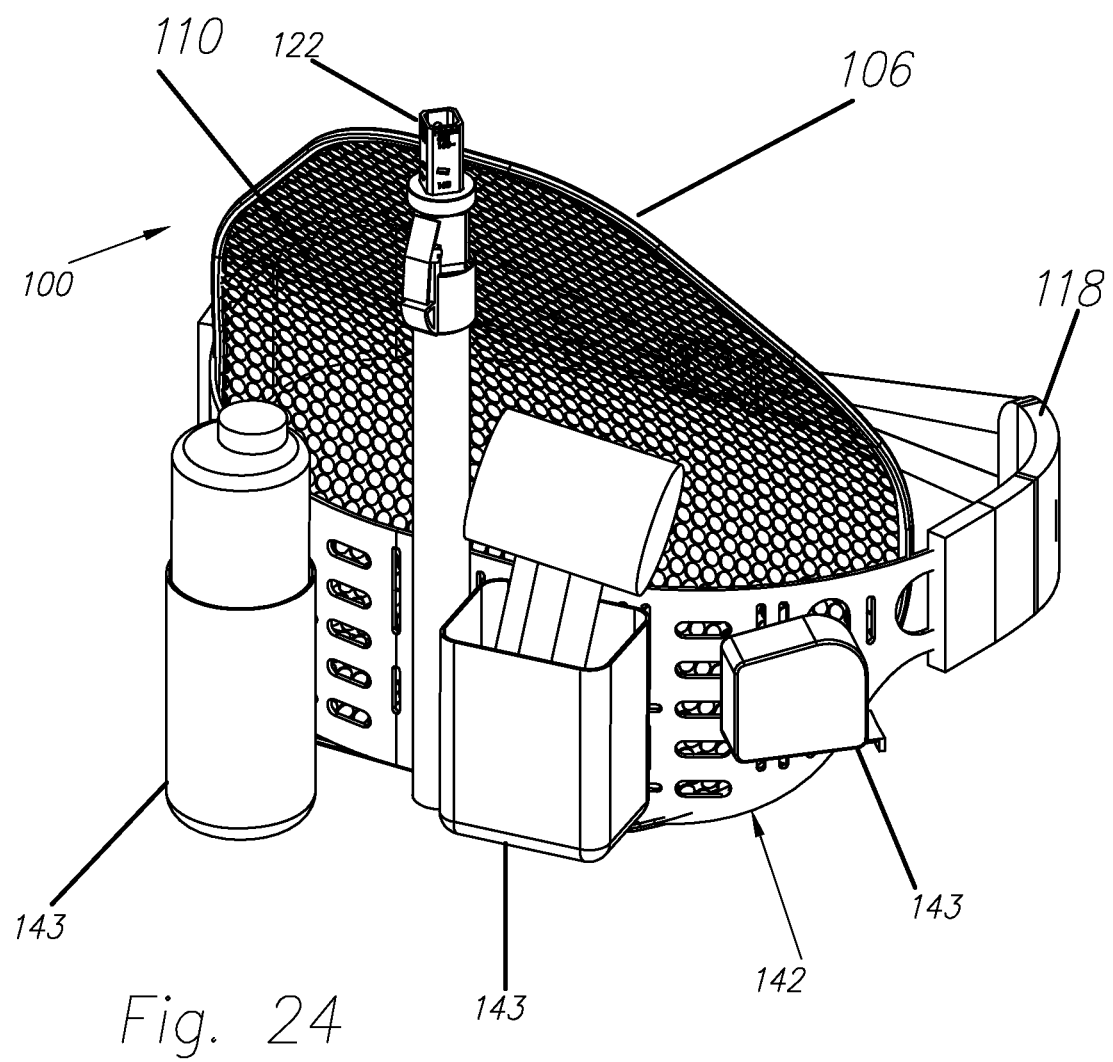
FIG. 24 shows an alternate embodiment of human interface device with a toolholder.

As such, in various embodiments, human interface device 100 may be configured to adequately support various tools. FIG. 23 and FIG. 24 depict an embodiment of human interface device with a tool holder 142 allowing various attachments 143, such as tools or compartments, to be hung or coupled to the human interface device and transfers the weight of the tools to the frame 106. As used herein, tool holder 142 may be referred to herein as a tool attachment or tool belt. In various embodiments, tool holder 142 may include various attachment points, such as hooks, slots, or adhesives for securing the various attachments 143 to tool holder 142. In some embodiments, a tool belt spanning a horizontal section of tool holder 142 may be used to couple attachments 143 to tool holder 142. Each end of the horizontal tool belt may be selectively detached from tool holder 142 to slide pouches onto the horizontal tool belt. In various embodiments, the weight of the tools is supported not only by the person's hip but also by wearer's back through the fabric 110 as described above. Many types of tools or other objects may be attached to human interface device including but not limited to, construction tools, respirators, water bottles, manufacturing parts such as bolts, or other objects commonly used in the workplace.

In some embodiments, tool holder 142 may be attached to a combination of any one of various support structures, including vertical load bearing structure 122 and frame 106. With reference to FIG. 23, shown is an example human interface device with a tool holder 142, in accordance with one or more embodiments. As shown in FIG. 23, tool holder 142 may be used without load bearing structure 122. If tool holder 142 is not coupled to load bearing structure 122, tool holder 142 may retain the properties described above, only without the ability to keep frame 106 from bending in the sagittal plane in response to a load applied to the top of frame 106. As shown in FIG. 23, tool holder 142 may be coupled to belt 118 from two sides. When human interface device 100 is worn, tool holder 142 wraps around person 104 in response to tensile force of belt 118. Thus, load bearing structure 122 allows the weight of the loads (112 and 113) to pass to person 104 through two different paths. Along the first path, a portion of the load weight will pass through fabric 110 to the person's lower back 108. Along the second path, the remaining load weight will pass through tool holder 142, to belt 118 and finally to the hips of the person. This indicates that tool holder 142 must remain rigid in response to load weights 113. However, tool holder 142 should be compliant in response to tensile forces of belt 118 and wraps around said person 104 in response to the tensile force of the belt 118.

Alternatively, tool holder 142 may be coupled to load bearing structure 122. With reference to FIG. 24, shown is an example human interface device 100 with a tool holder 142 extending from the load bearing structure 122, in accordance with one or more embodiments. Such configuration may also be implemented to expand the area that can be used for holding or supporting the load weight by load bearing structure 122. Both load weights 112 and 113 are shown in FIG. 22. These forces are supported by the forces from person 104 onto human interface device 100. Hip reaction force 120 is imposed on human interface device 100 from the person's hip. Force is imposed onto human interface device 100 by the friction forces 152 from person's lower back 108 onto the human interface device 100.

In some embodiments, tool holder 142 may function as a strut, such as strut 142, as described with reference to FIG. 22. Tool holder 142 may be coupled to load bearing structure 122 on opposite sides along the length of the load bearing structure. In some embodiments load bearing structure 122 is configurable to hold or support the tool holder 142 and is coupled to frame 106 wherein the load bearing structure 122 transfers at least a portion of tool holder 142 weight to frame 106. In some embodiments, tool holder 142 may be an integral component or portion of load bearing structure 122. Tool holder 142 may also be coupled to frame 106 on two side edges 107 and 109. As belt 118 pulls two side edges side-edges of 107 and 109 of frame 106, tool holder 142 may also wrap around person 104, similar to frame 106.

Although tool holder 142 may be compliant in transverse plane, tool holder 142 may remain rigid in response to load weights 113 due to its height in the vertical direction and its coupling to load bearing structure. Frame 106 may remain rigid in response to the weight of all tools that may be attached to tool holder 142. The load weight 112 which is imposed on load bearing structure 122 will not deform frame 106. In some embodiments, the distributed load weight 113 on tool holder 142 will not deform frame 106 because tool holder 142 is coupled to load bearing structure 122 and is rigid in response to tool load weights 113. In some embodiments a human interface device 100 is a human-coupled tool holding device configured to be coupled to the trunk of a person 104 comprising frame 106, fabric 110 coupled to frame 106 such that fabric is under tensile forces, belt 118 configured to be coupled to two side edges of frame 106 and a tool holder 142. When belt 118 is worn by person 104, an area of fabric 110 will be pushed against the persons lower back 108 conforming to the shape of the lower back 108 of person 104, and the weight of any tool coupled to or supported by tool holder 142 will be partially supported by friction forces 152 between the area of fabric 110 which is pushed against the persons lower back 108 and the persons lower back 108 allowing person 104 to carry the weight or load of the tools.

Figure 31:
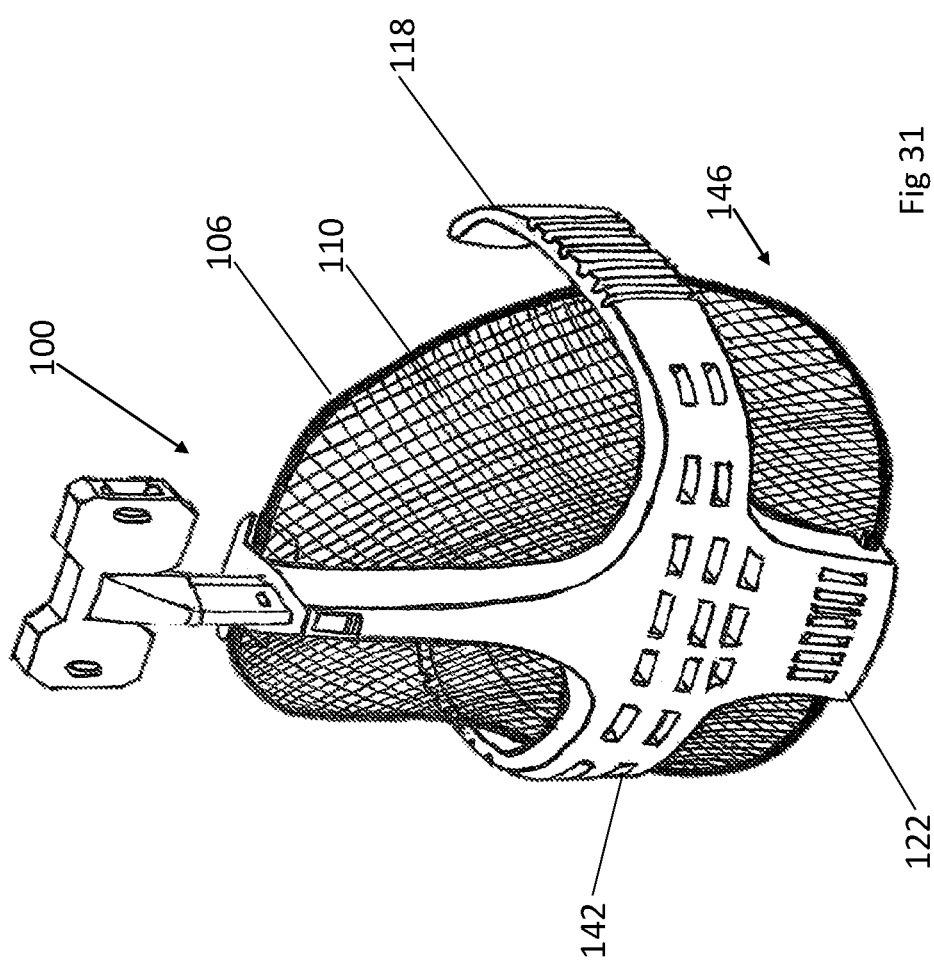
FIG. 31 shows an embodiment of human interface device with combined horizontal and vertical support elements.
Figure 32:
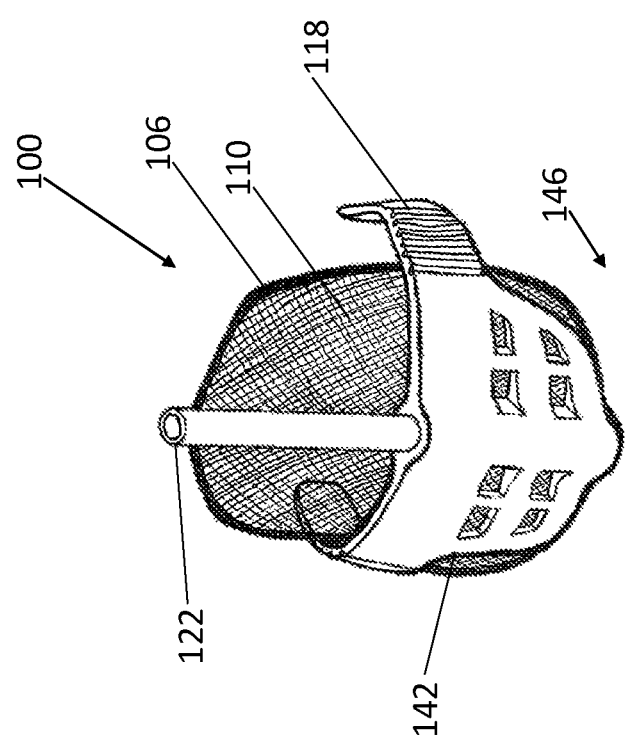
FIG. 32 shows an alternate embodiment of human interface device with combined horizontal and vertical support elements.

In various embodiments, the load bearing structure may comprise of a frame that includes both horizontal and vertical support elements, as shown in FIG. 31 and FIG. 32. Load bearing structure 122a shown in FIG. 31 and FIG. 32 may comprise a frame that acts partially in a vertical and partially in a horizontal direction. The load bearing structure 122 may also incorporate the function of tool holder 142. This may occur through many shapes and patterns in dimensions of all combinations of body planes. Load bearing structure 122 is rather rigid in the middle section and does not allow for bending of frame 106 in sagittal plane 136. Load bearing structure 122 also has two horizontal components that turn into belt 118. The width or thickness of these two horizontal components may reduce as they get closer to the front of the person allowing load bearing structure 122 to wrap around the person. Load bearing structure 122 may be constructed from one piece of injected molded plastic. The thickness in the central area allows for rigidity of load bearing structure 122 in the sagittal plane 136. The load bearing structure 122 may be made using a combination of compliant and non-compliant materials such as composite materials, plastics, particle reinforced plastics, various metal alloys, etc.

Figure 25:
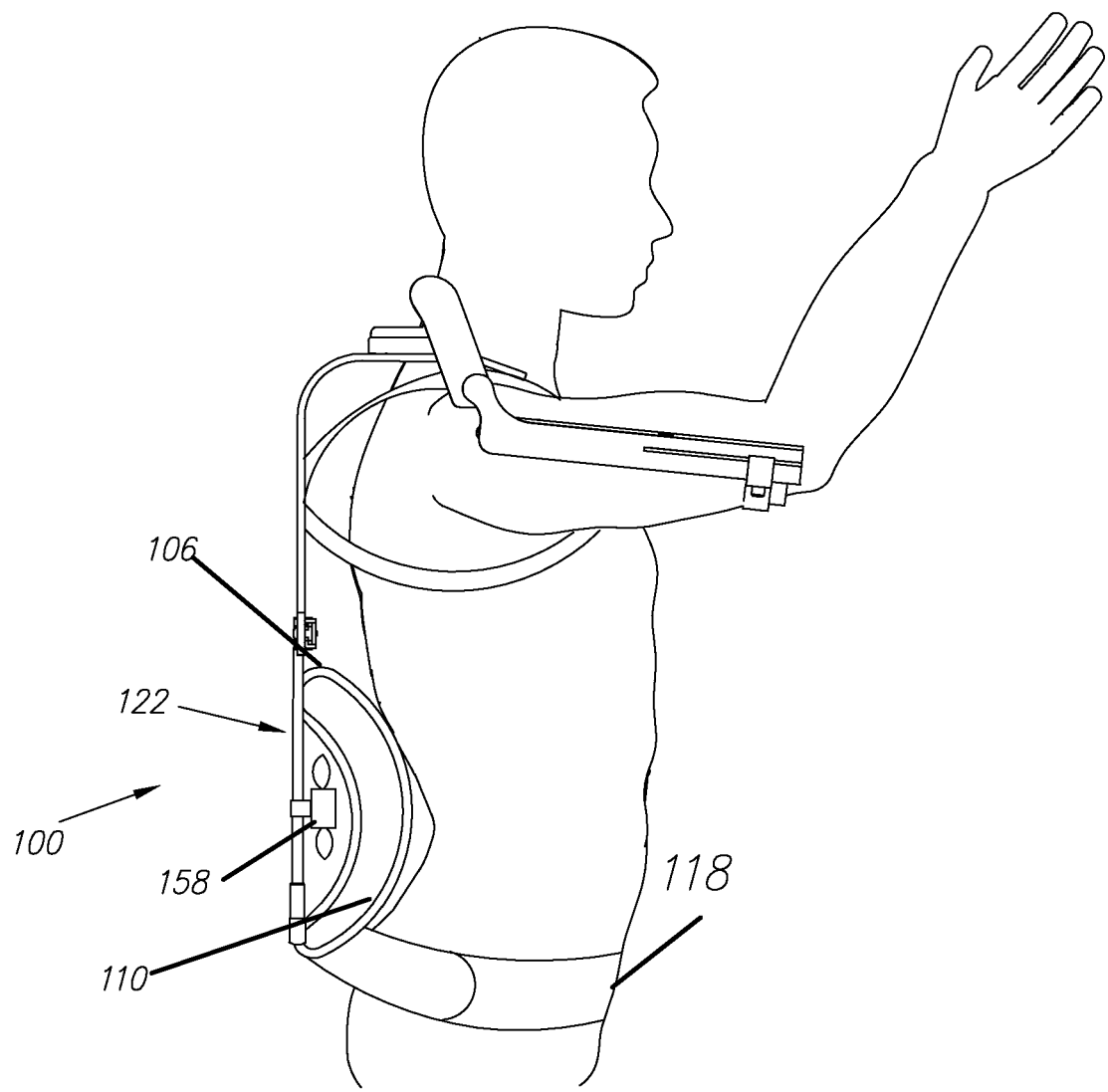
FIG. 25 shows a side view of human interface device with a fan.
Figure 26:
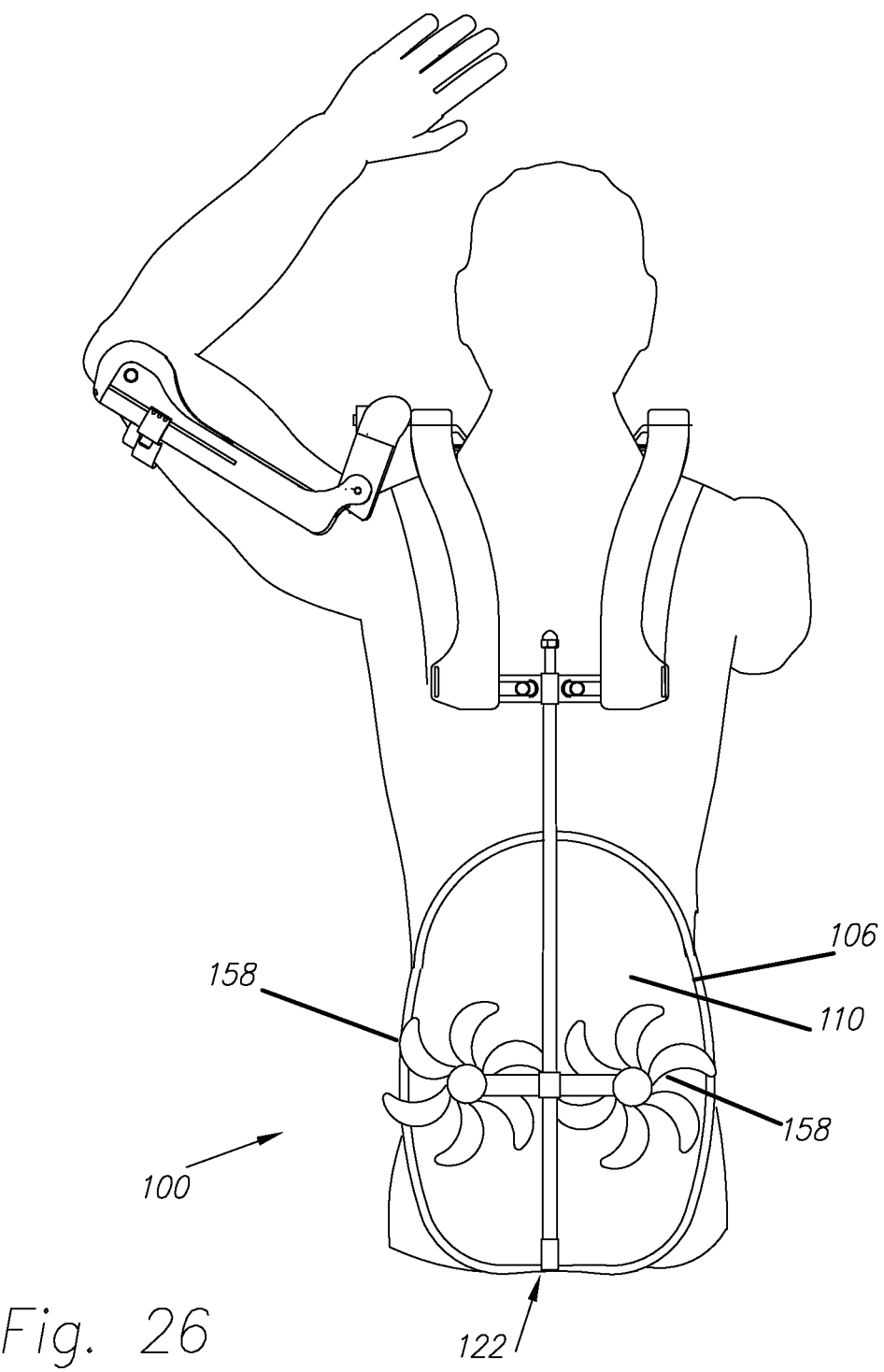
FIG. 26 shows a rear view of human interface device with a fan.

During many occupational tasks thermal discomfort may become a significant issue for workers, especially when using wearable devices on the body. With reference to FIG. 25 and FIG. 26, shown is an example cooling element of a human interface device, in accordance with one or more embodiments. FIG. 25 depicts a side view of cooling element 158 and FIG. 26 depicts a rear view of cooling element 158. In various embodiments, cooling element 158 is coupled to human interface device 100. Cooling element 158 may be configured to cool person's lower back 108 through fabric 110. In some embodiments, cooling element 158 comprises a fan that blows towards and through fabric 110. In some embodiments, human interface 100 comprises a fan providing air flow on person 104. In other embodiments, fabric 110 is configured to create an airgap between frame 106 and the persons lower back 108 to either locate fan cooling element 158 or allow airflow. Cooling element 158 may be mounted to human interface device 100 so that a person may change its position to selectively cool certain areas of the body. Cooling element 158 may similarly work by evaporative, phase change, powered, or chemical means. In some embodiments, cooling element 158 may function through belt 118 or upper torso coupling variations of shoulder straps 125, suspender straps 126, chest strap 127, or scapula straps 129. Cooling element 158 may be mounted to human interface device 100 such that cooling element 158 may be quickly attached and removed to facilitate charging or swapping of cooling element 158. In some embodiments, human interface device 100 may comprise a battery that powers cooling element 158 and an electronics board to control cooling element 158. In other embodiments, cooling element 158 has its own battery and control system. In other embodiments, cooling element 158 is integrated into human interface device 100. Cooling element 158 may also be attached to exoskeleton attachments to human interface device 100 such as a shoulder supporting exoskeleton 169, trunk supporting exoskeleton 170, leg supporting exoskeleton 171, neck supporting exoskeleton, or similar device. Cooling element 158 may be positioned on any of the aforementioned devices to cool the lower back, chest, neck, face, or any other location of person 104. Cooling element 158 may be configured to exhibit various rates of cooling such as a low, medium, and high cooling rate. The design of human interface device 100 may be used to route air from cooling element 158 to person 104. In some embodiments, cooling element 158 is integrated into the structure of human interface device 100. In some embodiments, cooling element 158 is attached to human interface device 100 by means of a pouch attached to tool holder 142. In some embodiments, the human interface device may comprise a thermal element, configured to warm a person through the fabric 110 configured to operate similar to cooling element 158 as described above.

Figure 27:
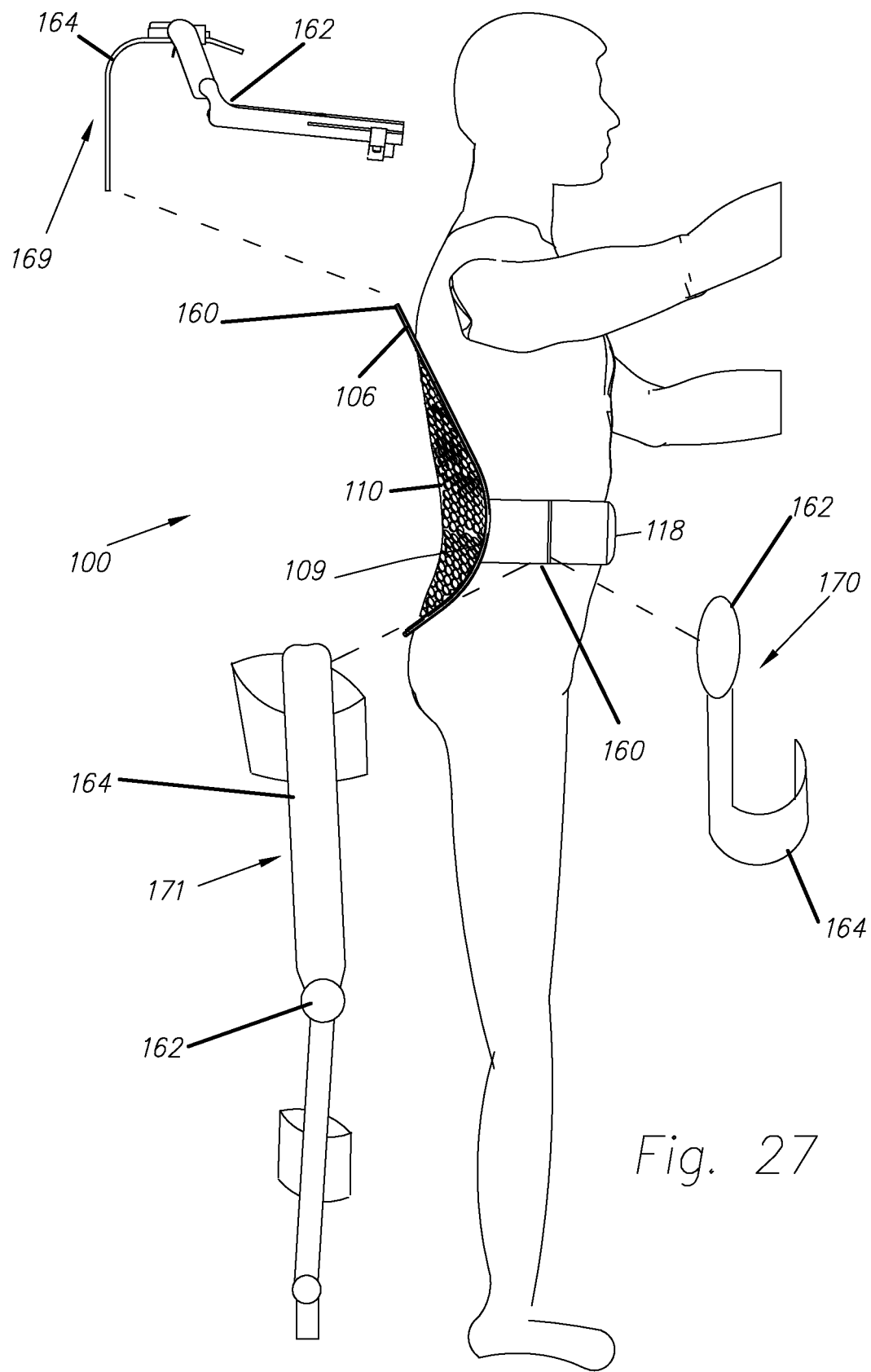
FIG. 27 shows human interface device configured to be coupled to an exoskeleton.

In various embodiments, human interface device 100 may be configured to attach to one or more components of a wearable exoskeleton device. In some embodiments, the exoskeleton is coupled to frame 106. When human interface device 100 is worn by person 104, the forces from wearable exoskeleton will be partially supported by the friction force 152 between the area of fabric 110 which is pushed against the persons lower back 108, and the persons lower back 108, allowing person 104 to comfortably carry wearable exoskeleton. With reference to FIG. 27, shown is a side view of an example human interface device configured to attach to various supporting structures of a wearable exoskeleton, in accordance with one or more embodiments. As shown in FIG. 27, various wearable exoskeleton components may include a shoulder supporting exoskeleton 169, trunk supporting exoskeleton 170, and leg supporting exoskeleton 171. Other exoskeleton components may also be implemented with human interface device 100, such as a neck supporting exoskeleton. The exoskeleton apparatus depicted in FIG. 27 may each comprise torque generating elements 162 and structural frame 164.

In various embodiments, human interface device 100 further comprises a number of exoskeleton attachment points 160 configured to connect to the torque generating elements 162 and or part of the structural frame 164 of various exoskeleton components. For example, an exoskeleton attachment point 160 may be positioned at the upper or side edge of frame 106 for attachment to a shoulder supporting exoskeleton 169. In another embodiment, exoskeleton attachment point 160 may be positioned along load bearing structure 122, wherein load bearing structure 122 transfers at least a portion of the forces from the shoulder supporting exoskeleton 169 to frame 106. As another example, an exoskeleton attachment point 160 may be positioned along the belt 118 or other portion, such as strut or tool holder 142, for attachment to a trunk supporting exoskeleton 170 or leg supporting exoskeleton 171. When coupled, human interface device 100 may become a part of exoskeleton structural frame 164 and transfers reaction forces and torques from the exoskeleton support force, or the weight of the exoskeleton itself, to the person's body.

Figure 29:
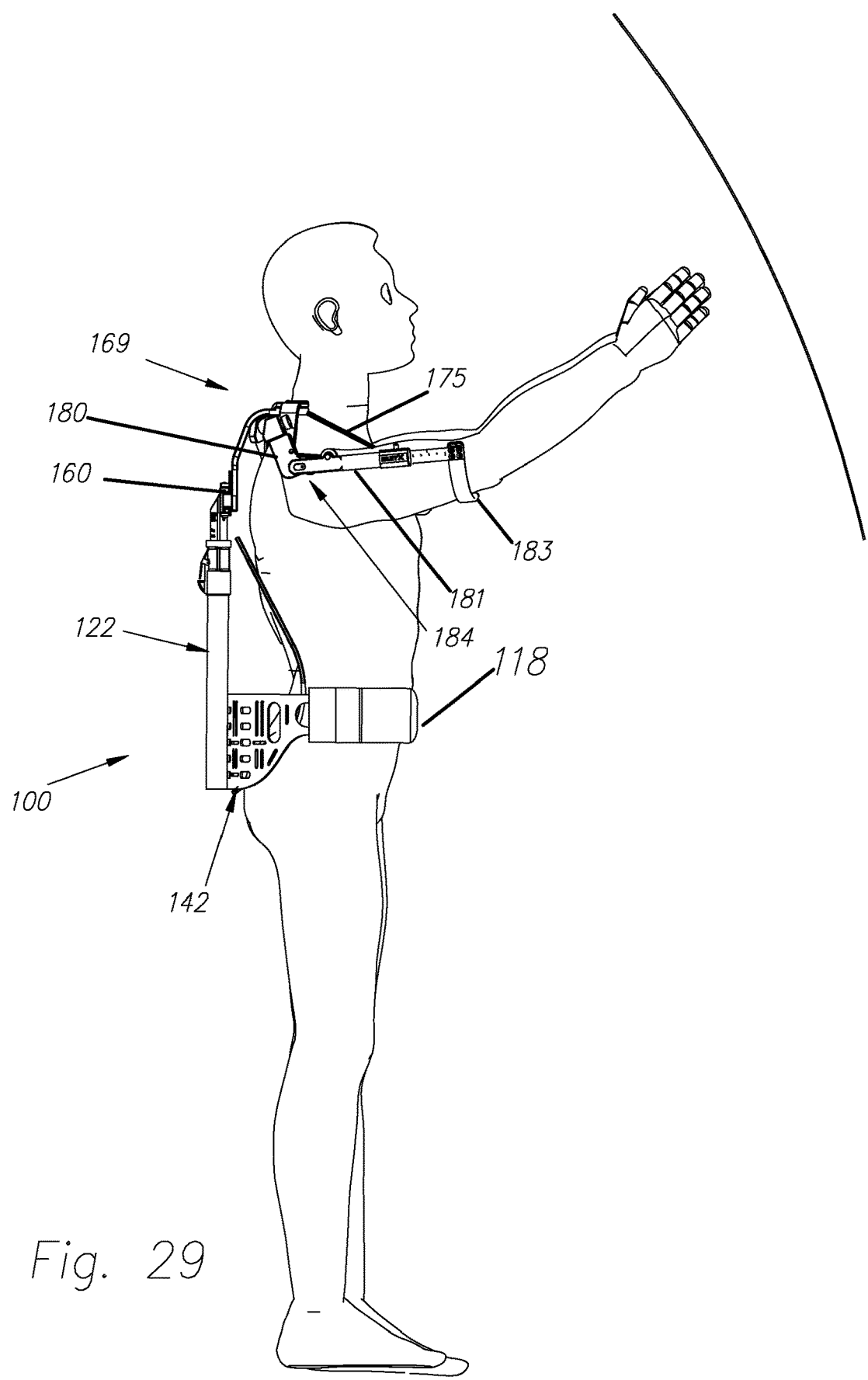
FIG. 29 shows a side view of a shoulder supporting exoskeleton attached to human interface device.
Figure 30:
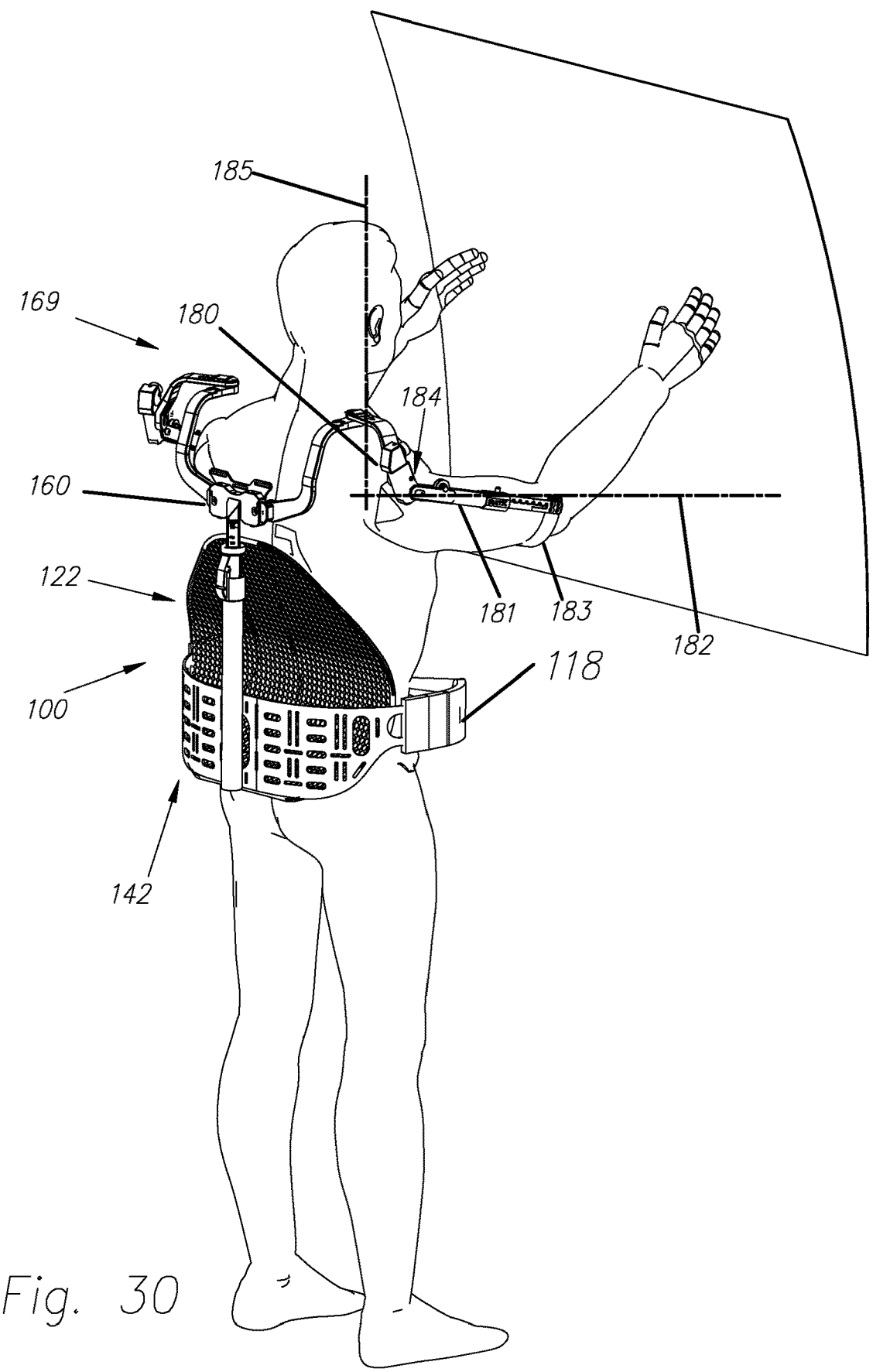
FIG. 30 shows a perspective view of a shoulder supporting exoskeleton attached to human interface device.

An example of a human interface device coupled to a shoulder supporting exoskeleton 169 is also shown in FIG. 29 and FIG. 30. In some embodiments, shoulder supporting exoskeleton 169 is configured to support both arms of person 104. In other embodiments, shoulder supporting exoskeleton 169 may support just one arm of person 104. The shoulder torque generating element 162 applies a supportive force 166 to the person's upper arm 174 creating reaction force and torque on the exoskeleton structural frame 164 and thus onto human interface device 100. These forces are distributed to the body through friction forces 152, normal contact forces 153, and hip reaction forces 120 similar to the response to load weight 112 described in FIG. 5 and FIG. 7. The postural benefits of human interface device 100 may likewise be transferred to the person with the exoskeleton for many postures and tasks.

FIG. 29 and FIG. 30 illustrate various views of an example human interface device 100 coupled to a shoulder supporting exoskeleton 169, in accordance with one or more embodiments. Various adjustment mechanisms and locking mechanisms are described in U.S. patent application Ser. No. 15/848,486 titled METHOD AND APPARATUS FOR HUMAN ARM SUPPORTING EXOSKELETON by Van Engelhoven et al., filed on May 18, 2015, which application is incorporated by reference herein in its entirety and for all purposes. The shoulder supporting exoskeleton 169 may comprise an arm link mechanism coupled to frame 106, load bearing structure 122 or exoskeleton attachment point 160. Arm link mechanism may comprise a proximal link 180 and a distal link 181 configured to rotate relative to each other about a rotating joint and along a first rotational axis 182 substantially orthogonal to a gravity line when the person is standing upright, at least one arm coupler 183 adapted to couple and upper arm of the person to the arm link mechanism, and a torque generator 184 providing a torque to flex the distal link 181 relative to the proximal link 180, wherein the torque has the tendency to flex the distal link 181 relative to the proximal link 180 thereby reducing human shoulder forces and torques required to raise the upper arm of the person. The torque generator 184 of shoulder supporting exoskeleton 169 may comprise a tensile force generator coupled to the proximal link 180 at a first end of the tensile force generator and the distal link 181 at a second end of the tensile force generator, wherein the tensile force in the tensile force generator provides the torque to flex the distal link relative to the proximal link. The tensile force generator may further comprise a coil spring element, a link coupling the coil spring to the first proximal link, and a pulley coupled to distal link 181 wherein the line at least partially encircles the pulley. An upper bracket moveably coupled to the proximal link 180 or a lower bracket moveably coupled to the distal link 181 may be used to adjust the amount of torque provided by the torque generator 184. The shoulder supporting exoskeleton 169 may also comprise a second rotational axis 185 substantially parallel to the gravity line when the person is standing upright that allows the shoulder supporting exoskeleton to rotate in a horizontal motion. Human interface device 100 may similarly be used with any arm support exoskeleton configured to apply and offset force to at least partially offset a gravitational force acting on the arm as the person moves and the arm support follows the motion of the persons arm. An arm supporting exoskeleton may comprise an arm rest to apply the supporting force to the persons upper or lower arm that is rotationally or translationally coupled to the human interface device 100 such that the arm rest is pivot able about multiple axes relative to human interface device 100 or a distal link 181 moves substantially in parallel with the persons arm. A remote spring pack may also be mounted to human interface device 100 that applies a force to the arm cuff or distal link of a shoulder supporting exoskeleton to at least partially offset a gravitational force acting on the arm.

Figure 28:
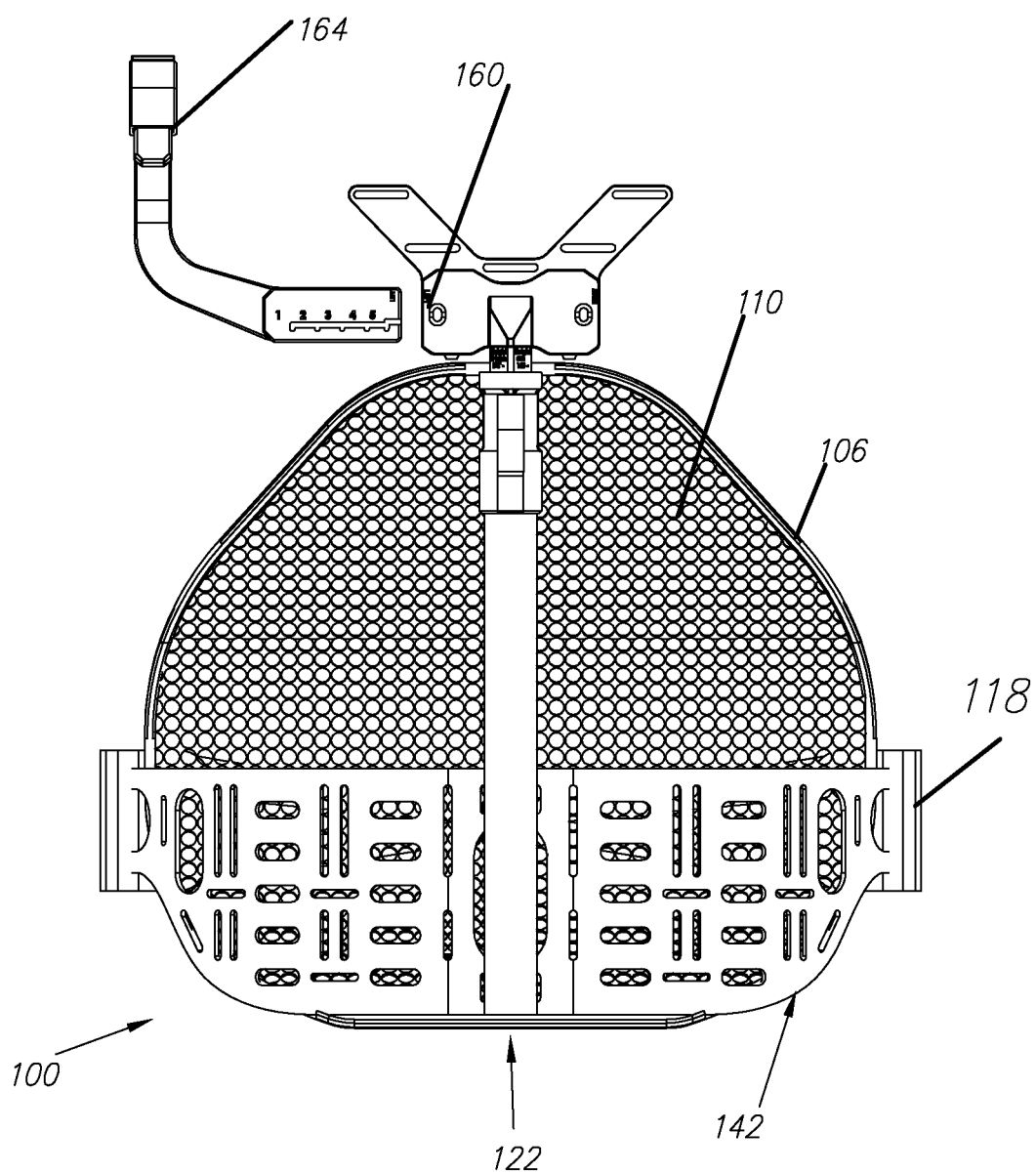
FIG. 28 shows an embodiment of human interface device with an exoskeleton attachment point for a shoulder supporting exoskeleton.

With reference to FIG. 28, shown is a rear exploded view of an exoskeleton attachment point 160 and shoulder supporting exoskeleton structural frame 164, in accordance with one or more embodiments. To better handle the forces exerted by the exoskeleton, exoskeleton attachment point 160 may be connected to a load bearing structure 122 that reduces the forces on frame 106. In other embodiments the exoskeleton attachment point may connect to frame 106, belt 118, or any other part of the human interface device 100 comprising materials that can appropriately handle the structural loads. Exoskeleton attachment point 160 may comprise a male or female connector, adhesive, friction, or screw based connection, among many others. The exoskeleton attachment points 160 may be used with or without tools and may or may not be locked into place with a switch, clamp mechanism, or interlocking notches. Exoskeleton attachment point 160 may also facilitate size adjustments of the exoskeleton relative to the human interface device 100. Various adjustment mechanisms and locking mechanisms are described in U.S. patent application Ser. No. 15/990,434 titled ADJUSTABLE TRUNK AND HIP ASSEMBLY FOR EXOSKELETON APPARATUS by Chavarria et al., filed on May 25, 2017, which application is incorporated by reference herein in its entirety and for all purposes.

Various types and combinations of exoskeletons can be implemented with exoskeleton attachment point 160 including but not limited to exoskeletons providing support to the lower back, shoulder or elbow or wrist or neck, as well as a lower extremity exoskeleton providing support to the hips, knees and thighs. In some embodiments an anchor strap 175, as shown in FIG. 29, connects the shoulder supporting exoskeleton 169 to any of the previously described upper torso couplings, such as the shoulder straps 125. Anchor strap 175 may serve to further stabilize movement of the shoulder supporting exoskeleton 169 relative to human interface device 100. The coupling between anchor strap 175 and shoulder straps 125 may be quickly removable to facilitate quick and tool-free connection and disconnection between the shoulder supporting exoskeleton 169 and human interface device 100.

In some embodiments, a single exoskeleton attachment point 160 may be used to connect various types of exoskeleton components. In other embodiments, an exoskeleton attachment point 160 may be specific to a single type of exoskeleton component and human interface device 100 may comprise multiple exoskeleton attachment points 160. In a preferred embodiment an exoskeleton attachment point 160 located near the top of the load bearing structure 122 is configured to attach to a shoulder supporting exoskeleton 169 and an exoskeleton attachment point 160 near the tool holder 142, belt 118 or frame 106 is configured to attach to a leg supporting exoskeleton 171 or a trunk supporting exoskeleton 170. The shoulder supporting exoskeleton 169, leg supporting exoskeleton 171, or trunk supporting exoskeleton 170 may all be attached individually or in combination to human interface device 100 through various exoskeleton attachment points 160. It should be understood by one skilled in the art that many other types of exoskeleton components may be connected to the human interface device 100 at many locations, not necessarily depicted here. Depending on the type of exoskeleton the human interface device 100 is connected to, the structure may be optimized for various directions of reaction forces 167 and torques 168 from the exoskeleton supportive force 166. In addition to the vertical downward forces of load weight 112 shown in FIG. 22, upward forces or horizontal forces may also be applied to the human interface device 100. These forces may be transferred to the human body through additional points that are attached to human interface device 100 along with the exoskeleton, such as thigh straps, seat straps, or upper torso couplings. Seat straps and thigh straps may be used to keep human interface device 100 from rising upwards on the person's torso due to bending motions or forces and torques exerted by a leg supporting exoskeleton 171 or trunk supporting exoskeleton 170. Seat straps and thigh straps may be attached to frame 106, load bearing structure 122, tool holder 142, belt 118, or any other part of human interface device 100.

Figure 33:
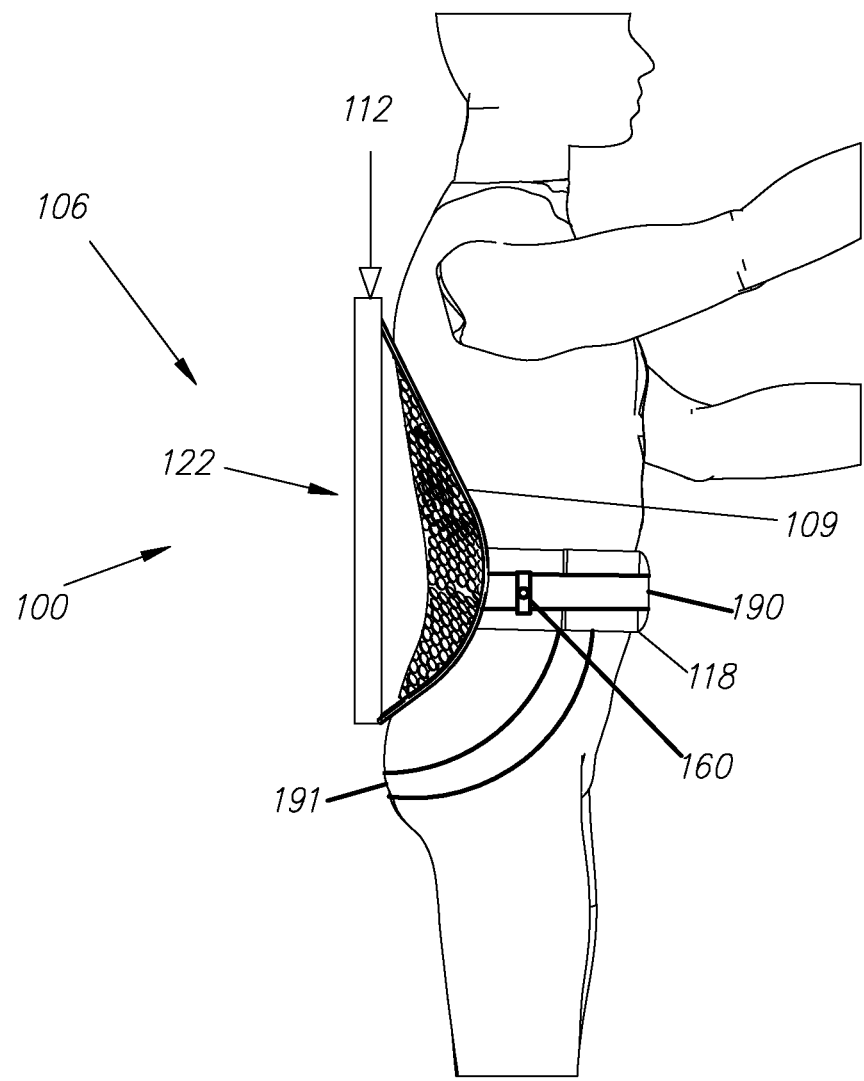
FIG. 33 shows an embodiment of human interface device with an exoskeleton attachment point located on a belt.
Figure 34:
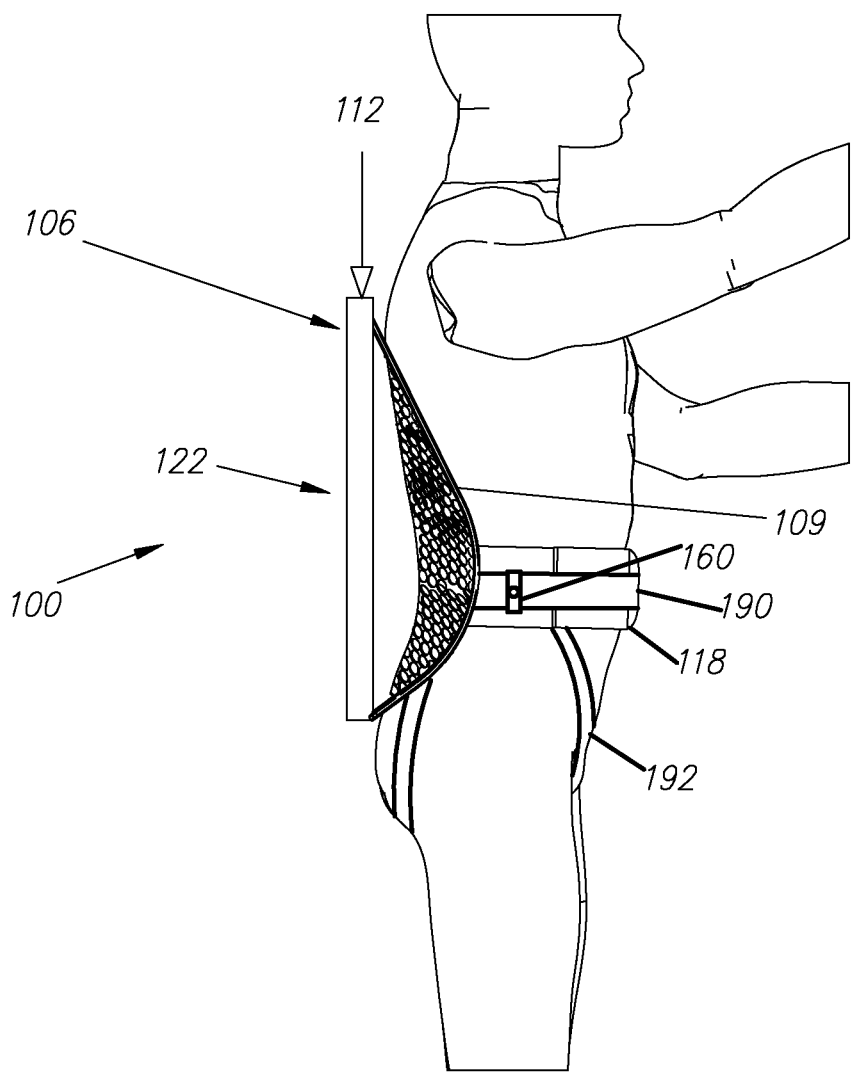
FIG. 34 shows an alternate embodiment of human interface device with an exoskeleton attachment point located on a belt.
Figure 35:
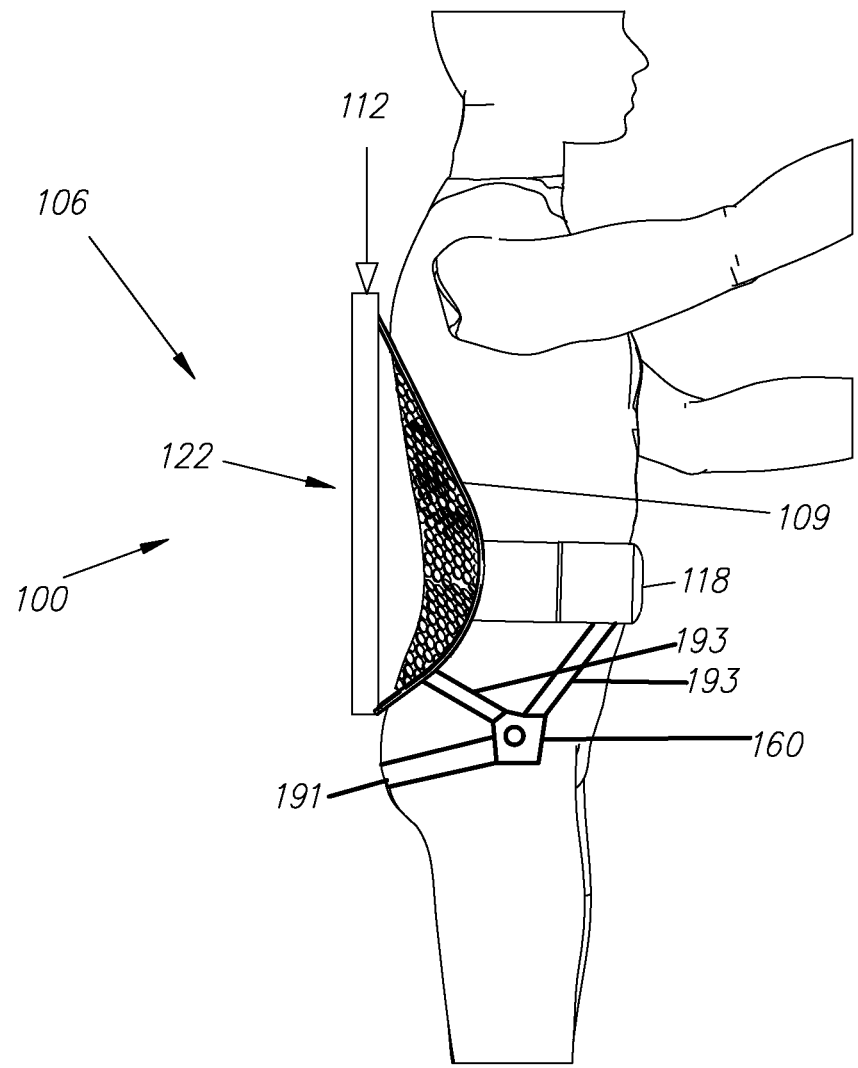
FIG. 35 shows an embodiment of human interface device with an exoskeleton attachment point is suspended from a belt.

FIG. 33 shows an embodiment of human interface device 100 with an exoskeleton attachment point 160 located substantially on belt 118. Belt 118 may further comprise a secondary belt 190 coupled to exoskeleton attachment point 160 that allows the location of exoskeleton attachment point 160 to be adjusted along the length of secondary belt 190. This may be used to align an exoskeleton, such as a trunk supporting exoskeleton 170 or leg supporting exoskeleton 171 to the joints of person 104. Human interface device 100 may further comprise a seat strap 191 that spans between two sides of human interface device 100 behind person 104. Seat strap 191 may be used to prevent human interface device 100 from riding up on person 104 when person 104 bends forward. Seat strap 191 may be connected between two side edges of frame 106, belt 118, tool holder 142, or load bearing structure 122. FIG. 34 depicts an alternate embodiment where human interface device comprises thigh straps 192 instead of seat strap 191. Thigh strap 192 encircles person's leg, connecting to two points on human interface device 100. Human interface device 100 may comprise one thigh strap 192, or two thigh straps 192 to help anchor human interface device 100 from moving upwards relative to person 104. FIG. 35 depicts an alternate embodiment of human interface device 100 where exoskeleton attachment point 160 is suspended from human interface device 100 by one or more suspension straps 193. Suspension straps 193 may be used to lower the location of exoskeleton attachment point 160 relative to human interface device 100. Two suspension straps 193 may be used to prevent exoskeleton attachment point 160 from swinging relative to human interface device 100. Suspension straps 193 may be tightened or loosened to adjust the position of exoskeleton attachment point 160 on person 104. If both suspension straps are tightened or loosened together, the height of exoskeleton attachment point 160 can be adjusted. If only one suspension strap 193 is loosened or tightened, the forward-backward position of exoskeleton adjustment point 160 can be adjusted. Suspension straps 193 may be attached to belt 118, frame 106, load bearing structure 122, tool holder 142 or any component of human interface device 100. All straps attached to human interface device 100 described above may be quickly attached or removed to alter the configuration of human interface device 100 depending on the exoskeleton attachments and postures or movements of person 104 wearing human interface device 100.

Figure 36:
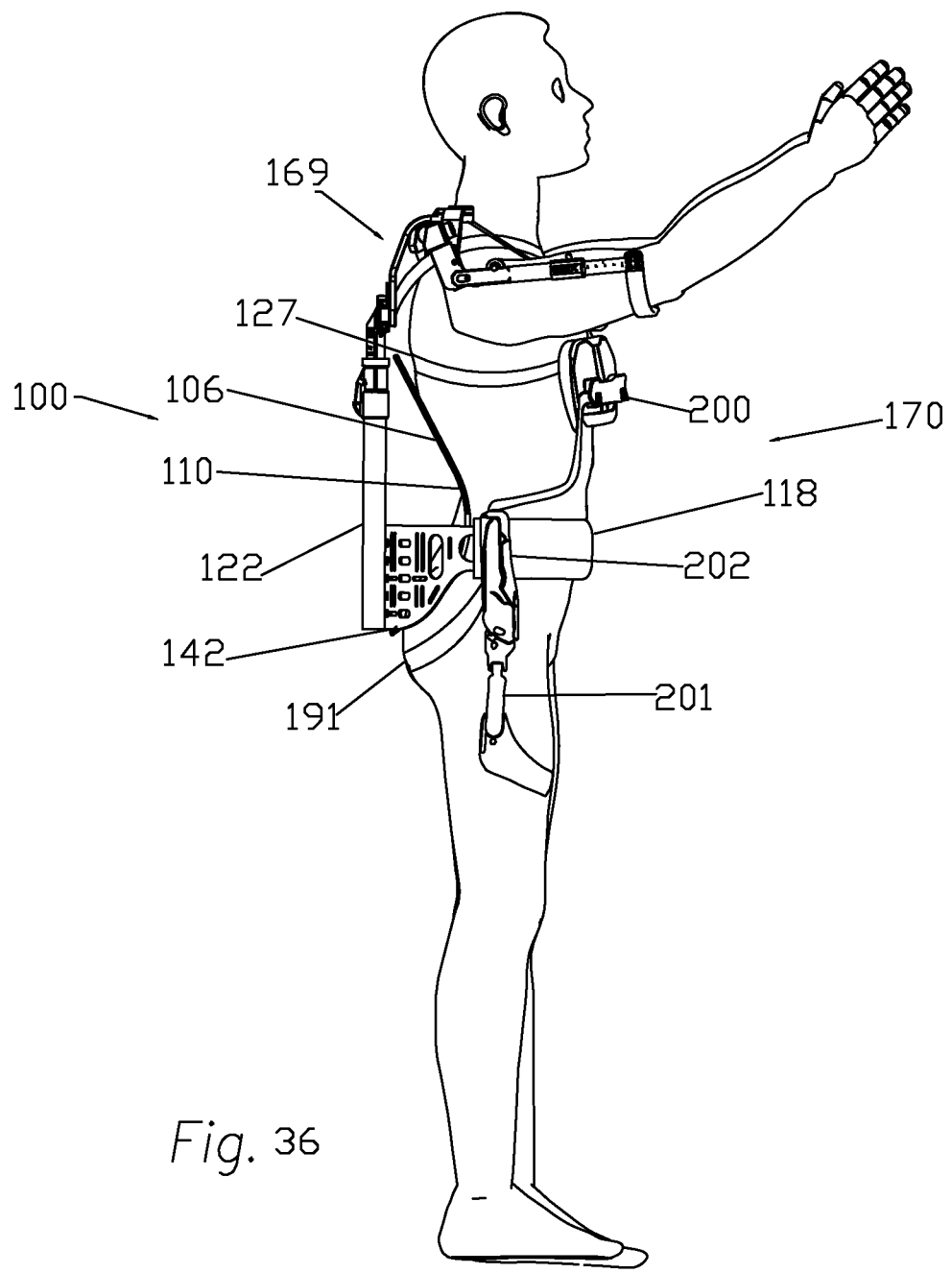
FIG. 36 shows an embodiment of human interface device with a shoulder supporting exoskeleton and a back supporting exoskeleton.

FIG. 36 illustrates an example human interface device 100 also coupled to a trunk supporting exoskeleton 170, in accordance with one or more embodiments. Trunk supporting exoskeleton 170 may be used interchangeably with trunk supporting exoskeleton. Various adjustment mechanisms and locking mechanisms are described in U.S. patent application Ser. No. 15/848,486 titled TRUNK SUPPORTING EXOSKELETON AND METHODS OF USE by Tung et al., filed on Jun. 10, 2011, which application is incorporated by reference herein in its entirety and for all purposes. The trunk supporting exoskeleton 170 is configured to be worn by person 104 to reduce muscle forces in a back of person 104 during forward lumbar flexion. In some embodiments, trunk supporting exoskeleton 170 comprises a supporting trunk 200 configured to be coupled to the trunk of person 104, and first and second thigh links 201 configured to move in unison with thighs of person 104 in a manner resulting in flexion and extension of respective first and second thigh links 201 relative to supporting trunk 200. Trunk supporting exoskeleton 170 may also comprise first and second torque generators 202 located on both left and right halves of the person 104 substantially close to the hip of the person 104, coupling supporting trunk 200 to the first and second thigh links 201 respectively and configured to generate torque between the first and second thigh links 201 and supporting trunk 200. When the person 104 bends forward in a sagittal plane such that a predetermined portion of supporting trunk 200 passes beyond a predetermined angle from vertical, at least one of the first and second torque generators 202 imposes a resisting torque between supporting trunk 200 and at least one of the first and second thigh links 201, causing supporting trunk 200 to impose a force against trunk of person 104 and at least one of the first and second thigh links 201 to impose a force onto at least one of the thighs of person 104. When the predetermined portion of supporting trunk 200 does not pass beyond the predetermined angle from vertical, the first and second torque generators 202, through and entire range of motion of the first and second thigh links 201, impose no resisting torques between supporting trunk 200 and the respective first and second thigh links 201. In some embodiments the structure of human interface device 100 serves as the structure of supporting trunk 200.

Figure 37:
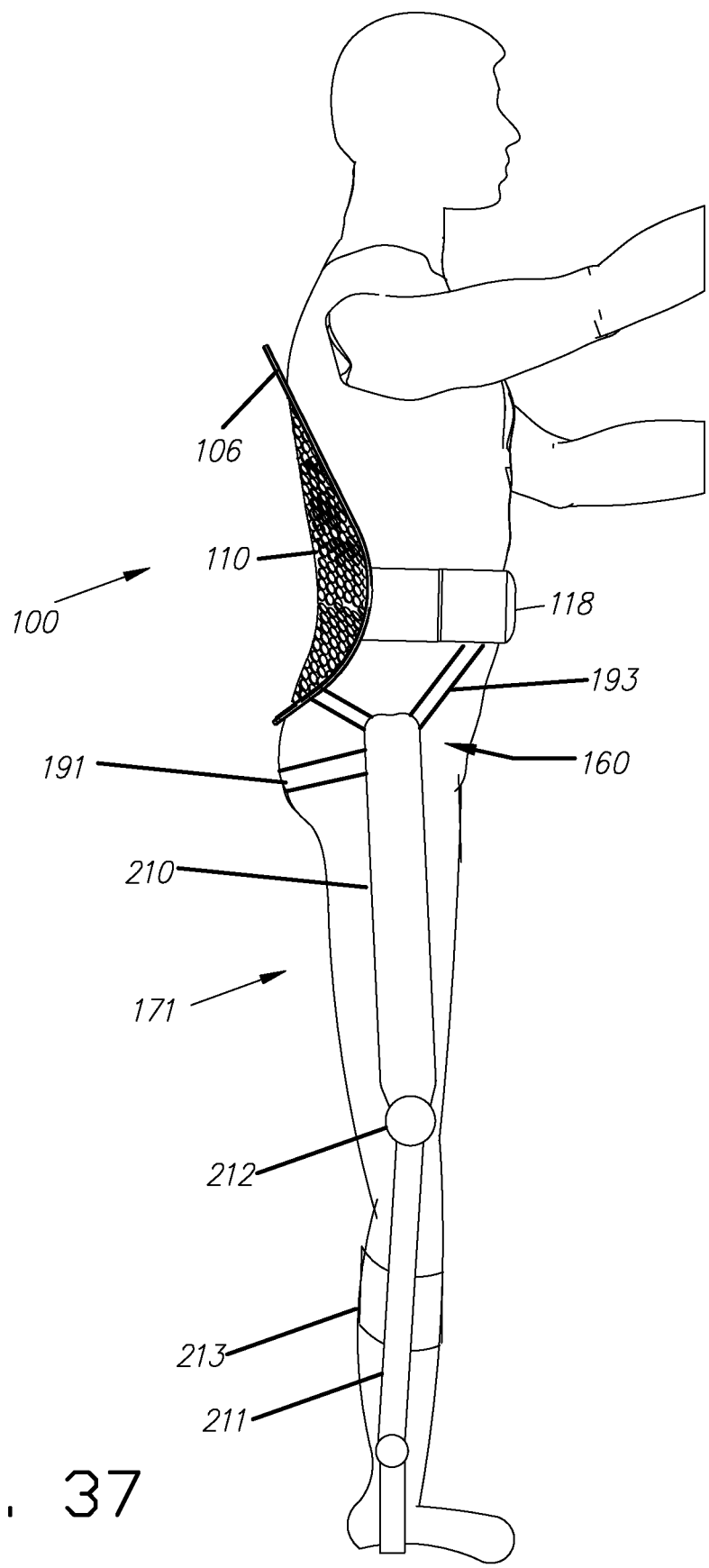
FIG. 37 shows an embodiment of human interface device with a leg supporting exoskeleton.

FIG. 37 illustrates an example human interface device 100 also coupled to a leg supporting exoskeleton 171, in accordance with one or more embodiments. Leg supporting exoskeleton 171 may be used interchangeably with leg supporting exoskeleton. Various adjustment mechanisms and locking mechanisms are described in U.S. patent application Ser. No. 15/848,486 titled EXOSKELETON LEGS TO REDUCE FATIGUE DURING REPETITIVE AND PROLONGED SQUATTING by Tung et al., filed on Jun. 26, 2015, which application is incorporated by reference herein in its entirety and for all purposes. In some embodiments, leg supporting exoskeleton 171 comprises a thigh link 210, a shank link 211, a knee joint 212 coupled to the thigh link 210 and the shank link 211 and configured to allow flexion and extension between the thigh link 210 and shank link 211. In some embodiments, leg supporting exoskeleton 171 may also comprise a force generator comprising a first end and a second end, wherein the first end is coupled to the shank link, and the second end coupled to the thigh link. Leg supporting exoskeleton 171 may also comprise a constraining mechanism coupled to the thigh link, wherein the constraining mechanism is configured to have at least two operation modes, a constrained mode and an unconstrained mode. A first signal processor may be configured to move the constraining mechanism between its at least two operation modes. When in the constrained mode, the constraining mechanism is configured to limit the second end of the fore generator to a rotational motion relative to the thigh link, and is configured to provide support to the person 104 when the knee of the person is flexing. When in the unconstrained mode the constraining mechanism is configured to allow additional motion of the second end of the force generator relative to the thigh link in addition to the rotation motion, and is configured to provide no support to the wearer when the knee of the wearer is flexing. In other embodiments the knee joint 212 may be configured to prevent knee flexion of the wearer in at least one angular position to support person 104 in a seated or squatting position. Seat strap 191 may serve to transfer forces from the leg supporting exoskeleton 171 to a person's buttocks, and a shank coupling 213 may serve to transfer forces from the leg supporting exoskeleton 171 to the shank of a person 104. Human interface device 100 may be used to at least partially support the weight of leg supporting exoskeleton 171 on persons hips or to provide an exoskeleton attachment point 160 to more easily don and doff the leg supporting exoskeleton 171.

Figure 38:
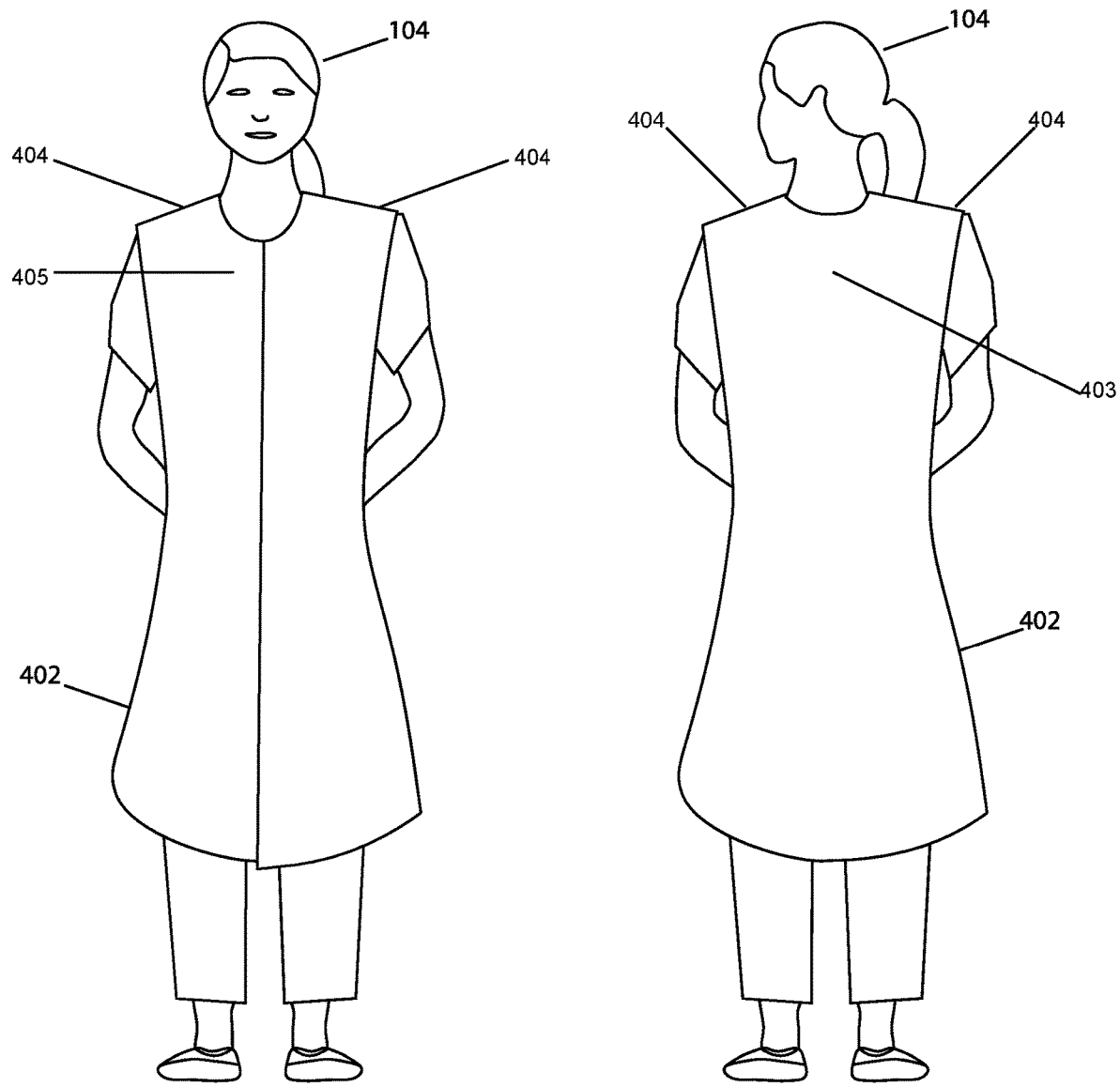
FIG. 38 shows a shielding apron.

One application of the human interface device 100 is to support the weight of a shielding apron 402. FIG. 38 shows the front and the rear view of shielding apron 402 that covers majority of the wearer's body and protects the wearer from harmful effects of exposure to ionizing radiation. In some embodiments, shielding apron 402 is a radiation shielding apron to minimize the exposure of a person to x-ray radiation. Shielding apron 402 may comprise a form of radiation protection such as lead or lead composite blend which consists a mixture of lead and at least another material such as rubber and PVC vinyl. Lead aprons are the most effective personal radiation protection means and should be worn by everyone in a proximity of the radiation sources. Lead aprons may reduce the dose received by over 90% depending on the energy of the X-rays and the lead equivalent thickness of the apron. Many lead aprons weigh well over 15 pounds. This can be an exhausting weight to carry during long procedures, or for people with a smaller frame. In some embodiments of the invention, human interface device 100 can remove the weight of a shielding apron 402 from the wearer's shoulder and transfer it to the person's lower back. In some embodiments of the invention, human interface device 100 can transfer a portion of the weight of a shielding apron 402 to the person's lower back. Additionally, when human interface device 100 is worn by a person to support shielding apron 402, fabric 110 imposes normal contact forces on the person's lower back to maintain the lower back lordotic curve of the person's spine in its natural form.

Here the word shielding apron 402 may be used to represent a heavy suit, garment or attire for the wearer protection against radiation. The invention here, although motivated here for supporting the weight of a radiation protective garment, can equally be used to support the weight of any protective equipment, costume, or clothing worn by a person or heavy object mounted to person 104. Shielding apron 402 may take the form of an apron, coat, vest, smock, jacket, shirt, or any other garment worn on the torso of person 104. Other examples of shielding apron 402 include but are not limited to bomb squad suits, ballistic or bulletproof vests, nuclear radiation aprons, large costumes, and other environmental personal protective equipment. Shielding apron 402 may also include a blast shield, riot shield, or any other type of handheld shield whose weight can be transferred to person 104 by human interface device 100.

Figure 39:
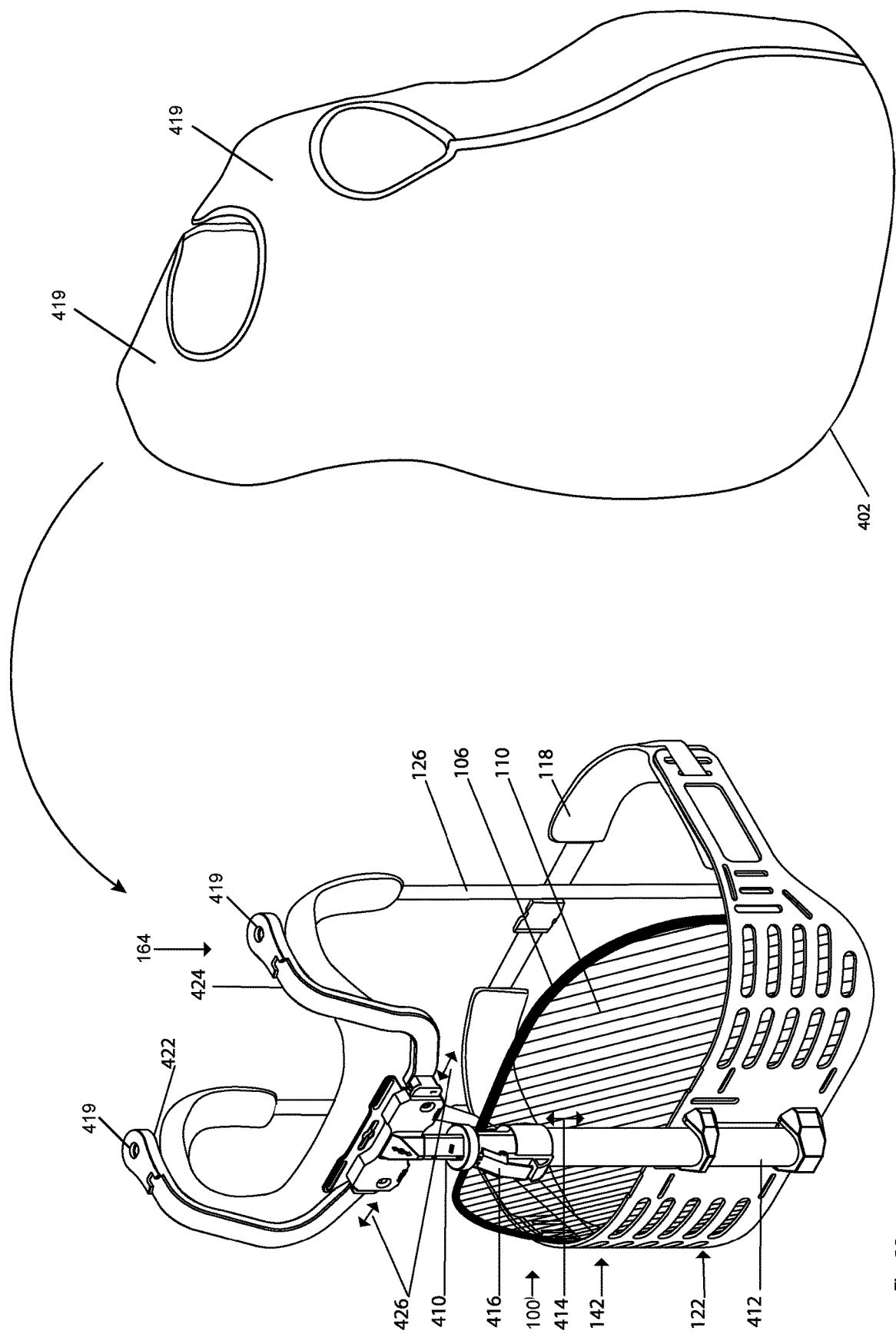
FIG. 39 shows an embodiment of the human interface device and a shielding apron (shielding coat)
Figure 40:
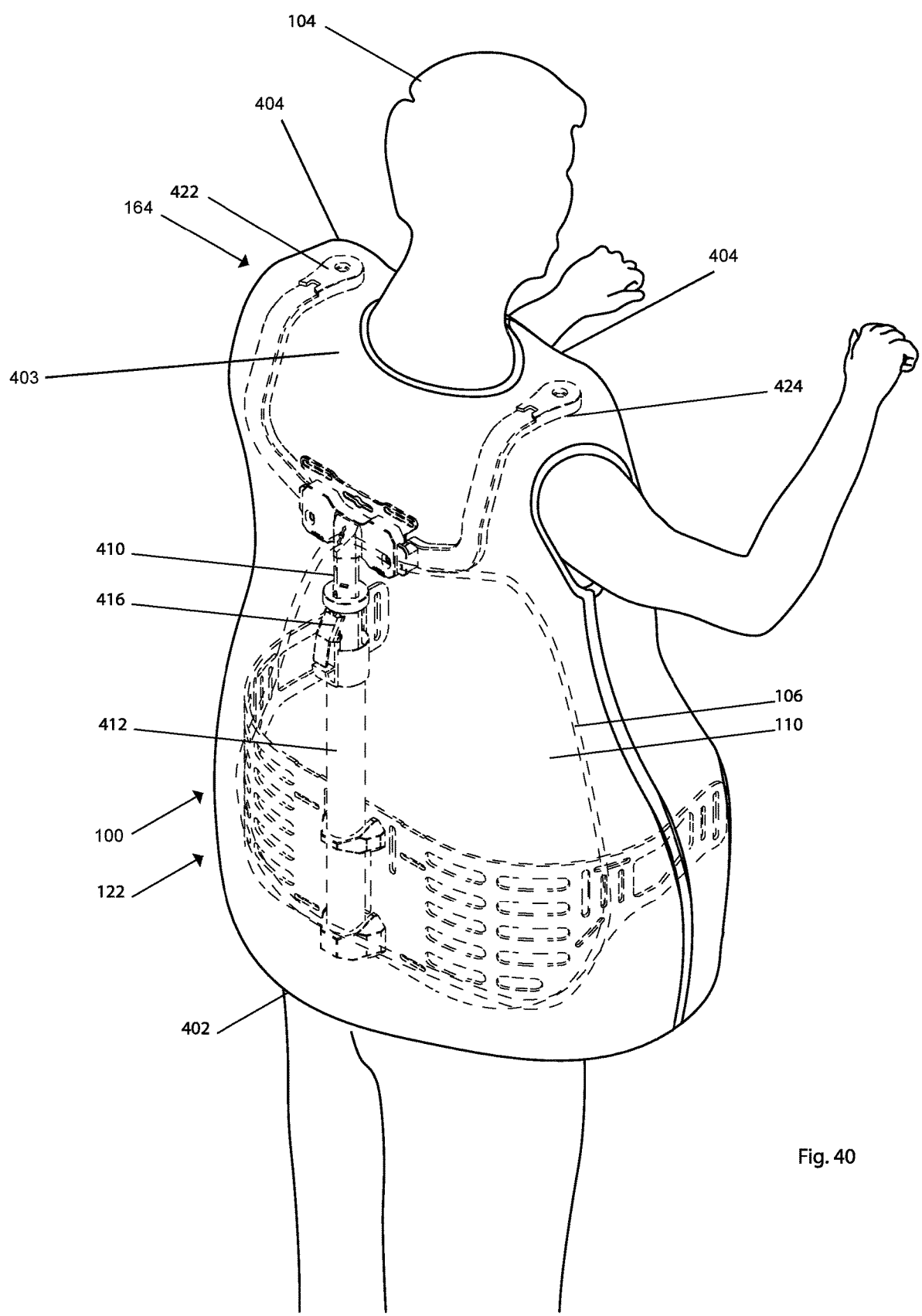
FIG. 40 shows an embodiment of the human interface device worn under a shielding apron.

FIG. 39 shows an embodiment of a human interface device 100 configured to be worn with a shielding apron 402. In some embodiments, human interface device 100 is configured to be worn under the shielding apron 402. Human interface device 100 is configured to be coupled to the trunk of a person 104 as shown in FIG. 40. Shielding apron 402 is either coupled to or rests on human interface device 100. When person 104 wears human interface device 100, at least a portion of the weight of the shielding apron 402 passes through human interface device 100. In some embodiments of the invention, shielding apron 402 does not rest on the wearer's shoulders and the entire weight of shielding apron 402 passes through human interface device 100. In some embodiments of the invention, human interface device 100 causes the weight of shielding apron 402 to bypass the wearer's spine. As will be described later, using human interface device 100 causes a portion or all of the weight of shielding coat 402 to be transferred onto the person's lower back and hip area instead of the person's shoulders and spine. This will reduce the risk of injuries around the shoulder and spine area.

FIG. 39 illustrates a rear-perspective view of human interface device 100 configured to support a shielding apron 402. Human interface device 100 is configured to be coupled to the trunk of a person 104. The trunk of person 104 may be defined as the torso of the person 104 consisting of the back, hips, chest, abdomen, or shoulders. Human interface device 100 comprises frame 106 and fabric 110 which is coupled to frame 106 and is configured to be under tensile forces. Human interface device 100 further comprises belt 118 coupled to two side edges of frame 106. When belt 118 is worn by person 104, an area of fabric 110 will be pushed against the person's lower back 108 conforming to the shape of lower back 108 of person 104. When human interface device 100 is worn by person 104, the weight of shielding apron 402 coupled to or supported by frame 106 will be, at least partially, supported by the friction force between the area of fabric 110 pushed against person's lower back 108, and the person's lower back 108. This allows person 104 to carry the shielding apron with less forces on the person's spine and shoulders. FIG. 2 illustrates a side view of frame 106 and fabric 110, and the matching of curve in fabric 110 and the curve of person's lower back 108. In some embodiments, frame 106 transfers at least a portion of the weight of shielding apron 402 to the low back or hips of person 104. Frame 106 may further comprise padding to more comfortably transfer forces to person 104. The roles of frame 106, fabric 110 and belt 118 in transferring the load weight (i.e. the weight of shieling apron 402 in this case) are described in previous sections with the help of FIG. 1 through FIG. 18.

Figure 41:
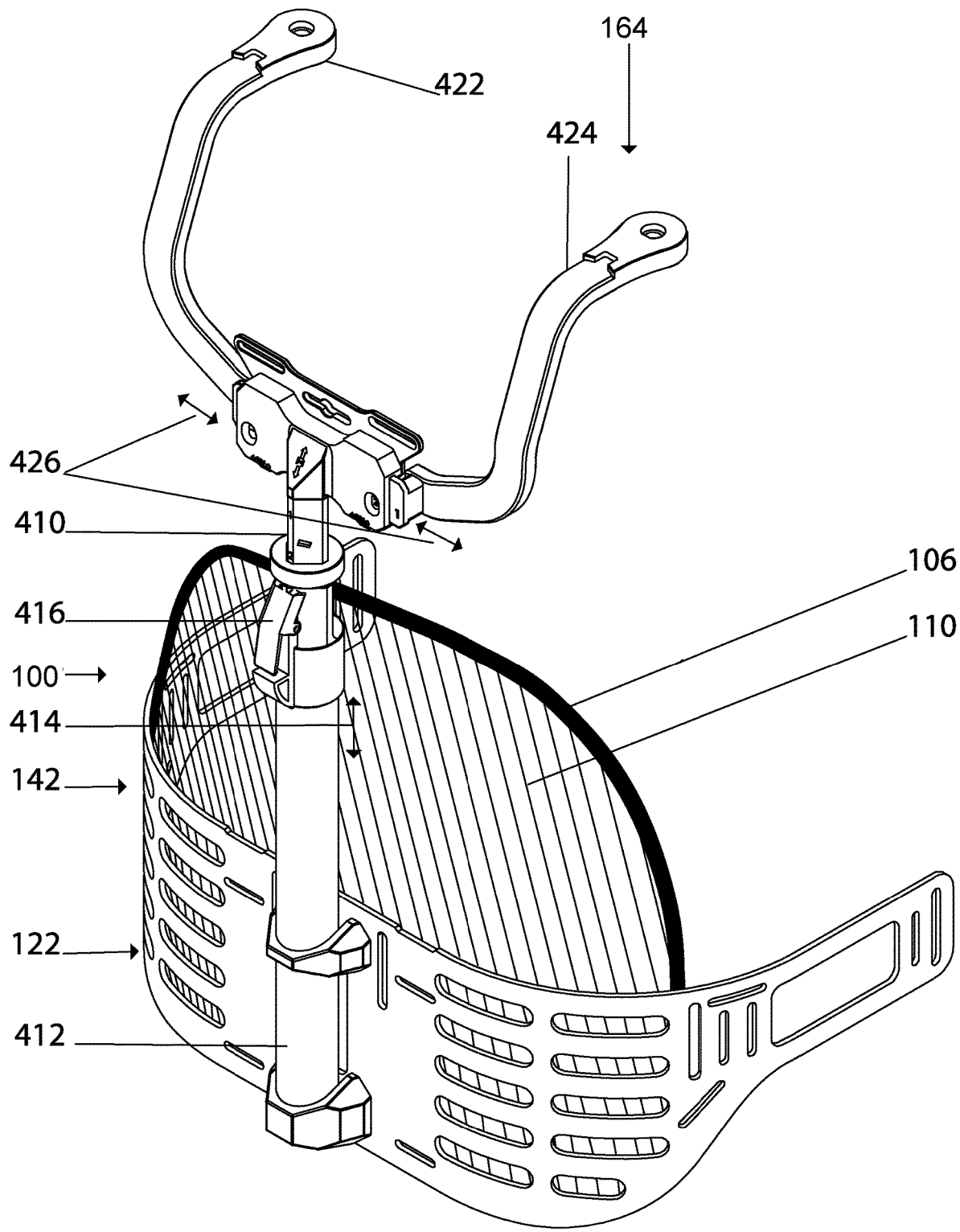
FIG. 41 shows a rear view of the human interface device configured to support a shielding apron.

In some embodiments of the invention, as shown in FIG. 39, human interface device 100 may further comprise load bearing structure 122 configured to hold or support shielding apron 402. The load bearing structure 122 is coupled to frame 106 such that load bearing structure 122 transfers a portion or all the of the weight of shielding apron 402 to the frame 106. In some embodiments, load bearing structure 122 is configurable to be coupled to frame 106 and is rigid enough to ensure that frame 106 does not deform or change its shape in the sagittal plane in response to the weight of shielding apron 402. In some embodiments of invention, load bearing structure 122 comprises strut 142. Strut 142 is configured to be coupled to frame 106 through at least two coupling locations 123 and 124 (shown in FIG. 20). In some embodiments, the rigidity of load bearing structure 122 prevents frame 106 from deforming in sagittal plane 136. The coupling between load bearing structure 122 and frame 106 may be adjustable to alter the curvature of frame 106 in the sagittal plane. In some embodiments of invention, as shown in FIG. 39, load bearing structure 122 comprises one or a plurality of concentric sections which are configured to slide into one another. As can be seen in FIG. 41, inner section 410 is able to slide inside outer section 412 along arrow of vertical direction 414. Manual lock 416 is used to lock inner section 410 relative to outer section 412. This adjustment along arrow of vertical direction 414 may be used to allow human interface device 100 to properly fit persons of varying height. This may allow the adjustability of the location of shielding apron 402 relative to shoulders of person 104.

In some embodiments of the invention as show in FIG. 40, human interface device 100 further comprises structural frame 164 coupled to frame 106 and is configured to stay above the person's shoulders transferring at least a portion of the weight of the shielding apron 402 to frame 106. Structural frame 164 may be made of a rigid or semi rigid material including but not limited to, sheet metal, tubing, injection molded plastic, or carbon fiber. In some embodiments of the invention, as shown in FIG. 40, human interface device 100 further comprises structural frame 164 coupled to load bearing structure 122 and is configured to stay above the person's shoulders transferring at least a portion of the weight of the shielding apron 402 to frame 106. In some embodiments of the invention, not shown in the figures, human interface device 100 further comprises structural frame 164 coupled to strut 142 and is configured to stay above the person's shoulders transferring at least a portion of the weight of the shielding apron 402 to frame 106. Structural frame 164 may be coupled to frame 106, load bearing structure 122, or strut 142 by means of screws, bolts, adhesives, welding, and part profiles. In some embodiments of the invention, structural frame 164 may be integrated into frame 106. In some embodiments of the invention, structural frame 164 may be integrated into load bearing structure 122. In some embodiments of the invention, structural frame 164 may be integrated into strut 142.

Figure 47:
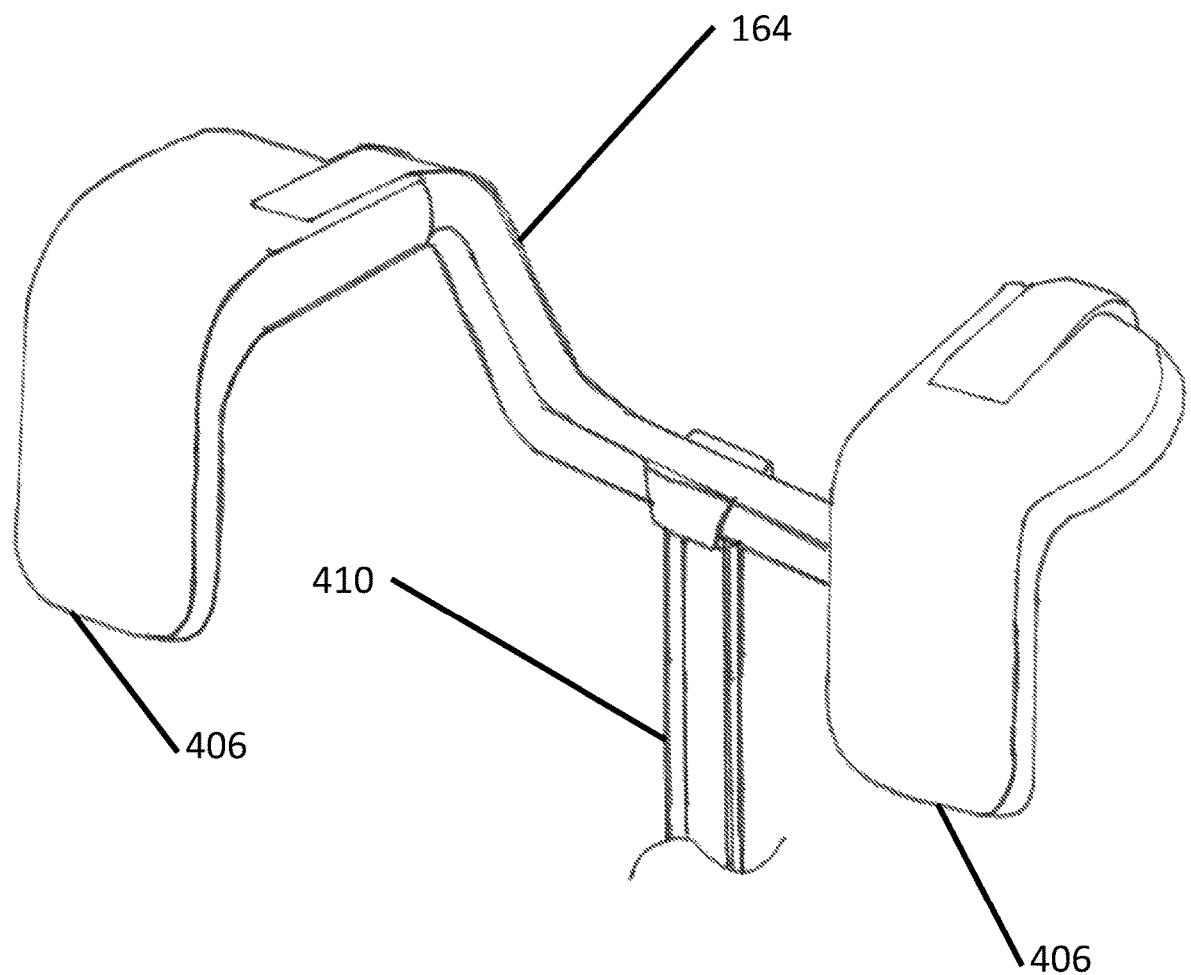
FIG. 47 shows an alternate embodiment of a shoulder puck.

Structural frame 164 may be configured to contact shielding apron 402 such that shielding apron 402 rests on top of structural frame 164, transferring the weight of shielding apron 402 to human interface device 100. Structural frame 164 may be configured to contact multiple points of shielding apron 402 such as the upper back area 403 located behind the persons shoulders or upper back, the shoulder area 404 located above the persons shoulders, or the upper chest area 405 located in front of the persons shoulders or chest as shown in FIG. 38. When human interface device 100 is worn under shielding apron 402 as shown in FIG. 40, structural frame 164 may be configured to terminate above the shoulders of person 104 and contact the upper back area 403 of shielding apron 402 or the shoulder area 404 of shielding apron 402. In some embodiments of the invention, not shown in the figures, structural frame 164 may be configured to terminate behind person 104 and not go above the shoulders of person 104 and contact the upper back area 403 of shielding apron 402. Still in other embodiments as shown in FIG. 47, structural frame 164 may be configured to at least partially wrap around the shoulders 104 of person and terminate in front of the chest of person 104 and contact the upper back area 403, upper chest area 405, or the shoulder area 404 of the shielding apron 402.

In some embodiments as shown in FIG. 41, load bearing structure 122 comprises one or a plurality of sections configured to slide into or over one another allowing for adjustment of structural frame 164 along vertical direction 414 relative to belt 118 (not shown) or frame 106.

Figure 44:
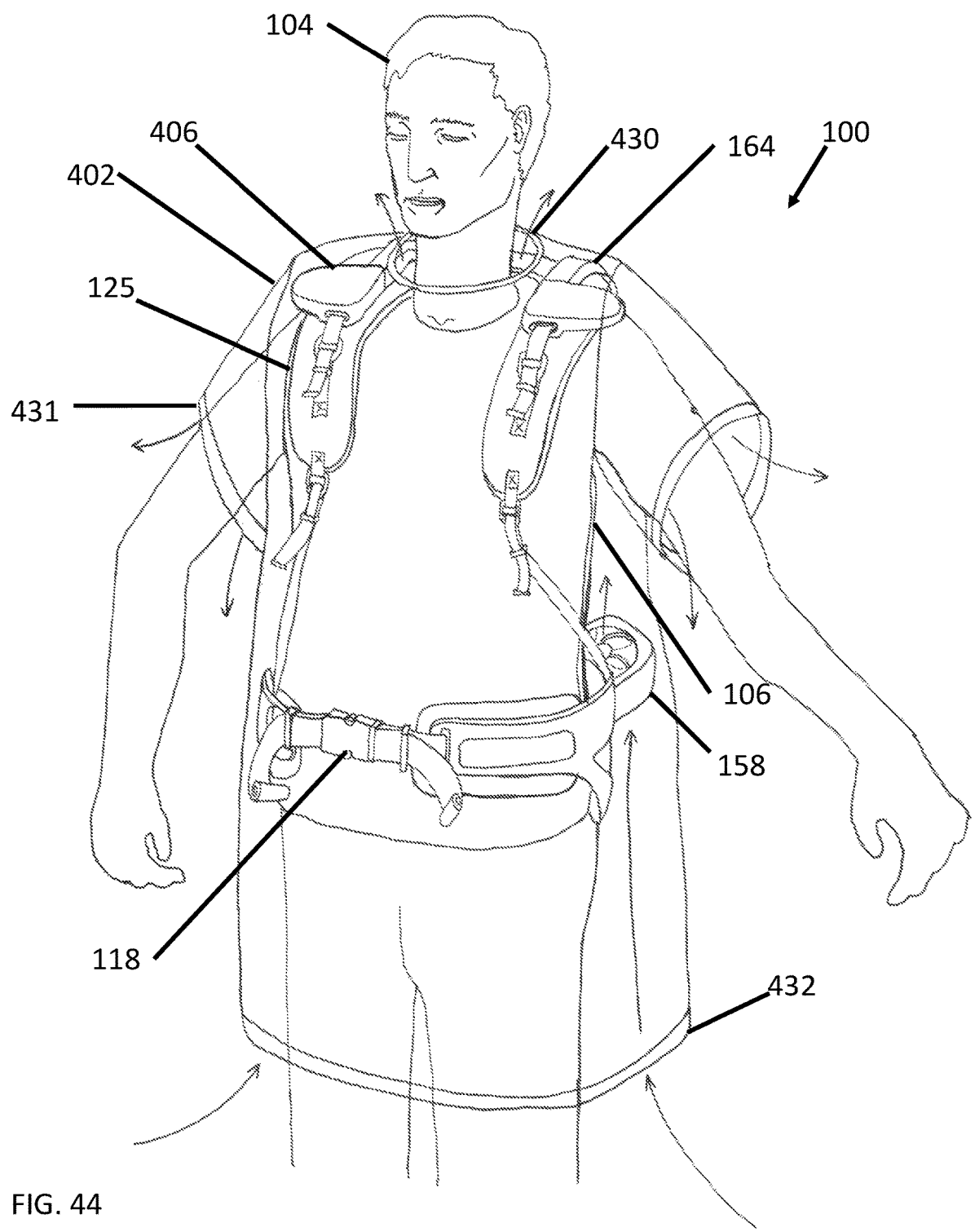
FIG. 44 shows a perspective view of the human interface device with mounted fans circulating air under a shielding apron.

In some embodiments of invention as shown in FIG. 41, structural frame 164 comprises left support strut 422 and right support strut 424 configured to stay above the person's shoulders transferring at least a portion of the weight of shielding apron 402 to frame 106. In some embodiments of invention, as shown in FIG. 41, the locations of left support strut 422 and right support strut 424 are adjustable so they can be located properly above the person's shoulder. In some embodiments, locations of left support strut 422 and right support strut 424 are adjustable in a horizontal direction 426. As shown in FIG. 41 the location of left support strut 422 and right support strut 424 can be adjusted along arrow of horizontal direction 426 relative to frame 106. The proper position above the person's shoulder may be determined by the position at which structural frame 164 best supports the area of shielding apron 402 between the collar 430 and sleeve 431 as shown in FIG. 44. In some cases, the proper position above the person's shoulder may be determined by the position at which structural frame 164 is least intrusive to the person's profile or range of motion.

Figure 46:
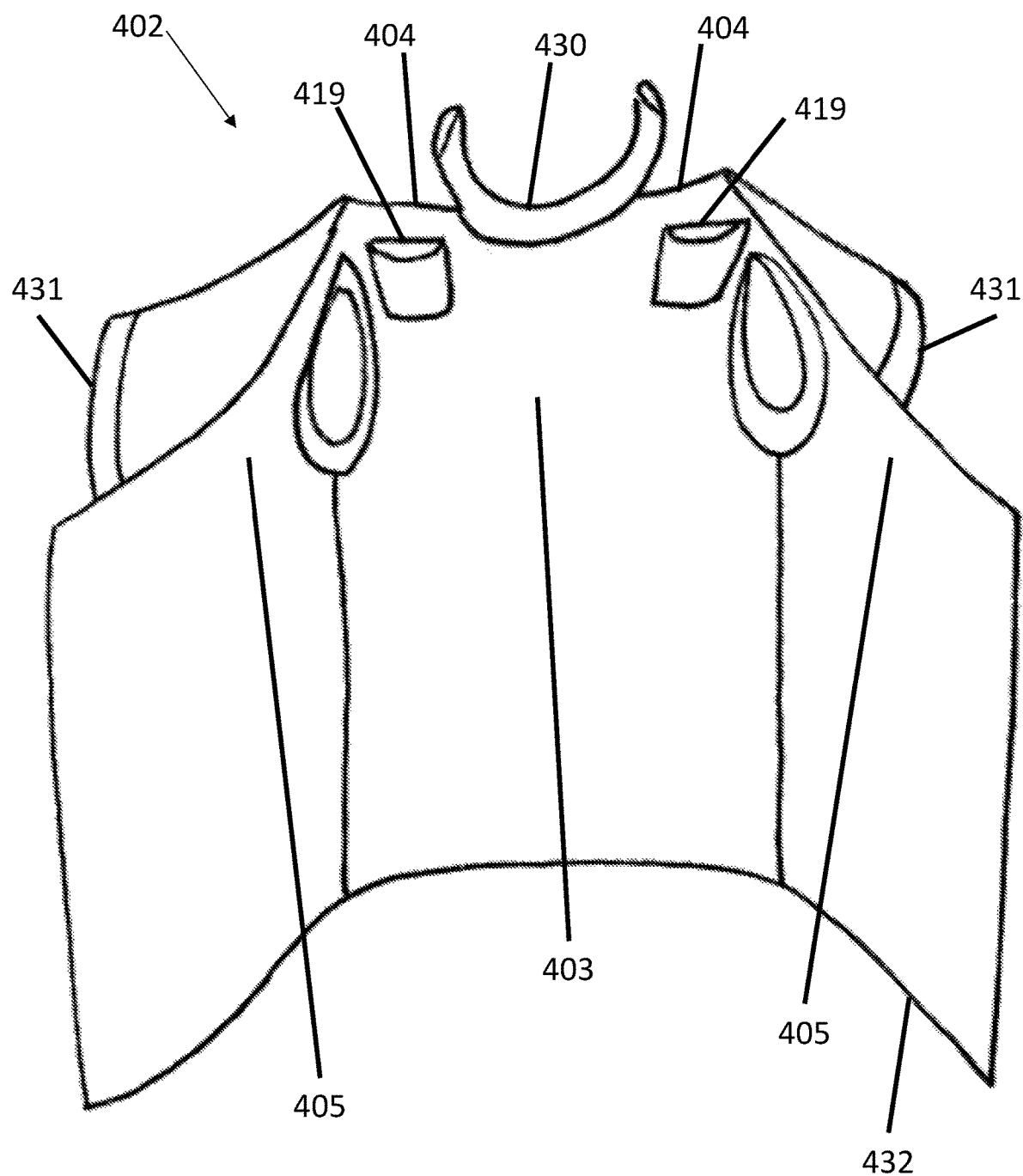
FIG. 46 shows an alternate embodiment of a shield coupling mechanism.

In some embodiments of the invention as shown in FIG. 39, human interface device 100 further comprises a shield coupling mechanism 419 configured to couple shielding apron 402 to structural frame 164. Among other methods, shield coupling mechanism 419 may comprise magnets, hook and loop, buckles, interlocking profiles, pockets, clasps, clamps, hooks, belts, or laces to secure shielding apron 402 to structural frame 164. A shield coupling mechanism 419 may be placed in one or both of human interface device 100 or shielding apron 402. Shield coupling mechanism 419 may be located above the shoulders of person, on one or both of the structural frame 164 of human interface device 100 or the inside shoulder area of shielding apron 402. In the embodiment of FIG. 39, coupling mechanism 419 comprises a magnet and female profile located on the two ends of structural frame 164 that locate above the shoulder of person 104 when human interface device 100 is worn. Additional coupling mechanism 419 comprising a magnet and male profile is located on the inside shoulder area 404 of shielding apron 419 and is configured to attract and lock into place with coupling mechanism 419 located on structural frame. To disconnect shielding apron 402 from structural frame 164, the two coupling mechanisms 419 must be pulled apart, overcoming the force of the magnets until the male profile no longer couples to female profile. In another embodiment shown in FIG. 46, shielding apron 402 comprises coupling mechanism 419 consisting of a pocket located on the shoulder area 404 of shielding apron 402 configured to allow structural frame 164 to slide into shielding apron 402. Pocket coupling mechanism 419 may be shaped to allow the ends of structural frame 164 to slide into shielding apron 402 in a single direction and prevent movement ion all other directions in order to couple human interface device 100 to shielding apron 402. In other embodiments not shown, pocket coupling mechanism 419 may be sown into the upper back area 403 or upper chest area 405 of shielding apron.

In some embodiments, shield coupling mechanism 419 results in human interface device 100 becoming a part of shielding apron 402, or vice versa, so that both are put on and taken off by the person at the same time as one unit. In this embodiment of the invention, a method of wearing shielding apron 402 with human interface device 100 comprises the steps of: coupling the shielding apron 402 to the human interface device 100 with shield coupling mechanism 419, coupling the human interface device 100 to the trunk of person 104, and finally closing or securing shielding apron 402. Taking off the human interface device 100 coupled to shielding apron 402 with shield coupling mechanism 419 results in the same steps in reverse. The embodiment of FIG. 39 may function in this manner when coupling mechanism 419 on structural frame 164 is attached to coupling mechanism 419 on shielding apron 402 before either human interface device 100 or shielding apron 402 is worn by person 104. While person 104 is putting on or taking off human interface device 100 coupled to shielding apron 402, coupling mechanism 419 keeps human interface device 100 coupled to shielding apron 402.

In other embodiments similar shield coupling mechanisms 419 may be utilized so that shielding apron 402 is only temporarily coupled to structural frame 164 to prevent relative movement between the two when worn by the person. In this embodiment both shielding apron 402 and human interface device 100 are put on or taken off separately, but when worn together become either manually or automatically coupled by shield coupling mechanism 419. The embodiment in FIG. 39 may also function in this manner if human interface device 100 is put on person 104 before shielding apron 402. When shielding apron 402 is put on by person 104 on top of human interface device 100, the magnets of coupling mechanism 419 will automatically connect the profile of coupling mechanism 419 on structural frame 164 to the coupling mechanism 419 on shielding apron 402. When person 104 takes off shielding apron 402 without taking off human interface device 100, coupling mechanism 419 must first be disconnected.

Figure 42:
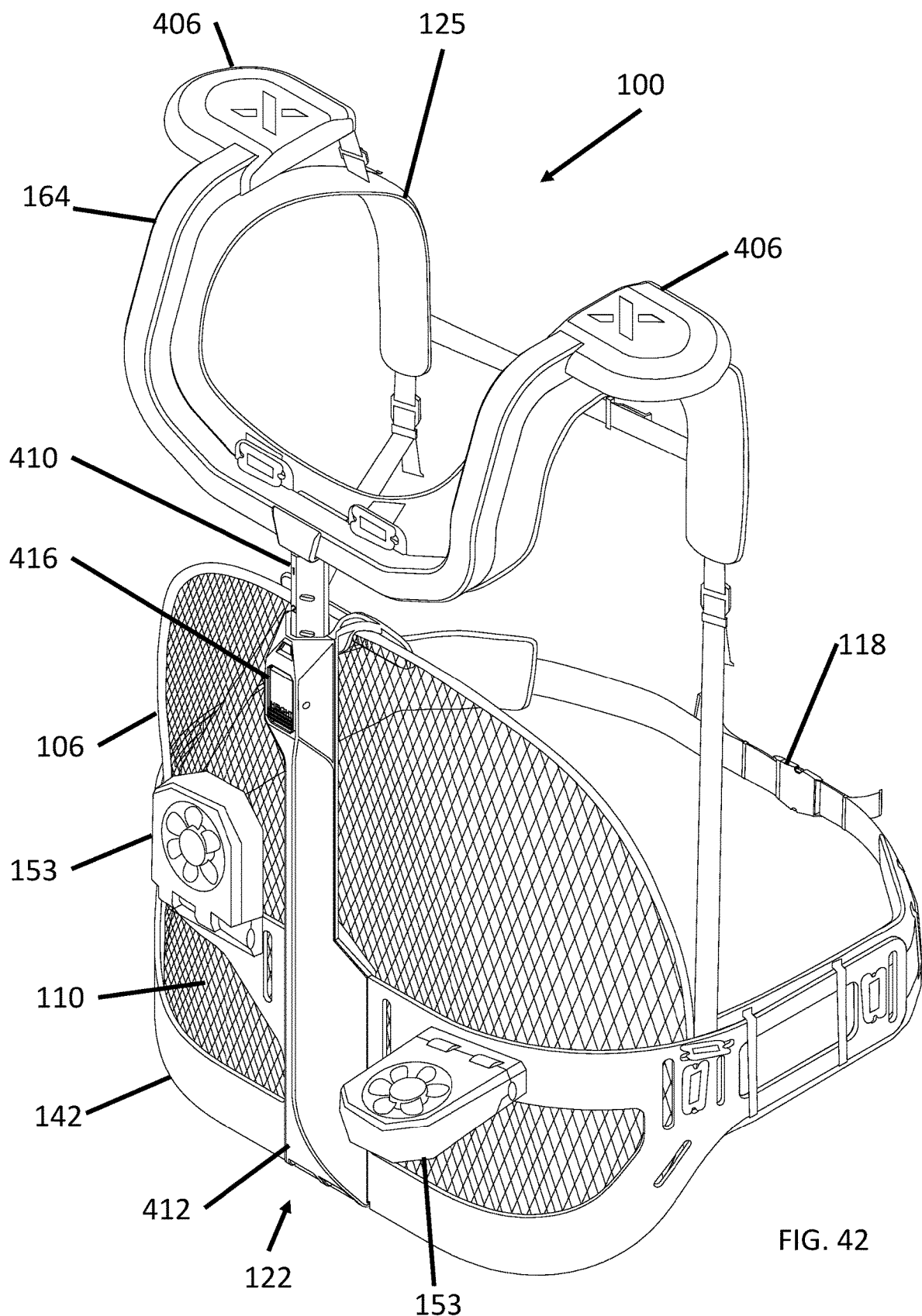
FIG. 42 shows a rear view of the human interface device configured to support a shielding apron with a fan attached.

Still in other embodiments as shown in FIG. 42, only the weight and friction forces of shielding apron 402 couple it to structural frame 164 when human interface device 100 is worn under shielding apron 402. Structural frame 164 may be shaped with contoured or high friction surfaces to minimize relative motion between shielding apron 402 and human interface device 100. Structural frame 164 may likewise be shaped with contoured surfaces to minimize damage to shielding apron 402 over time due to pressure points or sharp edges. FIG. 42 shows an embodiment of human interface device wherein structural frame 164 further comprises shoulder pucks 406. In the embodiment of FIG. 42, shoulder pucks 406 are located above the shoulders of person 104 when human interface device 100 is worn by person 104. In the embodiment of FIG. 47, shoulder pucks 406 are located above and in front of the shoulders of person 104. Shoulder pucks 406 may be shaped to maximize the surface area of shielding apron 402 that rests on structural frame 164. Shoulder pucks 406 may also be shaped to mirror the curve of the upper shoulders of person 104 to improve the fit and visual appearance of shielding apron 402 when worn on top of human interface device 100. Shoulder pucks 406 may also comprises ridges or a high friction surface finish to prevent shielding apron 402 from sliding relative to human interface device 100 when worn by person 104.

Figure 43:
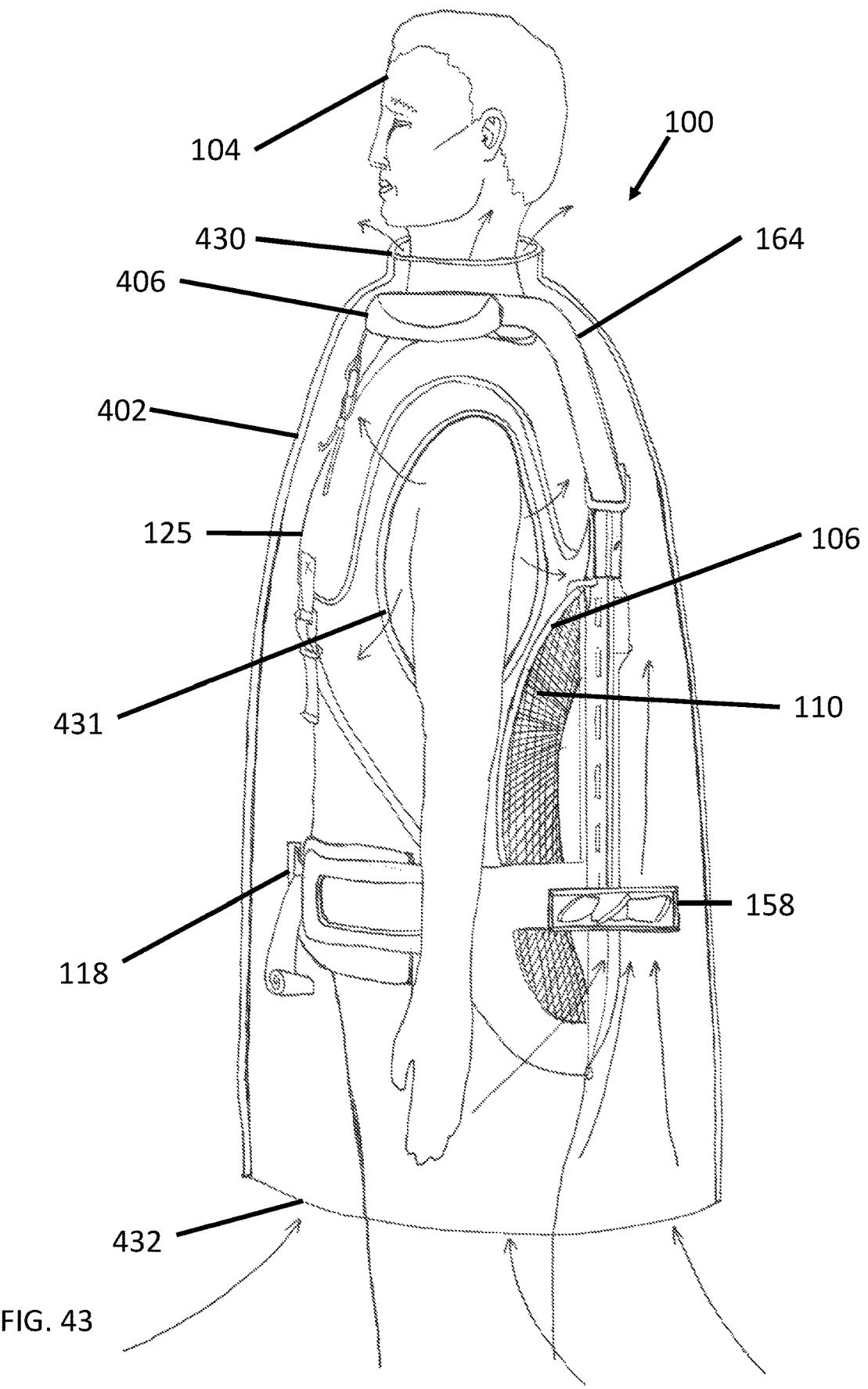
FIG. 43 shows a side view of the human interface device with mounted fans circulating air under a shielding apron.

In some embodiments of invention, as shown in FIG. 40 in profile view and FIG. 43 in side view, structural frame 164 may be contoured to closely follow the profile of persons body between the upper back of the person and the top or front of the shoulders of the person 104. When shielding apron 402 is worn over human interface device 100, the profile of structural frame 164 then minimizes the added profile of shielding apron 402 on person. This allows for the person to wear the same size shielding apron 402 with the human interface device 100 worn under it as when the shielding apron 402 is worn without human interface device 100. The profile of structural frame 164 also allows for shielding apron 402 to provide the same level of protection to the same areas of the body when worn with human interface device 100 as when shielding apron 402 is worn on its own.

In some embodiments as shown in FIG. 43, human interface device 100 is configured such that when shielding apron 402 rests on structural frame 164, a gap is formed between structural frame 164, and thus also shielding apron 402, and the person's body. The gap between shielding apron 402 and the body of person 104 created by human interface device 100 may be created along the lower back, upper back, above the shoulders, in front of the chest, or along the sides of person 104. This may ensure that no load from shielding apron 402 is placed on the shoulders or upper back of person 104. The gap between shielding apron 402 and the body of person 104 created by human interface device 100 may allow more airflow to person 104 and to keep them cooler and more comfortable when wearing shielding apron 402 for long periods of time. In some embodiments, dimensional adjustments of human interface device 100 along vertical direction 414 and horizontal direction 426 as shown in FIG. 41 may be used to configure the size of human interface device 100 relative to person 104 to create the aforementioned effects. In other embodiments, human interface device 100 may be produced in varying non-adjustable sizes to be matched with the size of a person 104 to create the aforementioned effects.

In some embodiments as shown in FIG. 42, FIG. 43, and FIG. 44, human interface device 100 may further comprise cooling element 158 optimized for use under shielding apron 402. In a primary embodiment, cooling element 158 is a fan attached to frame 106, strut 142, or load bearing structure 122. Fan cooling element 158 may also be referred to as fan 158. Fan 158 may be coupled to frame 106 near the curve of the lower back of person 104 such that when shielding apron 402 is worn over human interface device 100, fan 158 is located in a cavity formed between shielding apron 402 and the curve of the lower back of the person as seen in FIG. 43. This allows fan 158 to access a greater volume of air to increase airflow to person 104. In some embodiments of the invention, fan 158 is configured to circulate the air under shielding apron 402. In other embodiments as shown in FIG. 25 and FIG. 26, fan 158 is configured to blow air towards the lower back of person 104 through fabric 110, thus cooling the lower back of person 104. In some embodiments, as shown in FIG. 43, and FIG. 44, fan 158 is configured to blow substantially upwardly such that when human interface device 100 is worn by person 104 under shielding apron 402, fan 158 pulls air from the hem 432 of shielding apron 402 around persons legs and blows it across person's body towards at least one of the sleeve 431 or collar 430 of shielding apron 402. Fan 158 may be configured to protrude backwards behind the body of person 104 to increase the air-gap between the person 104 and shielding apron 402 to increase airflow. In some embodiments, fan 158 may be configured to blow at an angle between horizontal and vertical such that when human interface device 100 is worn by person 104 under shielding apron 402, fan 158 pulls air from the hem 432 of shielding apron 402 around person's legs and blows it across the person's body towards at least one of the sleeve 431 or collar 430 of shielding apron 402 as well as towards the lower back of the person 104 through fabric 110. In other embodiments structural frame 164 is configured to support shielding apron 402 such that an airgap is formed behind the persons upper back and around the persons shoulders to facilitate airflow from fan 158 around the body of person 104 and to the sleeve 431 and or collar 430 of shielding apron 402. Human interface device 100 may be adjusted along vertical direction 414 as described elsewhere and shown in FIG. 41 to create an airgap between person 104 and shielding apron 402.

Figure 45:
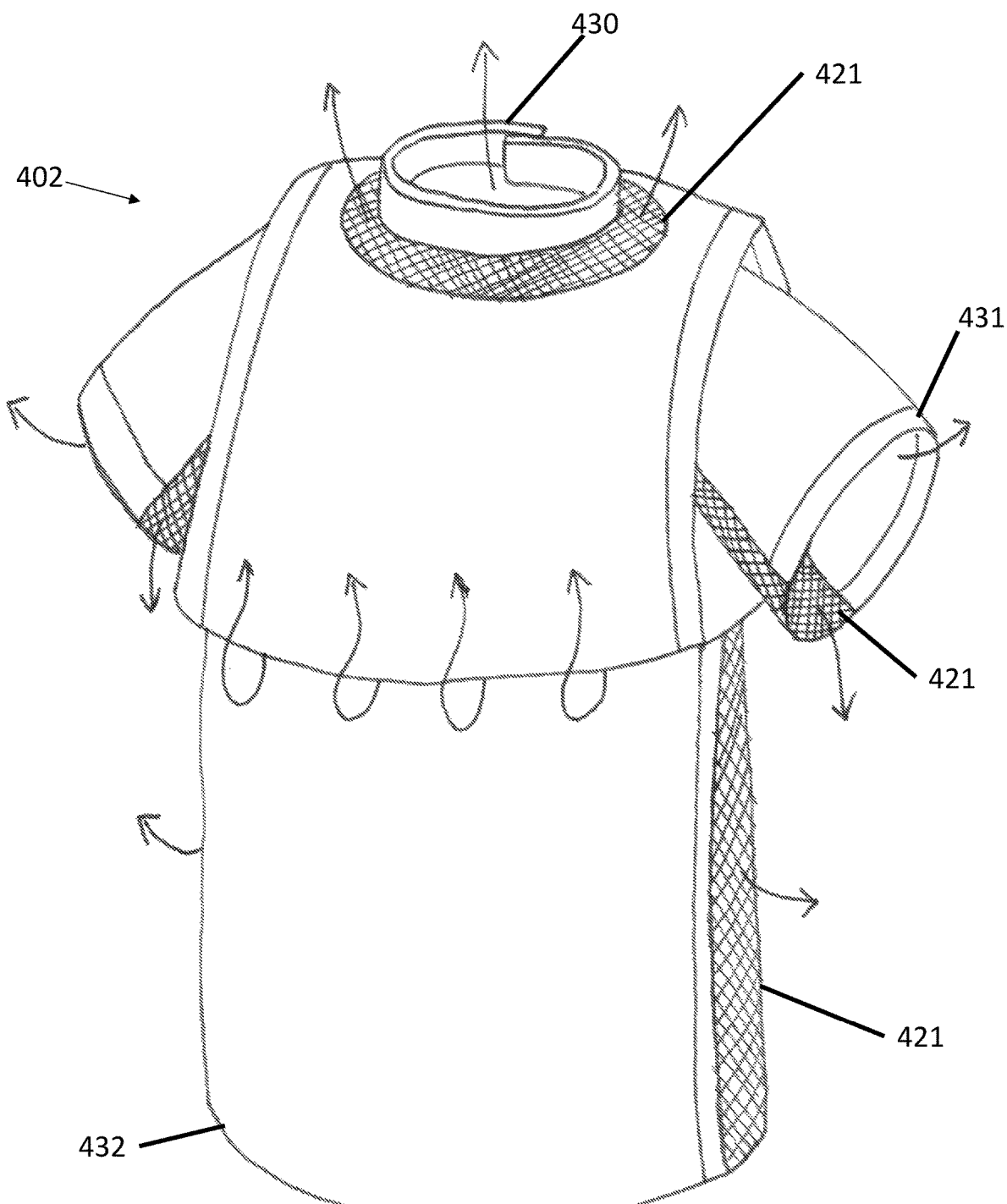
FIG. 45 shows a shielding apron with vents to increase airflow from human interface device fans.

In other embodiments as shown in FIG. 45, shielding apron 402 may be optimized for use with human interface device 100 with fan 158. Shielding apron 402 may further comprise channels (not shown) or vents 421 to increase the airflow to person 104 from fan 158. Vents 421 may be configured to allow air pushed by fan 158 to more easily escape from the inside of shielding apron 402 to the outside environment to increase the amount of air fan is able circulate. If applicable, vents 421 must be constructed as to not compromise the protection provided by shielding apron 402. Vents 421 may be constructed from various methods including but not limited to overlapping fabric layers or air permeable fabrics. In some embodiment vents 421 may be opened or closed by the person 104 to alter the amount of airflow, and thus the cooling effect. In other embodiments, vents 421 may be oriented such that, when opened, the airflow is directed towards a portion of the person not covered by the shielding apron 402, such as the head, face, or hands. In some embodiments, channels may be incorporated into shielding apron 402 to facilitate the movement of air between fan 158 and the body of person 104. Vertical channels may be used to route airflow from fan 158 to the upper back and on top of the shoulders of person 104. Horizontal channels may be used to round airflow around the sides and to the front of person 104. One skilled in the art may appreciate that there are many configurations of channels that may be used to route air throughout shielding apron 402. Among other means, channel may be constructed through pleats or folds in the fabric of shielding apron 402, semi rigid materials embedded into shielding apron 402, or ducts embedded into shielding apron 402. One skilled in the art may understand that fan 158 may similarly be used for heating a person if the air is passed through a heating element or drawn from a well of hotter air. The airflow created by fan 158 may similarly be used to diffuse a sent, whether towards or away from a person.

While some parts of the disclosure has been particularly shown and described with reference to wearable shielding aprons, it should be appreciated that variations in the form and details of the wearable shielding aprons may be made without departing from the spirit or scope of the disclosure. In some embodiment of invention, shielding apron 402 comprises a prop or a costume like those used in amusement parks such as Disney World, Disney Land, Universal Studios, Broadway Plays, Movie Sets and other entertainment settings. Human interface device 100 may be used to support the weight of a wearable costume or a prop, here represented by shielding apron 402. In many recreational and occupational settings, a person 104 must wear and carry a prop 402 on the body while standing, walking, or in seated positions. Wearable costumes and props are heavy. Persons engaged in such activities may experience fatigue or soreness in body regions where the weight of the prop is applied such as the hips or the shoulders. The weight of the prop 402 may further negatively affect the posture of person 104. In many cases, conventional human interface devices for carrying loads do not provide comfort for the person, 104 whether by inadequate conformance to the person's body shape or because of heat buildup due to lack of airflow. Thus, there is a need for a human interface device 100 that allows a person's body to better support a prop 402 or a costume 402 while promoting healthy posture of the person 104 without adding to the contact or thermal discomfort of the person 104. The embodiments of invention described here provide more comfort by conforming to the person's body maximizing the contact area thus minimizing the contact pressure on the person wearing a costume. In such cases human interface device 100 comprises a frame 106 compliant in a transverse plane, the frame 106 comprising a load bearing structure 122 configured to reduce a deformation of the frame 106 in a sagittal plane. Human interface device 100 comprises a fabric 110 coupled to the frame 106 which is configurable to be under tensile forces. Human interface device 100 comprises a belt 118 which is configured to be coupled to the frame 106. When the belt 118 is worn by the person, the frame 106 deforms in the transverse plane and an area of the fabric 110 will be pushed against the person's lower back conforming to a shape of the lower back of the person 104. In operation, when the human interface device 100 is coupled to the person, at least a portion of the weight of the costume or the prop 402 supported by the frame 106 will be supported by a friction force between the area of the fabric 110 which is pushed against the person's lower back, and the person's lower back allowing the person 104 to carry the costume or the prop 402. In some embodiments of invention, human interface device 100 comprises a structural frame 164 configured to stay above a person's shoulders and transfer at least a portion of the weight of the costume 402 to the frame 106.

A costume or prop 402 may comprise torso, head, neck, arms, legs, control cables, motors, batteries, and/or control boxes segments of a costume configured to be worn by person 104. A costume or a prop may be configured with passive or active animatronics such that control cables, motors, batteries, and controllers that are used to move features of the costume or a prop such as an eye or a mouth. A costume or a prop (here presented by shielding apron 402) may further comprise an internal frame to transfer loads from remote parts of the costume or a prop, such as limbs or wings, to human interface device 100. The internal frame of costume or a prop may be flexible to allow parts of a prop to move relative to other parts of the prop, such as a head relative to a torso, while transferring forces to human interface device 100. In other embodiments structural frame 164 of human interface device 100 may be shaped with contoured surfaces to fit the profile of the costume character of the prop. Examples of contoured surfaces that may be created by the structural frame 164 may include but is not limited to broad shoulders, hunchback, increased height, pointed shoulders, shortened neck, wings, an elongated body, or multiple heads.

Although many of the components and processes are described above in the singular for convenience, it will be appreciated by one of skill in the art that multiple components and repeated processes can also be used to practice the techniques of the present disclosure.

While the disclosure has been particularly shown and described with reference to specific embodiments thereof, it should be appreciated that changes in the form and details of the disclosed embodiments may be made without departing from the spirit or scope of the disclosure. It is therefore intended that the disclosure be interpreted to comprise all variations and equivalents that fall within the true spirit and scope of the present disclosure.

The following is claimed:

1. A human interface device configured to be coupled to a person to support a shielding apron comprising:
   a frame compliant in a transverse plane, the frame comprising a load bearing structure configured to reduce a deformation of the frame in a sagittal plane;
   a fabric coupled to the frame configurable to be under tensile forces; and
   a belt configured to be coupled to the frame wherein when the belt is worn by the person, the frame deforms in the transverse plane and an area of the fabric will be pushed against the person's lower back conforming to a shape of the lower back of the person, wherein when the human interface device is coupled to the person, at least a portion of a weight of the shielding apron supported by the frame will be supported by a friction force between the area of the fabric which is pushed against the person's lower back, and the person's lower back allowing the person to carry the shielding apron.

2. The human interface device of claim 1 further comprising a fan coupled to said frame to provide airflow over the person.

3. The human interface device of claim 2 wherein the fan is coupled to the frame near a curve of the lower back of the person such that when the shielding apron is worn over the human interface device, the fan is located in a cavity formed between the shielding apron and the curve of the lower back of the person.

4. The human interface device of claim 2 wherein the fan is configured to blow upwardly, wherein when the human interface device is worn by the person under the shielding apron, the fan blows across the person's body towards at least one of a collar or a sleeve of the shielding apron.

5. The human interface device of claim 2 wherein the fan is configured to blow toward and through the fabric.

6. The human interface device of claim 1 wherein said shielding apron is a radiation shielding apron to minimize an exposure of said person to x-ray radiation.

7. The human interface device of claim 1 wherein said shielding apron is selected from a group consisting of a blast shield, riot shield, ballistic vest, armor vest, and bullet-proof vest.

8. The human interface device of claim 1 wherein said human interface device comprises a structural frame configured to stay above a person's shoulders and transfer at least a portion of the weight of the shielding apron to the frame.

9. The human interface device of claim 8 wherein the structural frame is configurable to support the inside shoulder face of the shielding apron.

10. The human interface device of claim 8 wherein the load bearing structure comprises at least two sections configured to slide into or over one another allowing for an adjustment of the structural frame along a vertical direction relative to the belt.

11. The human interface device of claim 8 wherein the structural frame further comprises a left support strut and a right support strut that are adjustable along a horizontal direction so they can be located properly above the persons shoulder.

12. The human interface device of claim 1, further comprising an upper torso coupling to secure the frame to the person's upper torso causing a more effective contact between the fabric and the person.

13. The human interface device of claim 12, wherein said upper torso coupling comprises two shoulder straps wherein each shoulder strap is coupled to an upper edge of the frame from one end and to the lower side of the frame from their second ends wherein when the two shoulder straps are worn by the person, the tightening of the two shoulder straps causes a more effective contact between the fabric and the person.

14. A human interface device configured to be coupled to a person to support a shielding apron comprising:
a frame compliant in a transverse plane configurable to support the shielding apron, wherein said frame comprises a structural frame configured to stay above the person's shoulders and transfer at least a portion of a weight of the shielding apron to the frame;
a belt configured to be coupled to said frame and secure the frame to the person,
wherein when the belt is worn by the person, the frame deforms in the transverse plane conform to a shape of the lower back of the person, and
wherein when the human interface device is worn by the person, at least a portion of the weight of the shielding apron is transferred to the person.

15. The human interface device of claim 14 wherein the frame transfers at least a portion of the weight of the shielding apron to the hips of the person.

16. The human interface device of claim 14 wherein the frame transfers at least a portion of the weight of the shielding apron to the lower back of the person.

17. The human interface device of claim 14 further comprising a fabric coupled to said frame configurable to be under tensile forces; wherein when the human interface device is worn by the person, at least a portion of the weight of the shielding apron will be partially supported by a friction force between an area of the fabric which is pushed against the person's lower back, and the person's lower back.

18. The human interface device of claim 14 wherein the frame comprises a load bearing structure configured to reduce a deformation of the frame in a sagittal plane.

19. The human interface device of claim 14 wherein said structural frame is configurable to support the inside shoulder face of the shielding apron.

20. The human interface device of claim 14 further comprising a fan coupled to said frame to provide airflow over the person.

21. A human interface device configured to be coupled to a person to support a shielding apron comprising:
a frame to support a shielding apron, wherein said frame comprises a structural frame configured to stay above the person's shoulders and transfer at least a portion of a weight of the shielding apron to the frame;
a belt configured to couple the frame to the person; and
a fan coupled to said frame to provide airflow;
wherein when the human interface device is coupled to the person, at least a portion of the weight of the shielding apron is transferred to the person and the fan provides the airflow over the person.

22. The human interface device of claim 21 wherein the frame is compliant in a transverse plane, wherein when the belt is worn by the person, the frame deforms in the transverse plane conforming to a shape of the lower back of the person.

23. The human interface device of claim 21 further comprising a fabric coupled to said frame configurable to be under tensile forces.

24. The human interface device of claim 23 wherein when the belt is worn by the person, the frame deforms in the transverse plane and an area of the fabric will be pushed against the person's lower back conforming to a shape of the lower back of the person.

25. The human interface device of claim 23 wherein the fabric allows for air through and the fan is configured to blow toward the fabric.

26. The human interface device of claim 21 wherein the frame further comprises a structural frame configured to stay above a person's shoulders and create an airgap between the shielding apron and the persons shoulders.

27. The human interface device of claim 21 wherein the frame comprises a load bearing structure configured to reduce a deformation of the frame in a sagittal plane.

28. The human interface device of claim 21 wherein the fan is coupled to the frame near a curve of the lower back of the person such that when a shielding apron is worn over the human interface device, the fan is located in a cavity formed between the shielding apron and the curve of the lower back of the person.

29. The human interface device of claim 21 wherein the fan is configured to blow upwardly, wherein when the human interface device is worn by the person under the shielding apron, the fan blows across the person's body towards at least one of a collar or a sleeve of the shielding apron.

* * * * *